(12) United States Patent
Carson et al.

(10) Patent No.: US 9,117,016 B2
(45) Date of Patent: Aug. 25, 2015

(54) UNIVERSAL LABEL AND VERIFICATION SYSTEMS AND METHODS FOR FILLING CUSTOMER ORDERS OF MEDICAL ITEMS

(71) Applicant: Omnicare, Inc., Cincinnati, OH (US)

(72) Inventors: Bradley E. Carson, Ottawa Hills, OH (US); Jack M. Friday, Monroe, MI (US)

(73) Assignee: Omnicare, Inc., Cincinnati, OH (US)

( * ) Notice: Subject to any disclaimer, the term of this patent is extended or adjusted under 35 U.S.C. 154(b) by 109 days.

(21) Appl. No.: 13/801,017

(22) Filed: Mar. 13, 2013

(65) Prior Publication Data

US 2014/0021253 A1  Jan. 23, 2014

Related U.S. Application Data

(60) Provisional application No. 61/674,644, filed on Jul. 23, 2012, provisional application No. 61/674,649, filed on Jul. 23, 2012.

(51) Int. Cl.
*G06F 19/00* (2011.01)
*G06Q 30/00* (2012.01)

(52) U.S. Cl.
CPC ........ *G06F 19/3462* (2013.01); *G06F 19/3456* (2013.01); *G06Q 30/018* (2013.01)

(58) Field of Classification Search
USPC .................................................. 235/381, 380
See application file for complete search history.

(56) References Cited

U.S. PATENT DOCUMENTS

| | | |
|---|---|---|
| 3,606,014 A | 9/1971 | Linn |
| 3,656,616 A | 4/1972 | Wallington |
| 3,882,316 A | 5/1975 | Garris |
| 4,011,155 A | 3/1977 | Feurstein et al. |
| 4,053,056 A | 10/1977 | Day |
| 4,530,199 A | 7/1985 | Manservisi et al. |
| 5,101,609 A | 4/1992 | Cook |
| 5,406,770 A | 4/1995 | Fikacek |
| 5,568,715 A | 10/1996 | Ebel et al. |
| 5,593,267 A | 1/1997 | McDonald et al. |

(Continued)

FOREIGN PATENT DOCUMENTS

| | | |
|---|---|---|
| CA | 2509120 A1 | 2/2006 |
| EP | 1388336 A1 | 11/2004 |
| EP | 1889802 A2 | 2/2008 |

OTHER PUBLICATIONS

USPTO, Office Action issued in U.S. Appl. No. 13/801,070 dated Mar. 3, 2015.

*Primary Examiner* — Allyson Trail
(74) *Attorney, Agent, or Firm* — Wood, Herron & Evans, LLP

(57) ABSTRACT

Label and verification systems and methods to assist with manual labeling and verification of various types of products including medical items that may be filled as part of a customer order, including boxes, cards, bottles, and many other known types of containers. The label and verification system prompts a user to scan a product label on a product, determines whether the product label corresponds to one of the medical items in the customer order, and then prints a patient label for the product. After prompting the user to affix the patient label to the product and rescan the product, the system verifies that the correct patient label and product label are on the product from the customer order. The system and method may be operable to label more than 90% of containers commonly used to hold medications and medical items with increased speed and accuracy.

19 Claims, 28 Drawing Sheets

(56) References Cited

U.S. PATENT DOCUMENTS

| | | |
|---|---|---|
| 5,597,995 A | 1/1997 | Williams et al. |
| 5,660,305 A | 8/1997 | Lasher et al. |
| 5,720,154 A | 2/1998 | Lasher et al. |
| 5,771,657 A | 6/1998 | Lasher et al. |
| 5,880,443 A | 3/1999 | McDonald et al. |
| 5,883,370 A | 3/1999 | Walker et al. |
| 5,905,653 A | 5/1999 | Higham et al. |
| 5,963,453 A | 10/1999 | East |
| 6,158,193 A | 12/2000 | Focke et al. |
| 6,317,648 B1 | 11/2001 | Sleep et al. |
| 6,373,520 B1 | 4/2002 | Cadieux, Jr. et al. |
| RE37,829 E | 9/2002 | Charhut et al. |
| 6,449,927 B2 | 9/2002 | Hebron et al. |
| 6,464,142 B1 | 10/2002 | Denenberg et al. |
| 6,471,089 B2 | 10/2002 | Liff et al. |
| 6,522,945 B2 | 2/2003 | Sleep et al. |
| 6,575,216 B2 | 6/2003 | Yang |
| 6,655,015 B2 | 12/2003 | Kraenzle |
| 6,735,497 B2 | 5/2004 | Wallace et al. |
| 6,748,295 B2 | 6/2004 | Tilles et al. |
| 6,776,304 B2 | 8/2004 | Liff et al. |
| 6,814,254 B2 | 11/2004 | Liff et al. |
| 6,814,255 B2 | 11/2004 | Liff et al. |
| 6,847,861 B2 | 1/2005 | Wangu et al. |
| 6,892,512 B2 | 5/2005 | Rice et al. |
| 6,970,769 B2 | 11/2005 | Rice et al. |
| 6,971,213 B2 | 12/2005 | Battisti |
| 6,983,579 B2 | 1/2006 | Rice et al. |
| 7,006,893 B2 | 2/2006 | Hart et al. |
| 7,010,899 B2 | 3/2006 | McErlean et al. |
| 7,047,706 B2 | 5/2006 | Kraenzle |
| 7,084,738 B2 | 8/2006 | Bastian, II |
| 7,086,558 B1 | 8/2006 | Pixley et al. |
| 7,100,792 B2 | 9/2006 | Hunter et al. |
| 7,185,477 B2 | 3/2007 | Rice et al. |
| 7,269,476 B2 | 9/2007 | Ratnakar |
| 7,334,379 B1 | 2/2008 | Siegel et al. |
| 7,386,965 B2 | 6/2008 | McErlean et al. |
| RE40,453 E | 8/2008 | Lasher et al. |
| 7,409,977 B2 | 8/2008 | Rice et al. |
| 7,412,814 B2 | 8/2008 | Rice et al. |
| RE40,510 E | 9/2008 | Lasher et al. |
| 7,427,002 B2 | 9/2008 | Liff et al. |
| 7,430,838 B2 | 10/2008 | Rice et al. |
| 7,440,817 B2 | 10/2008 | Fu |
| 7,467,093 B1 | 12/2008 | Newton et al. |
| 7,513,091 B2 | 4/2009 | Moodley |
| 7,676,299 B2 | 3/2010 | Clarke et al. |
| 7,721,512 B2 | 5/2010 | Siegel et al. |
| 7,753,085 B2 | 7/2010 | Tribble et al. |
| 7,774,097 B2 | 8/2010 | Rosenblum |
| 7,882,680 B2 | 2/2011 | Siegel et al. |
| 7,984,602 B2 | 7/2011 | Kraenzle |
| 8,002,174 B2 * | 8/2011 | Coyne et al. ............... 235/375 |
| 8,121,725 B2 | 2/2012 | Baker et al. |
| 8,215,540 B2 | 7/2012 | Szesko et al. |
| 8,231,749 B2 | 7/2012 | Dent et al. |
| 8,262,842 B2 | 9/2012 | Szesko et al. |
| 8,744,621 B2 | 6/2014 | Michael |
| 2002/0026768 A1 | 3/2002 | Duncan et al. |
| 2002/0117405 A1 | 8/2002 | Wang et al. |
| 2003/0088333 A1 * | 5/2003 | Liff et al. ............... 700/237 |
| 2003/0125837 A1 | 7/2003 | Walace et al. |
| 2003/0176942 A1 | 9/2003 | Sleep et al. |
| 2004/0210341 A1 | 10/2004 | Wallace et al. |
| 2004/0215486 A1 | 10/2004 | Braverman |
| 2006/0161294 A1 | 7/2006 | DiMaggio |
| 2006/0161298 A1 | 7/2006 | DiMaggio |
| 2006/0277269 A1 * | 12/2006 | Dent et al. ............... 709/217 |
| 2007/0102109 A1 | 5/2007 | Katritzky et al. |
| 2007/0271001 A1 | 11/2007 | Ratnakar |
| 2008/0172305 A1 * | 7/2008 | Estes et al. ............... 705/26 |
| 2008/0229718 A1 | 9/2008 | Feehan et al. |
| 2009/0173779 A1 * | 7/2009 | Szesko et al. ............... 235/375 |
| 2011/0202481 A1 * | 8/2011 | Lang et al. ............... 705/500 |

* cited by examiner

UNIVERSAL LABEL AND VERIFICATION SYSTEMS AND METHODS FOR FILLING CUSTOMER ORDERS OF MEDICAL ITEMS

CROSS-REFERENCE TO RELATED APPLICATIONS

This application claims the benefit of U.S. Patent Application No. 61/674,644, filed Jul. 23, 2012, and also claims the benefit of U.S. Patent Application No. 61/674,649, filed Jul. 23, 2012, the disclosures of which are incorporated by reference herein in their entirety.

BACKGROUND

Conventionally, pharmacies have filled large quantities of customer orders for skilled nursing facilities, assisted living facilities, independent living facilities, group homes, hospice facilities and other configurations of the nursing home industry and institutionalized long term care industry with a labor-intensive, pharmacist-based, assembly line method. Typically, a customer order is comprised of patient prescriptions issued by a physician and fulfilled under close pharmacist supervision. In general, filling of prescriptions consists of executing the customer order by associating the correct pharmaceutical product with the correct prescription label. Generally, such filling is performed by pharmacists, technicians, or combinations of these individuals. The prescription labels with patient information (hereafter referred to as "patient labels") are typically printed out in batch form with smaller flag labels, containing subsets of the information contained on the patient labels, for every patient label regardless of whether the product requires a flag label or not, and these batches of labels are carried around by the individuals collecting the packages from bulk inventory. Products in the form of a variety of packages (e.g., 24-Hour, 7-day, 14-day, 15-day, 30-day dosages, and individually by form and strength) are removed from bulk inventory and, thereafter, a prescription label is printed and manually applied to the appropriate product.

Following collection of the products and application of the patient labels, the application may then be verified in one of many ways. It can be checked against a master order sheet (MAR) or visually checked by the technician, pharmacist, or a combination of these individuals. The correct patient label application can also be verified by manually scanning the barcode or indicia on the prescription label and looking up the required prescription medication name, strength and dose which is then matched to the barcode or indicia that is scanned on the product/package label. If these attributes match, then the patient centric labeled product/package is considered to be verified. Once each patient centric labeled product is verified, then the patient centric labeled products are grouped and presorted into containers. The grouping and presorting of products can be done based on the patient, the residence of the patient or shipping location, the delivery method or carrier, time of day, or any other styled grouping of such. The presorted containers are broken down in a sorting area where the products are individually scanned and placed into the shipping containers (e.g., boxes, bags, bins, or totes). Typically at this point, the label application is re-verified and the product's association with the particular shipping container is checked. This is a barcode-scanning step where the package label, the prescription label, and the shipping container (or any combinations of these items) are confirmed to be correct. By the time a labeled and verified product is correctly placed in a shipping tote, it has typically been handled or touched by an individual up to approximately 11-13 times. The large number of touches required to process products represents inefficiencies and increases the potential for human error.

In an attempt to address these process inefficiencies and reduce the number of required human touches for each product, an automated label and verification system has been developed as described in U.S. Pat. No. 8,215,540 to Szesko et al., which is co-owned by the assignee of the present invention and is hereby incorporated by reference herein in its entirety. The automated label and verification system includes a turntable configured to receive a stack of blister cards or a series of product boxes. Robotic machinery scans the product labels on these blister cards and product boxes, positions the cards/boxes on the turntable, rotates the cards/boxes to a label printing and application station where a patient label is printed and applied on demand, scans both labels for verification of proper labeling, and rotates the cards/boxes to a removal station where a robot moves the cards/boxes into totes for downstream processing and shipping. The automated label and verification system has greatly increased the efficiency and improved the quality of the prescription filling process for blister cards and product boxes by automating the label printing, application, and verification process to reduce human touches required.

However, blister cards and product boxes are only used for up to about 55-60% of the prescriptions that are filled by pharmacies. The remaining percentage of the prescriptions has unique package shapes and sizes (for example, bottles, vials, ampoules, flexible tubes) that cannot be easily handled by an automated label and verification system without significant reconfiguration and excessive expense in the robotic equipment used. These products continue to be labeled and verified using the traditional manual process described above. On average, the manual process results in only about 1 product being picked, labeled, verified, transported and presorted every one to three minutes, in contrast with the up to 16 to 18 products labeled and verified per minute by the automated label and verification system. Therefore, there remains significant opportunity for improvement in the current methodologies used by pharmacies to fill prescriptions against customer orders. More specifically, it would be desirable to minimize the human touches required in order to improve quality while increasing efficiency for other types of product packaging beyond just blister cards and product boxes.

SUMMARY OF THE INVENTION

According to one embodiment, a method is operable to fill a customer order containing at least one product to be labeled and verified with an LV kiosk including a scanner, a label printer, and a human machine interface (HMI). Each product includes a medical item contained in the customer order. The method includes prompting a user with the HMI to scan a product label on a product contained in the customer order at the scanner. Once first identification data from the product label is received following the scan of the product label, it is determined whether this first identification data corresponds to a medical item contained in the customer order. The label printer then prints a patient label containing second identification data if the first identification data corresponds to at least one of the medical items contained in the customer order. The second identification data is associated with a patient who is to receive the product. The user is then prompted with the HMI to affix the patient label to the product and then scan the product label and patient label at the scanner. The method also includes verifying that the patient label was affixed to the product by confirming that the first and second identification data were each received and correctly correspond to the customer order when the product label and the patient label are scanned by the user at the scanner.

In one aspect, the method also includes generating pick instructions identifying a storage location for each of the products contained in the customer to be filled. The pick instructions are provided to the user with the HMI for a first product contained in the customer order, and this allows the user to retrieve the first product and then label and verify the first product. The steps of providing the pick instructions and labeling and verifying are repeated for each other product contained in the customer order. For example, the LV kiosk includes a display screen at the HMI and a kiosk housing separated from a plurality of racks and carousels defining storage locations for bulk supply of medical items. In such embodiments, a message is generated in the display screen to identify which of the plurality of racks and carousels hold the first product to be retrieved by the user. In another example, the LV kiosk includes a kiosk housing connected to a storage carousel located within a cage having a door. In such alternative embodiments, the method includes determining with the pick instructions a first location on the storage carousel where a storage bin holds the first product to be retrieved. The storage carousel is then actuated to rotate the first location to the door of the cage such that the user can retrieve the first product.

In addition, the LV kiosk connected to the storage carousel may also include a plurality of pick modules that are located on the kiosk housing at corresponding levels of shelves on the storage carousel. The pick module corresponding to the shelf level where the first product is located is selectively operated when the first location has been rotated to the door of the cage so that the user can follow the pick module to pick the first product for the customer order. After the first product has been labeled and verified, the user is prompted to put the first product into a storage tote located proximate to the LV kiosk. Simultaneously, the storage carousel is rotated so that a second location where a second product to be retrieved is positioned adjacent to the door of the cage. This enables the next item to be retrieved to be ready for the user immediately after the user has placed the previous item in the tote. It is also possible for the LV kiosk to be connected to a plurality of storage carousels, and in such embodiments, a message is generated on the display screen of the HMI to instruct a user which of the storage carousels contains the first location with the first product to be retrieved for a customer order. In another aspect, the storage carousel includes a light curtain optical sensor adjacent the door which detects an entry of a user's arm into the storage carousel so that rotating movement of the storage carousel is stopped anytime a user's arm is inside the cage and at risk of injury.

The LV kiosk and storage carousel may be used to deliver controlled substances to authorized users filling customer orders. In this regard, the door on the cage is motorized and at least some of the storage bins in the storage carousel contain controlled substances. The motorized door is closed to prevent access to the storage bins before any pick information has been provided to the user. The method includes verifying third identification data provided by the user at the HMI to determine if the user is authorized to retrieve controlled substances. If the user is authorized, the motorized door only opens when the first location has been rotated to the door of the cage. This operation prevents even the authorized user from gaining temporary access to storage bins in the storage carousel that should not be accessed for the customer order. Moreover, controlled substances of different schedule levels may be kept in different vertical columns of storage bins formed by the storage carousel, thereby separating controlled substances of different schedule levels in independent pie-piece-shaped portions of the storage carousel. As one vertical column is all that is ever accessible at the door, the method includes rotating the storage carousel such that the portions of the storage carousel containing controlled substances of a schedule level higher than what the user is authorized to remove are never rotated past the door, thereby preventing a user from having even temporary access to controlled substances of a schedule level higher than what the user is authorized to remove.

If the first identification data is not determined to correspond to at least one of the medical items in the customer order, then the user will be prompted to return that product and retrieve a new product that is contained in the customer order. If the first and second identification data cannot be verified to correctly correspond to the customer order, then a replacement label is printed at the label printer. The HMI prompts the user to remove the patient label originally affixed to the product, to affix the replacement patient label to the product, and to scan the product label and the replacement patient label at the scanner. For some medications, a flag label having a subset of the information contained on the patient label must also be applied within the exterior packaging. In such cases, the label printer or a separate flag label printer automatically prints a flag label responsive to determining that a current product being retrieved is a flag label product, such that the user can affix the flag label to the product.

In another aspect, the method includes generation of batch data for a tote that may be used to move products to and from the LV kiosk. The user is prompted to scan an empty tote that is to be used to receive the products contained in the customer order. The user scans fourth identification data from the tote and it is determined whether the empty tote is logically free to receive the customer order. In response to determining that the empty tote is logically free to receive the customer order, batch data is generated that indicates each product to be placed in the empty tote and pick instructions for each of the products to be placed in the empty tote.

According to another embodiment of the invention, a label and verification kiosk is configured to fill a customer order with at least one medical item. The kiosk includes a kiosk housing, a label printer operable to print a patient label, and a scanner operable to scan product labels on products and patient labels. A human machine interface with a display screen is located at the kiosk housing and is configured to provide instruction prompts to a user. The kiosk also includes a controller having a processor and a memory, with a program code resident in the memory and configured to be executed by the processor. The program code determines if first identification data from a product label scanned by a user at the scanner corresponds to one of the medical items in the customer order, actuates printing of a patient label containing second identification data with the label printer, and prompts the user with the HMI to affix the patient label to the product. The program code also verifies that the patient label was affixed to the product by confirming that the first and second identification data were each received when the product label and the patient label are scanned by the user. Consequently, manual labeling and verification can be quickly performed at the kiosk for over 90% of containers used for various types of medications and medical items.

At least one auxiliary shelf may be located at the kiosk housing. The auxiliary shelf holds a tote in proximate relation to the label printer, the scanner, and the HMI, such that a user can keep a tote of retrieved products close to the kiosk during the labeling and verification process. In this regard, the need to walk around or bend over to retrieve each item is removed using the totes on the auxiliary shelf or shelves. The kiosk also includes a work shelf projecting from the kiosk housing adjacent to the label printer and the scanner. The work shelf is sized to accommodate one product at a time, and this encourages the user to label and verify only one product at a time when using the kiosk.

In another embodiment of the invention, a label and verification system is configured to fill a customer order with at least one medical item. The system includes a storage carousel including a plurality of radially oriented storage bins on a plurality of shelves for holding bulk supply of medical items. A cage surrounds the storage carousel and includes a door configured to provide selective access to one of the storage bins on each shelf. The system further includes a label and verification kiosk, which includes a kiosk housing at least partially surrounding the storage carousel, a label printer operable to print a patient label, and a scanner operable to scan product labels on products and patient labels. The kiosk also includes a controller having a processor and a memory, with a program code resident in the memory and configured to be executed by the processor. The program code identifies a first location in the storage carousel containing a storage bin with a first product for the customer order, actuates the storage carousel to rotate the first location to the door, and actuates a manual labeling and verification of the first product after it has been retrieved from the storage carousel. Similar to previous embodiments, manual labeling and verification can be quickly performed at the kiosk for over 90% of containers used for various types of medications and medical items.

A light curtain optical sensor is coupled to the controller and located adjacent the door in some embodiments. The optical sensor detects entry of a user's hand into the storage carousel from outside the cage. As a result, the rotation of the storage carousel may be stopped anytime the user's arm penetrates through the field of the optical sensor. A plurality of pick modules may be provided on the kiosk adjacent to the door, with each pick module corresponding to an appropriate shelf or level in the storage carousel.

Various additional features and advantages of the invention will become more apparent to those of ordinary skill in the art upon review of the following detailed description of the illustrative embodiments taken in conjunction with the accompanying drawings.

DETAILED DESCRIPTION

Figure 1:
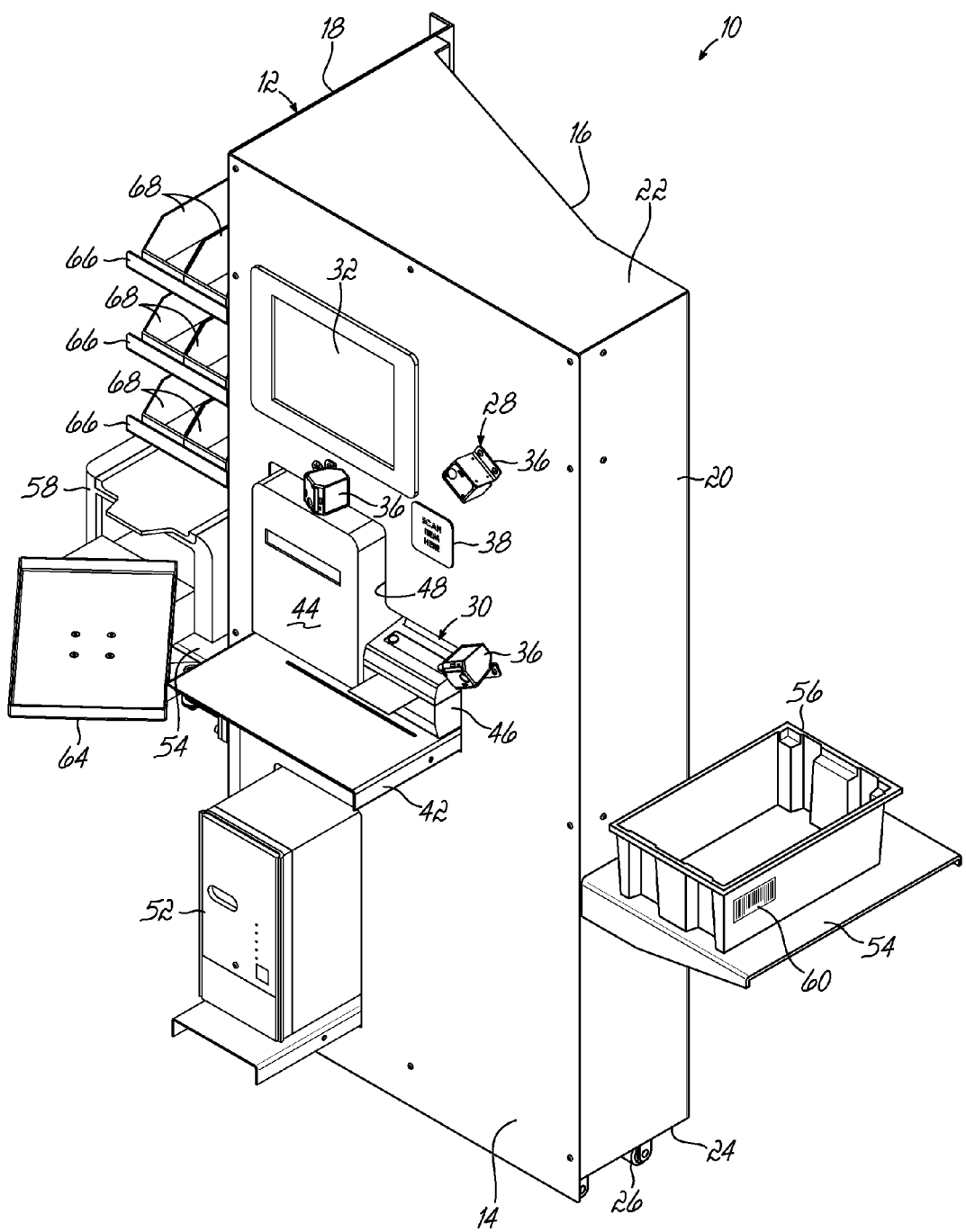
FIG. 1 is a perspective view of a label and verification kiosk (LVK) according to one exemplary embodiment of the invention.

Embodiments consistent with aspects of the current invention provide for a system, apparatus and method for filling a customer order with a plurality of products, where each product includes a medical item. An operator may utilize a label and verification (LV) kiosk (or LVK) to label products with patient labels (which may include a flag label) corresponding to the customer order and verify that the correct product includes the correct patient label by scanning a product label having a barcode indicating a particular product and a patient barcode indicating a particular patient and included on the patient label. The LVK generally includes at least one processor and a memory. In addition, the LVK may be in communication with at least one barcode scanner and at least one printer, such that the LVK may receive barcode data from the at least one barcode scanner and output print data to the at least one printer. In this regard, the LVK is operable to print patient labels on demand and flag labels only as these labels are required.

Consistent with embodiments of the invention, an operator may scan a medical item with a barcode scanner associated with the pharmacy filling LVK. The LVK may verify that the product corresponds to an active order, and in response to verifying that the medical item corresponds to the active order, the LVK may output patient label data, including a patient label barcode, to a printer in communication with the LVK, such that the printer prints a patient label including a patient label barcode based on the patient label data. If a flag label is required for the scanned medical item, upon initiation, further label information is sent to a flag label printer as well. The flag label is a smaller label with compressed label content that contains the patient name and other identification information such as medication product, dosage form, strength, and quantity to be placed on the medical item within the outer packaging, while the "patient label" is the larger label with comprehensive information to be placed on the outer packaging. If using a flag label, the operator may apply the flag label to a given item that cannot be labeled with the larger patient label. If there are more components to the order that require this flag label, the operator will be prompted and/or will be able to request additional flag labels while the patient order is active and before the labeling of the product has been verified. For example, if this is an inhaler, the operator will remove the inhaler from the manufacturer's carton and apply the flag label to the inhaler and the patient label to the carton. Another example would be if the order consisted of five 20 ml vials, each of the vials would be labeled with a flag label and the group of five would be packaged with a bag or a carton and the resulting bag or carton will receive the patient label. In short, the outer most packaging receives the patient label, and the inner most package receives the flag label. The operator may apply the patient label to the product, and then scan both the product barcode on the product label and the patient barcode on the patient label with the barcode scanner. The LVK may verify that the patient label is affixed to the correct product. In response to verifying that the patient label is affixed to the correct product, the LVK may output a confirmation to the operator on a display screen associated with the LVK. Following verification, the operator may place the labeled and verified product in a container associated with the active order.

In some embodiments consistent with the invention, the medical items are collected into a tote using the conventional pick ticket method of manually retrieving inventory from bulk inventory locations. Based on the execution of a variety of sort rules and algorithms, pick tickets are generated and printed for operators to take a tote associated with a customer order and collect all of the inventory items to be placed in that tote, whether done using a pick-to-light system or a non-pick-to-light system. The items are placed in the tote, which is referred to as a raw material in progress or RIP tote, and then taken to a staging area where the tote is positioned until use at the LVK. The staging of the RIP tote informs the system that the items within the tote are ready for processing via labeling and verification at the LVK. The LVK can then request a particular staged RIP tote for another operator to retrieve from staging for use as described above and in further detail below.

In other embodiments consistent with the invention, the LVK may be incorporated with a universal labeling and verification (ULV) system that includes a product storage subsystem, which stores a plurality of products in a plurality of storage locations. In these embodiments, the LVK may receive order data corresponding to an order to be filled by an operator at the LVK, and the LVK may indicate one or more products for the operator to retrieve from the product storage subsystem based on the received order data. In some embodiments, the LVK may indicate one or more products for the operator to retrieve by outputting identification and quantity data for a particular product to a display in communication with the LVK. In some embodiments, the LVK may interface with pick to light logic and hardware to selectively operate pick modules, where the selectively operated pick modules may indicate to the operator a particular storage location from which a product should be retrieved and the number of items from that storage location to be retrieved and processed. Furthermore, in some embodiments, the product storage subsystem may include at least one ULV carousel unit having the LVK and a rotatable storage carousel including a plurality of storage levels, where each storage level includes a plurality of storage locations. In these embodiments, the LVK may interface with at least one carousel drive controller to thereby rotate the storage carousel(s) and position a storage location storing a product required for the order in a pick location accessible by the operator.

Consequently, the LVK and ULV system enable on demand printing and application of patient labels for many types of products and medical items that are not contained within blister cards and product boxes. Thus, only one label (the correct patient label) is generated and applied to the product currently held by an operator. Additionally, the products may be collected into batches before presentation at the LVK, which reduces the number of sorting operations required after the labeling and verification process. Moreover, the practices of carrying around a batch of labels and printing flag labels for all patient labels whether necessary or not are eliminated to reduce waste of label material (and the associated costs of incinerating or otherwise disposing of private patient information) and to reduce the likelihood for errors when applying patient labels to products. The LVK and ULV system extend the benefits of the automated label and verification system to a significantly higher percentage of products filled by a pharmacy, as many types of product packaging beyond the blister cards and product boxes can be labeled and verified using this system.

With reference to FIGS. 1 through 4, an exemplary embodiment of a label and verification kiosk (LVK) 10 according to the current invention is shown in further detail. The LVK 10 includes a housing 12 having a generally box-shaped configuration including a front wall 14 and a rear wall 16 connected by corresponding first and second sidewalls 18, 20 and corresponding top and bottom walls 22, 24. The rear wall 16 is shown having an angled or contoured profile in FIG. 1 that is advantageous when the LVK 10 is used with a ULV carousel unit described in further detail with reference to FIG. 6 below, although it will be understood that the rear wall 16 may be modified to be generally parallel to the front wall 14 in other standalone embodiments of the LVK 10. The bottom wall 24 may include caster wheels 26 as shown in FIG. 1 to assist with movement and placement of the LVK 10, although the LVK 10 will generally be fastened fixedly to a floor or some other structure during active use. The housing 12 is sized to contain and mount a plurality of elements required for scanning and labeling medical items and products. These elements include a barcode scanner assembly 28, a label printing station 30, and a touch screen display 32 configured to provide instructions and receive input from an operator at the LVK 10. Accordingly, the specific size and shape of the housing 12 and the layout of these elements 28, 30, 32 required for scanning and labeling may be modified in other embodiments without departing from the scope of the embodiments of the invention.

With continued reference to FIGS. 1 through 4, the elements 28, 30, 32 requiring for scanning and labeling at the LVK 10 are shown in further detail. To this end, the barcode scanner assembly 28 includes a plurality of barcode scanners 36 centered around a scanning indicia plate 38 on the front wall 14 of the housing 12. More specifically, the LVK 10 of the illustrated embodiment includes three barcode scanners 36 equally spaced radially around the scanning indicia plate 38. This arrangement of barcode scanners 36 provides accurate readings of barcodes inserted in any orientation into a scan area 40, schematically illustrated in FIG. 2 adjacent to the scanning indicia plate 38. As a result, the operator does not need to hold each product and label in a particular orientation to get an accurate scan; the only requirement is to position the label within the scan area 40 at the scanning indicia plate 38. The scanning indicia plate 38 may include printed text reading "SCAN ITEM HERE" or some other analogous message or labeling so that the operator knows where to position the product at the barcode scanner assembly 28. The number of barcode scanners 36 and the particular layout of the scan area 40 may be modified in other embodiments of the LVK 10. For example, in another exemplary embodiment of the invention (not illustrated), the barcode scanner assembly 28 may only require one barcode scanner instead of three.

The label printing station 30 is located along the front wall 14 of the housing 12 and generally immediately below the barcode scanner assembly 28. To this end, the label printing station 30 includes a work shelf 42 projecting outwardly in general horizontal orientation from the front wall 14. The work shelf 42 is preferably sized just large enough for an operator to work with a single product or medical item at a time at the label printing station 30, thereby discouraging deviations from the process of labeling and verification of each medical item individually as described in detail below. The label printing station 30 also includes a patient label printer 44 and a flag label printer 46 supported on the work shelf 42 and positioned almost entirely within an interior of the housing 12. The front wall 14 of the housing 12 includes a shaped aperture 48 located at and above the work shelf 42 to provide access to the patient label printer 44 and the flag label printer 46. As will be readily understood, the patient label printer 44 is operable to print a patient label with a patient barcode, and the flag label printer 46 is operable to print a flag label with a patient barcode for products that require such flag labels. Additionally, these two printers 44, 46 could be replaced with a single printer operative to print both types of labels in other embodiments of the LVK 10.

Figure 2:
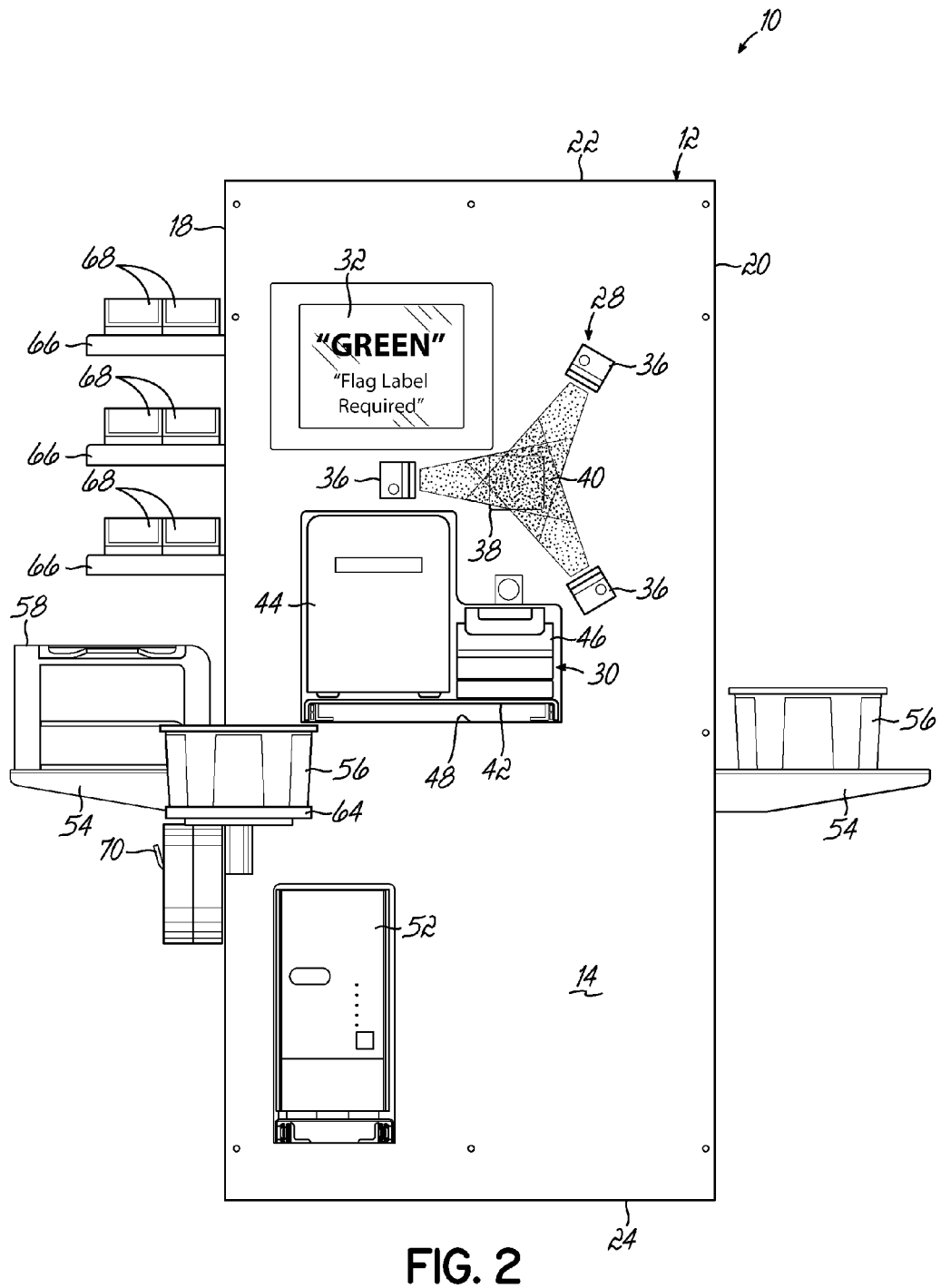
FIG. 2 is a front view of the LVK of FIG. 1, illustrating the scanning fields for the LVK and a message provided on a touch screen display.
Figure 3A:
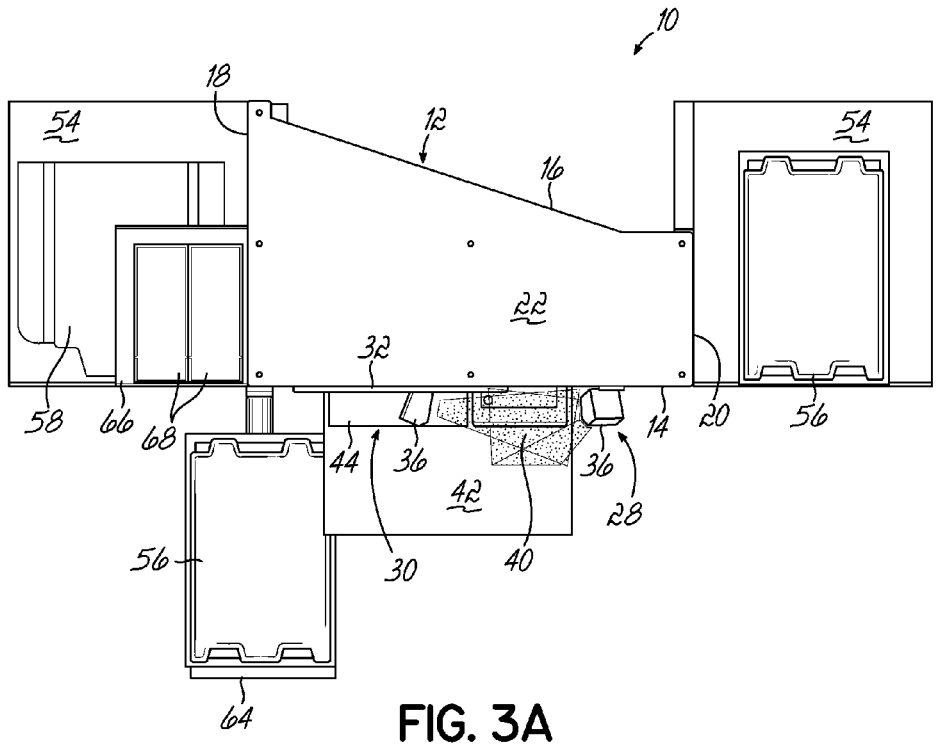
FIG. 3A is a top view of the LVK of FIG. 1, showing an articulating shelf in an extended position.
Figure 3B:
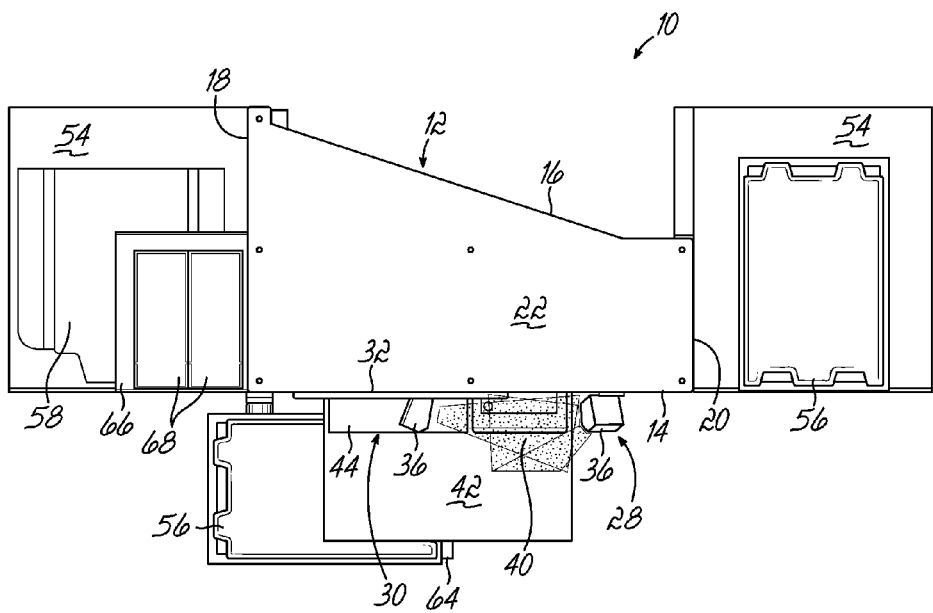
FIG. 3B is a top view of the LVK of FIG. 3A, showing the articulating shelf in a stowed position.

The touch screen display 32 is located along the front wall 14 of the housing 12 and generally, immediately above the barcode scanner assembly 28. As shown in FIG. 2, the barcode scanner assembly 28 may be positioned slightly to the right of the touch screen display 32 such that the touch screen display 32 is only separated from the patient label printer 44 by one of the barcode scanners 36. The touch screen display 32 is configured to provide messages to and receive input from the operator at the LVK 10. The touch screen display 32 is operatively connected to the barcode scanner assembly 28 and the label printing station 30 such that the display 32 can provide accurate information regarding the packaging, labeling and verification process carried out using these other elements 28, 30. To this end, the LVK 10 includes a computer 52 which may be in communication with the barcode scanners 36, the printers 44, 46, and the display 32. The computer 52 is recessed mostly within the housing 12 similar to the printers 44, 46 and is accessible through an opening at the front wall 14, as shown in FIG. 2. The positioning of the computer 52 may be modified in other embodiments of the LVK 10 (e.g., the opening may be in the first sidewall 18), as regular access to the computer 52 will not be necessary during operation of the LVK 10. Additionally, while FIGS. 1 and 2 illustrate a computer 52 associated with the housing 12, the invention is not so limited. For example, in some embodiments, components typically associated with a computer 52, such as a processor/controller, an I/O interface, a memory, a human machine interface (HMI) (e.g., a keyboard, mouse, display screen, touch screen, microphone, speakers, etc.) may be enclosed in the housing 12 and not necessarily further enclosed in a computer housing. In one alternative, all of these elements may be incorporated into the touch screen display 32. Regardless, the computer 52 provides local control and communication among the elements 28, 30, 32 required for scanning and labeling medical items at the LVK 10.

With continued reference to FIGS. 1 through 4, the LVK 10 may also include stationary shelves 54 coupled to one or both of the first and second sidewalls 18, 20. The stationary shelves 54 are configured to receive medical item and product containers such as totes 56 or additional elements such as a document printer 58. To this end, the stationary shelf 54 located along the second sidewall 20 in the illustrated embodiment is supporting a tote 56 that may include a batch of medical items already pulled from bulk inventory locations and ready for scanning and labeling at the LVK 10. Each tote 56 includes a tote barcode 60 that may be used to associate the group of medical items and products held within the tote 56 to a particular batch. The stationary shelf 54 located along the first sidewall 18 in the illustrated embodiment is supporting the document printer 58, which is operatively connected to the computer 52 and configured to print out paper documents (such as pick tickets used to gather items) when required by the operator using the LVK 10. It will be understood that the document printer 58 may be relocated to be recessed mostly within the interior of the housing 12 in other embodiments of the LVK 10, which would free up space on the stationary shelf 54 to hold a tote 56 or another item.

The LVK 10 also includes one or more articulating shelves 64 configured to hold totes 56 in a convenient location adjacent to the work shelf 42. In the illustrated embodiment of FIGS. 1 through 4, the LVK 10 includes one articulating shelf 64 coupled to the front wall 14 of the housing 12 adjacent the first sidewall 18. The articulating shelf 64 is pivotally moveable between an extended position shown in FIG. 3A to a stowed position shown in FIG. 3B. The articulating shelf 64 can therefore be moved to the extended position of FIG. 3A to provide an adjacent storage location for a tote 56 receiving medical items scanned and labeled at the work shelf 42. When the LVK 10 is not in active use or when the stationary shelf 54 along the first sidewall 18 holds a tote 56 for receiving medical items scanned and labeled at the work shelf 42, the articulating shelf 64 is moved from the extended position to the stowed position of FIG. 3B to keep the articulating shelf 64 out of the way of the operator. Similar to the stationary shelves 54, it will be understood that the particular number and positioning of articulating shelves 64 used with the LVK 10 may be modified in other embodiments of the invention.

As shown in this embodiment, the LVK 10 also includes a plurality of bin shelves 66 projecting in a horizontal orientation outwardly from the first sidewall 18 and located above the stationary shelf 54, generally at the same level as the barcode scanner assembly 28 and the display 32. The bin shelves 66 receive a plurality of bins 68 that may store different types of tape, labels, bags, and/or other such packaging materials that may be utilized in filling a customer order at the LVK 10. For example, in some embodiments, the LVK 10 may output on the display 32 instructions that direct an operator to place a product in a particular sized bag stored in a particular bin 68 during the scanning and labeling process before placing the labeled product in a tote 56 associated with the customer order. These instructions may be in the form of lines of textual information, colors, or symbols, and combinations of each. To this end, each of the bins 68 may be a different color or may include a symbol or other indicia differentiating the bins 68 so that the display 32 can readily identify the bin 68 holding the correctly sized bag for the product. In FIG. 2, this identification is schematically shown as the illustration of a color on the display 32 corresponding to the bin 68 where a bag or some other packaging material for the product is located. The plurality of bin shelves 66 enables the storage and ready retrieval of the additional packaging materials such as bags that may be needed by the operator for the various types of medical items and products labeled and verified at the LVK 10. Additional packaging materials or extra rolls of label material to be printed upon may be stored on at least one hook-shaped holder 70 located along the first sidewall 18 of the housing 12 below the stationary shelf 54. It will be appreciated that different numbers of bin shelves 66 and hook-shaped holders 70 may be used in other embodiments of the LVK 10.

Figure 4:
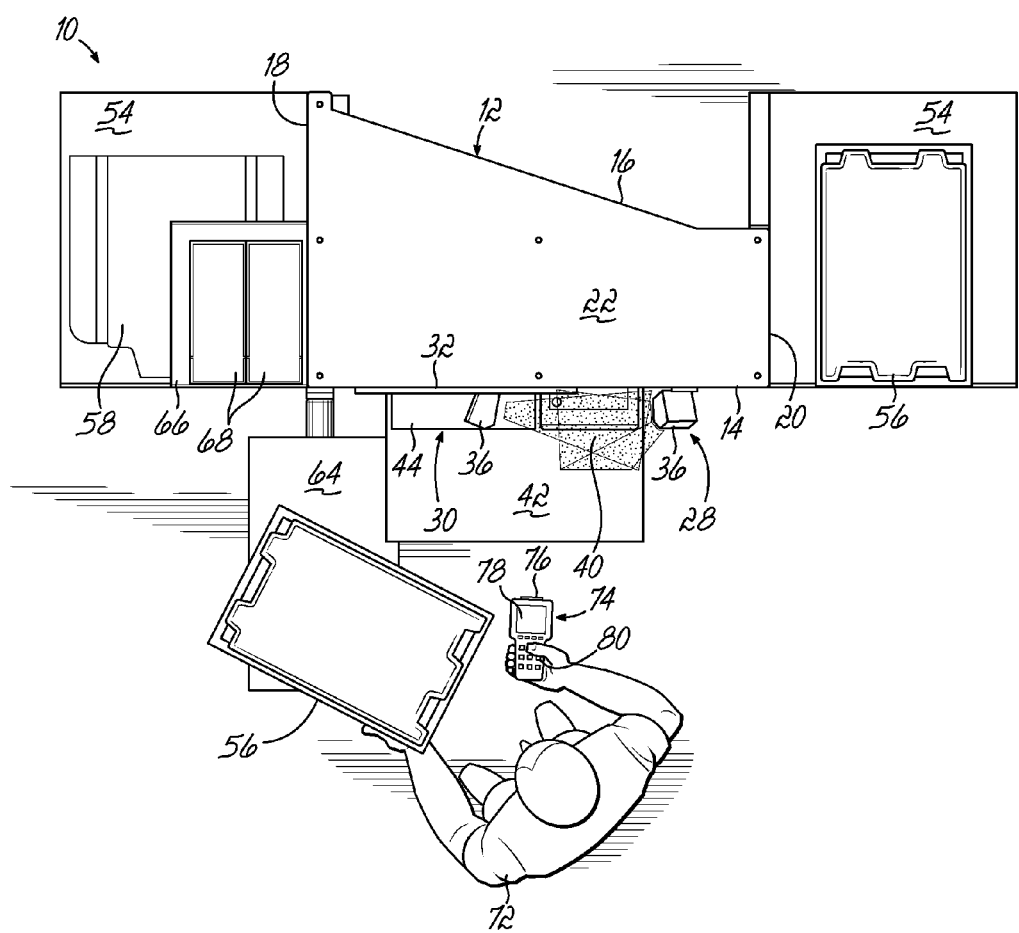
FIG. 4 is a top view of the LVK of FIG. 1 with an operator handling a tote and a hand scanner at the LVK.

With reference to FIG. 4, an operator 72 is shown working near the LVK 10. The operator 72 is holding a tote 56 in one hand and a manual scanner 74 in the other hand. As described in further detail below, the manual scanner 74 is a handheld barcode scanner that may be used during collection of the batches of medical items and products from bulk inventory to be placed in the corresponding totes 56 (e.g., during the initial collection of medical items and staging of the totes 56 in a staging area proximate to the LVK 10). The manual scanner 74 includes a barcode scanner 76 on a free end and a small display screen 78 and keypad 80 on the top side. The operator 72 uses the barcode scanner 76 to scan totes 56 and product labels on medical items pulled from bulk inventory locations, whether performed by pick-to-light storage locations or non-pick-to-light (NPTL) storage locations. Once the batch has been picked and placed within the tote 56, the tote 56 may be placed at the staging area and then at the LVK 10 (such as on the stationary shelf 54 on the second sidewall 20) when ready for order processing as described below, and the process of scanning and labeling the batch of medical items can begin. Therefore, the LVK 10 may be used for all different types of inventory storage locations, including in smaller facilities that are not large enough to include the automated labeling and verification hardware described briefly above. It will be understood that at least one operator 72 may work with the manual scanner 74 to collect batches of medical items and products into totes 56 for another at least one operator 72 to work with at the LVK(s) 10. To this end, the operator 72 preparing totes 56 for use at the LVK 10 will use the manual scanner 74 to verify the use of the tote 56 and the products pulled from bulk inventory so that the order control module of the LVK 10 knows which products to expect during the later process after staging. The manual scanner 74 may also be used during replenishment of a storage carousel connected to the LVK 10, but the scanner assembly 28 on the LVK 10 is used during the actual labeling and verification process rather than the manual scanner 74.

Once a tote 56 with a batch of medical items is located in a staging area, the LVK 10 can identify that tote 56 for retrieval from the staging area and placement at the LVK 10. The operator 72 begins a scanning and labeling process for each medical item by scanning with the scanner assembly 28 the RIP tote 56 that has been staged and includes the plurality of medical items for the customer order. An empty tote 56 that is to receive medical items following labeling and verification is then scanned at the scanner assembly 28 in order to assign this tote 56 to the current order. These totes may be referred to as a work in process (WIP) tote or shipping (SHP) tote if the items sorted into the RIP tote 56 were sorted by a single facility, and these totes may be referred to as an aisle (ASL) tote if the medical items in the RIP tote 56 are sorted to be associated with multiple facilities. Following these scans of the RIP tote 56 and the tote for receiving labeled items, the process of individually labeling the items can continue as follows.

The operator 72 picks up the first item from the tote 56 (e.g., the RIP tote) on the stationary shelf 54 and scans the product label with the barcode scanner assembly 28, which prompts the printing of a patient label at the patient label printer 44. If a flag label is required or some other secondary packaging such as bagging is required, the display 32 will indicate as such, and the operator 72 can prompt/command the LVK 10 at the display 32 to print at least one flag label at the flag label printer 46. The operator 72 then applies the flag label(s) (if required) and the patient label to the product and scans the patient label and product label again at the barcode scanner assembly 28. Assuming that these labels are verified by this scan, the display 32 will prompt the operator 72 to place the labeled product in another tote 56 (e.g., the WIP, SHP, or ASL tote) at the articulating shelf 64. The operator 72 can repeat this process for each item in the tote 56 until all items in the batch are labeled with patient labels and verified to be labeled correctly. The filled tote 56 on the articulating shelf 64 can then be moved to downstream processing and the empty tote 56 on the stationary shelf 54 can be reused or moved to the articulating shelf 64 for use with the next batch (once all the items previously assigned to the RIP tote are reconciled—scanned, labeled and verified or canceled) at the LVK 10. Advantageously, the accurately pre-sorted totes of medical items can be scanned and handled on a tote-by-tote basis downstream of the labeling and verification process rather than requiring sorting into separate shipping bags for different customer orders during downstream processing.

If the mode of operation is for WIP totes, a WIP tote is dynamically associated to a facility or shipping delivery point. If the work in process tote is used to transport thirty items to the actual shipping container, the act of scanning the WIP tote to the shipping container barcode "transfers" the logical contents of the WIP tote to the shipping container and the operator then deposits the contents from the WIP tote physically into the shipping container. Once this act is complete, the WIP tote status is then changed from assigned to free and it can be reassigned to another facility. If the mode of operation is for ASL totes, there are multiple facilities contained within the ASL tote. Therefore, each individual item will need to be scanned into the shipping container downstream of the process at the LVK. Not until all the physical (and logical) items are transferred from the ASL tote to the shipping tote or container will the ASL tote status be changed from assigned to free so it can be reassigned to another batch and/or group of facilities. Lastly, the system could process directly into shipping containers or totes where no further scanning is required after the labeled and verified items are placed into the totes.

Thus, an entire pre-sorted batch of medical items for a single customer order can be labeled with patient labels and verified all at once, regardless of the specific type of packaging used to store the medical items, thereby enabling labeling on demand and fewer human touches required to sort the labeled medical items during downstream processing of the customer order. This process can improve the number of medical items labeled and verified over a traditional manual process from 1 every 1 to 3 minutes to between about 4-6 products per minute depending on any necessary packing or late stage customization that may be required. Advantageously, the LVK 10 may be implemented with any type of bulk inventory and batch creation hardware, including pick-to-light storage locations and NPTL storage locations. The control functions for operating the LVK 10 according to this brief description of a labeling and verification process is described in further detail below.

Now turning to FIGS. 5 through 11, a universal labeling and verification (ULV) system 100 according to another exemplary embodiment of the invention is shown in detail. As shown generally in the top plan view of FIG. 5, the ULV system 100 includes a plurality of ULV carousel units 102 each including a LVK 104 and a cage 106 surrounding a moveable storage carousel 108. The LVK 104 is similar to the first embodiment of the LVK 10 described with reference to FIGS. 1 through 4 above. However, as described in detail with reference to FIG. 11 below, the LVK 104 of this embodiment includes additional elements configured to interact with the levels of the storage carousel 108 and instruct the operator 72 where to retrieve medical items or products from in the storage carousel 108. The cage 106 in combination with the LVK 104 selectively provides access to only a small portion (referred to herein as a "pick location" or "vertical storage column 165") of the storage carousel 108. The storage carousels 108 include a plurality of storage locations that may be rotated into position for access by the operator 72 and are described in further detail with reference to FIGS. 8 through 9B below. As a result, the storage carousels 108 effectively move a plurality of medical items and products to the LVKs 104 for scanning and labeling with patient labels, rather than requiring an operator 72 to walk up and down aisles of storage racks of bulk inventory to collect batches of medical items and products. In addition, it will be understood that the LVK 104 of this embodiment may be used with different numbers of storage carousels 108 and different types of inventory locations, such as the pick-to-light racks 109 shown in FIG. 5. In such embodiments, the operator will move between the storage carousels 108 and the pick-to-light racks 109 (which normally carry bulkier medical items that move in high quantities) as prompted in order to collect all of the medical items for a given customer order. The LVK 104 may also be an independent kiosk mounted on wheels so as to be repositioned in any convenient location near specific storage carousels 108, pick-to-light racks 109, or other types of storage racks that may not use pick-to-light technology. Consequently, the products can be arranged neat the LVK 104 or the LVK 104 may be arranged near the products in various embodiments of the invention.

Figure 5:
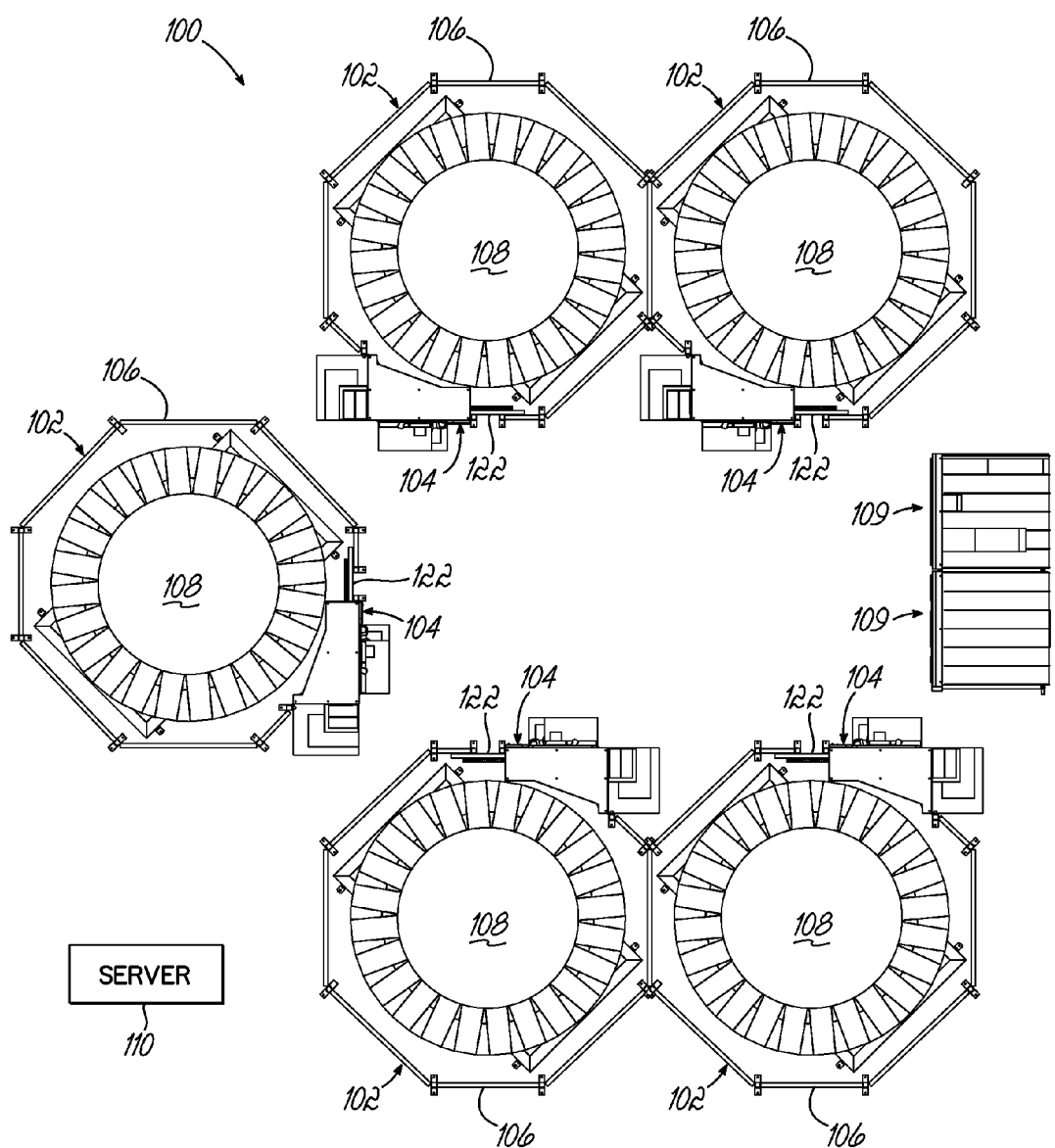
FIG. 5 is a top schematic plan view of a universal labeling and verification (ULV) system including five ULV carousel units according to another exemplary embodiment of the invention.
Figure 5A:
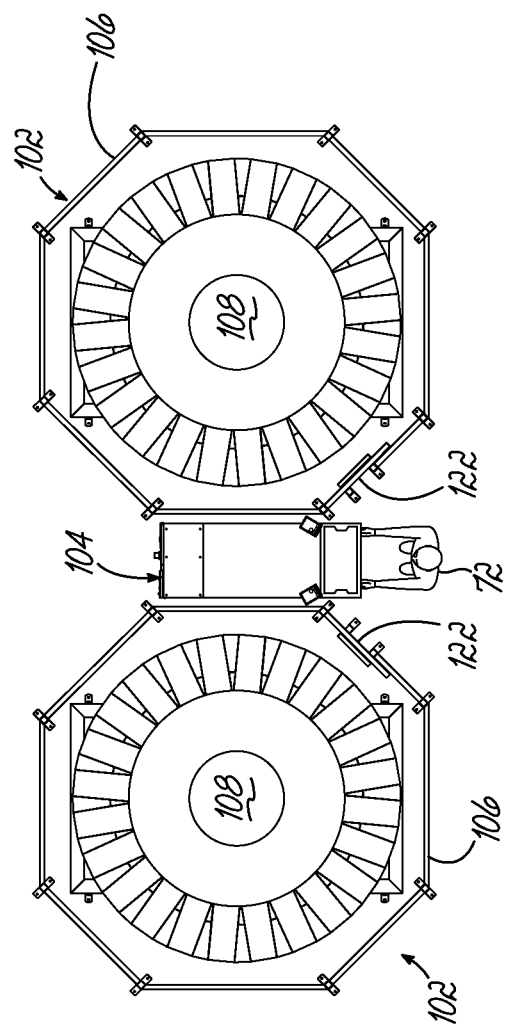
FIG. 5A is a top schematic plan view of an alternative universal label and verification system including two ULV carousel units connected to a shared LV kiosk.

With brief reference to FIG. 5A, one of these alternatives within the scope of the invention is shown in further detail. More specifically, one LVK 104 is mounted between two storage carousels 108. The operator working at this LVK 104 still remains within reach of the doors and openings into each of the storage carousels 108 through the corresponding cages 106. Therefore, the total number of medical items that the operator has access to without moving a substantial distance doubles compared to the exemplary embodiment described in further detail in the following paragraphs. Regardless of the type and number of storage racks and carousels that may be used with a single LVK 104 or group of LVK's 104, the primary operation of manually retrieving, labeling, and scanning to verify the correct medical items are placed in the customer order remains largely the same in all embodiments. Accordingly, each embodiment possible under the scope of the invention achieves the advantageous benefits of increasing the number of types of containers and items that can be labeled and verified while also improving the efficiency of the manual labeling and verification process significantly.

Furthermore, when using a ULV system 100 including a series of ULV carousel units 102 (five shown in FIG. 5), an operator 72 has access to over 2000 distinct medical items and products for use in forming pre-sorted batches to pick, label and verify. The inventory stored in all of the storage carousels 108 is monitored and managed by communication between the computers 52 on the LVKs 104 and a pharmacy host server 110 shown schematically in FIG. 5. The server 110 may also communicate with a central control station (not shown) that allows a pharmacist to log in to activate and monitor the labeling and verification process carried out at the individual ULV carousel units 102. It will be understood that while five ULV carousel units 102 are shown in the ULV system 100 of the exemplary embodiment, more or fewer ULV carousel units 102 may be used depending on the volume and number of medical items and products needed for a typical day of prescription filling at the pharmacy. Additionally, the layout of ULV carousel units 102 is shown with the LVKs 104 facing generally towards one another to minimize the steps needed to move totes 56 between the LVKs 104, but this layout may be modified in other embodiments consistent with the invention.

Figure 6:
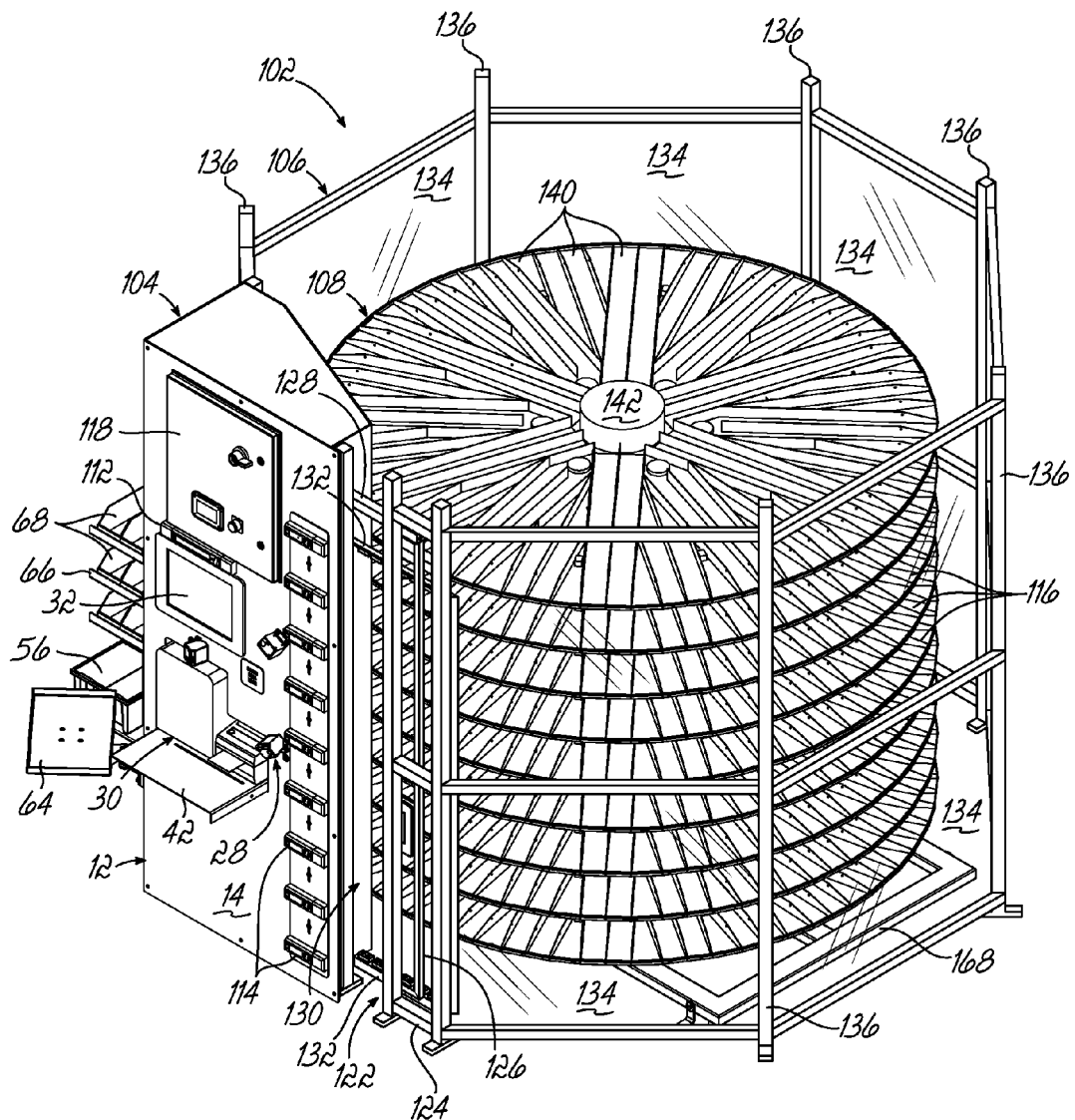
FIG. 6 is a perspective view of one of the ULV carousel units of FIG. 5, the ULV carousel unit including an LVK and a cage surrounding a storage carousel.
Figure 7:
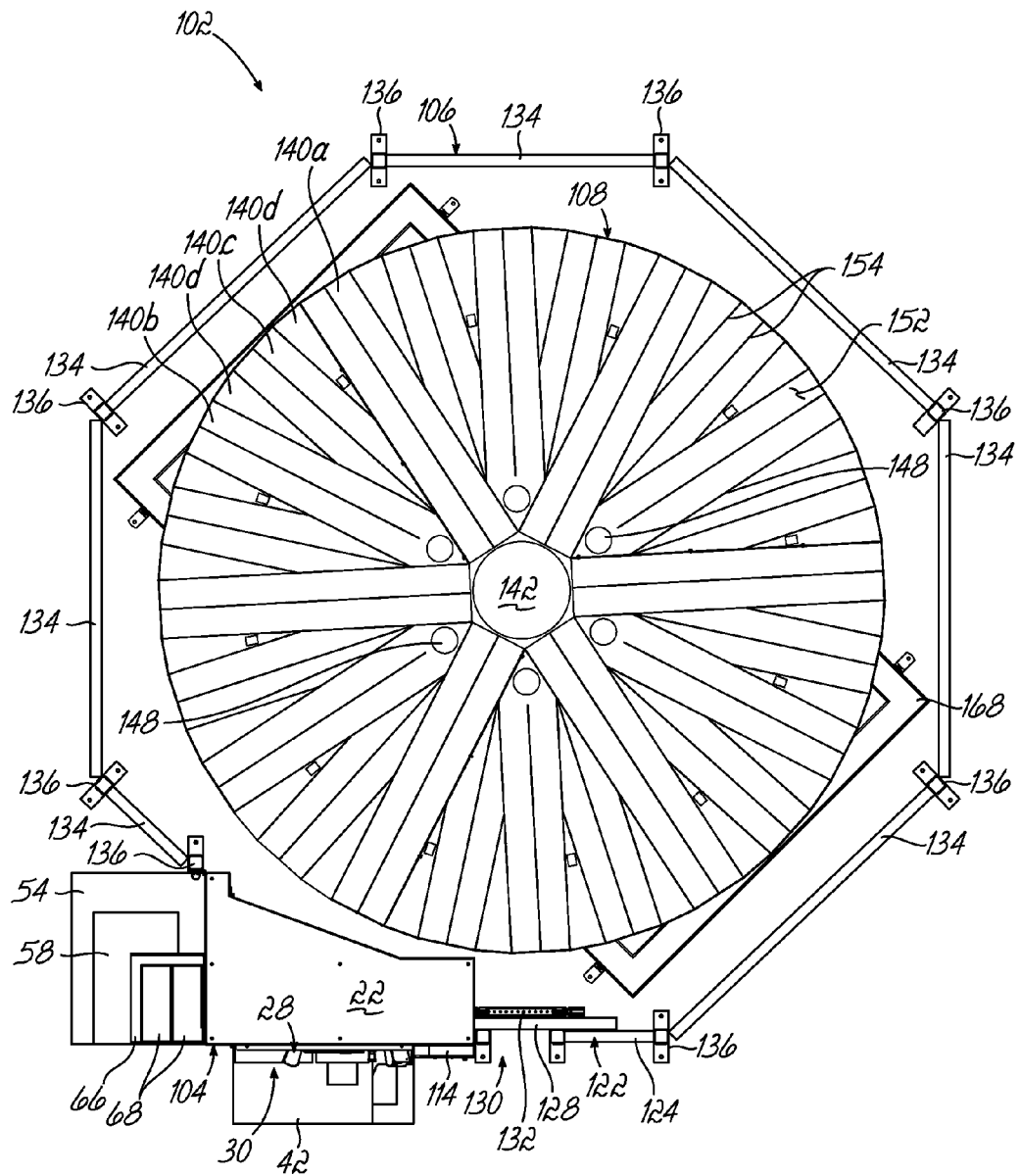
FIG. 7 is a top view of the ULV carousel unit of FIG. 6.

With reference to FIGS. 6 and 7, one of the ULV carousel units 102 is illustrated in further detail. As briefly described above, the LVK 104 used with the ULV carousel unit 102 is slightly modified from the kiosk 10 described above, and the same reference numbers have been used on elements that remain the same from the previous embodiment without further detailed description herein. In addition to those elements previously described (such as the barcode scanner assembly 28, the label printing station 30, and the touch screen display 32), the LVK 104 includes an order control module 112 and a light tree with a plurality of pick modules 114 on the front wall 14 of the housing 12. The order control module 112 includes a 12-character alphanumeric display located just below the touch screen display 32 and is configured to display information about a batch being currently operated on by the ULV system 100. The pick modules 114 are positioned generally at the height of each shelf 116 on the storage carousel 108 and include a four-character alphanumeric display configured to show a number of items to be picked from the particular storage location at the corresponding shelf 116. The order control module 112 and the pick modules 114 are connected to a controller (referred to herein as pick indicator logic) (not shown) located in the housing 12 and configured to communicate with the computer 52. The LVK 104 is also taller in height to match the height of the storage carousel 108. This additional height enables the positioning of an electrical control box 118 above the touch screen display 32. The electrical control box 118 includes the operating controls for the storage carousel 108 and for the elements associated with the cage 106. As a result, the LVK 104 serves as a control base for the entire ULV carousel unit 102.

The cage 106 includes a door 122 located adjacent to and extending from the second sidewall 20 of the LVK 104. The door 122 includes a stationary door panel 124 connected to the remainder of the cage 106 and a moveable door panel 126 slideably mounted on rails 128 on the stationary door panel 124. The door 122 may be manually moved or motorized in various embodiments of the invention. When the moveable door panel 126 moves to an open position behind the stationary door panel 124, a tall elongate opening (also referred to as the pick location) 130 is formed in the cage 106 providing access to the storage carousel 108 from outside the cage 106. Adjacent to this opening 130 is provided a light curtain optical sensor 132 that operates to detect any entries of an operator's arm into the ULV carousel unit 102 from outside the cage 106. These elements of the door 122 are shown in further detail with reference to FIG. 10 below. The remainder of the cage 106 is defined by a plurality of cage panels 134 connected in series to form a roughly octagonal shaped enclosure to surround the storage carousel 108. The cage panels 134 define corner joints 136 that may be connected to adjacent cage panels 134 and secured to the floor to prevent unintentional removal of the cage 106 from the storage carousel 108. In FIG. 6 and other figures, the cage panels 134 are shown with a clear Plexiglas-type appearance for illustrative purposes, but the exemplary embodiment of the cage panels 134 includes metal wire mesh caging that blocks unintended entry into the ULV carousel unit 102. However, alternative types of blocking cage panels 134 such as Plexiglas, aluminum, or light grade steel panels may be used in other embodiments of the ULV carousel unit 102.

Figure 8:
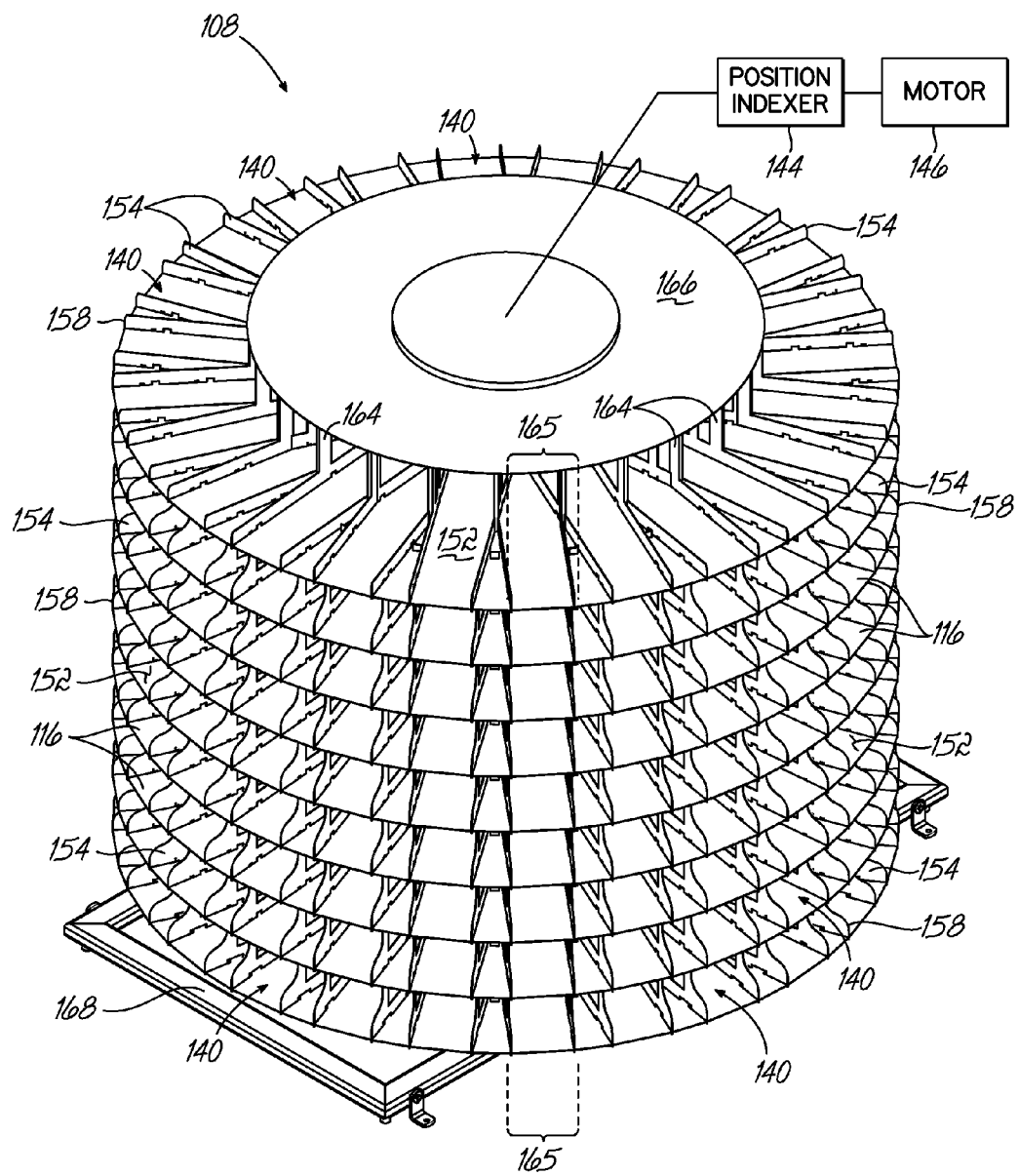
FIG. 8 is a perspective view of the storage carousel used with the ULV carousel unit of FIG. 6.

As described briefly above, the storage carousel 108 includes a plurality of shelves 116 defining a plurality of radially-oriented storage bins 140 (also referred to as storage locations) extending outwardly from a central shaft 142. The storage bins 140 are sized with a width corresponding closely to the size of standard medical item product boxes, which generally have a width of about 7 inches across. However, the overall arrangement of the bins 140 and the size of the bins 140 and the distance between the shelves 116 may be increased or decreased to increase or decrease the total amount of storage locations. The opening 130 through the door 122 is also sized slightly larger than the size of these storage bins 140 such that access is only provided to the storage bins 140 directly facing the opening 130 when the operator 72 reaches into the ULV carousel unit 102. As a result, the storage carousel 108 must be indexed during rotation to ensure that the intended set of storage bins 140 on the shelves 116 are appropriately aligned with the opening 130. With reference to FIG. 8, the storage carousel 108 includes a position indexer 144 and a motor 146 operatively coupled to the central shaft 142 to drive indexed rotation of the storage carousel 108. As shown most clearly in FIGS. 7 and 9A, the storage carousel 108 also includes a plurality of alignment shafts 148 that extend through the shelves 116 and are also driven by the motor 146. The central shaft 142 and the alignment shafts 148 provide reliable support and rotation driving power to each of the nine shelves 116 shown in the exemplary embodiment, even when all of the storage bins 140 are loaded with medical items and products. In the exemplary embodiment, the motor 146 is operable to rotate the storage carousel 108 with a controlled movement of 180 degrees in less than 2.5 seconds. This rapid rotation enables the storage carousel 108 to always be located at the next location by the time the operator 72 returns to the opening 130 following the labeling and verification of a previous medical item. However, the rotation is not so rapid as to cause the medical items on the storage carousel 108 to be forced off the shelves 116 by centrifugal force (e.g., the rotation is controlled via acceleration and deceleration curves and control algorithms).

Figure 9A:
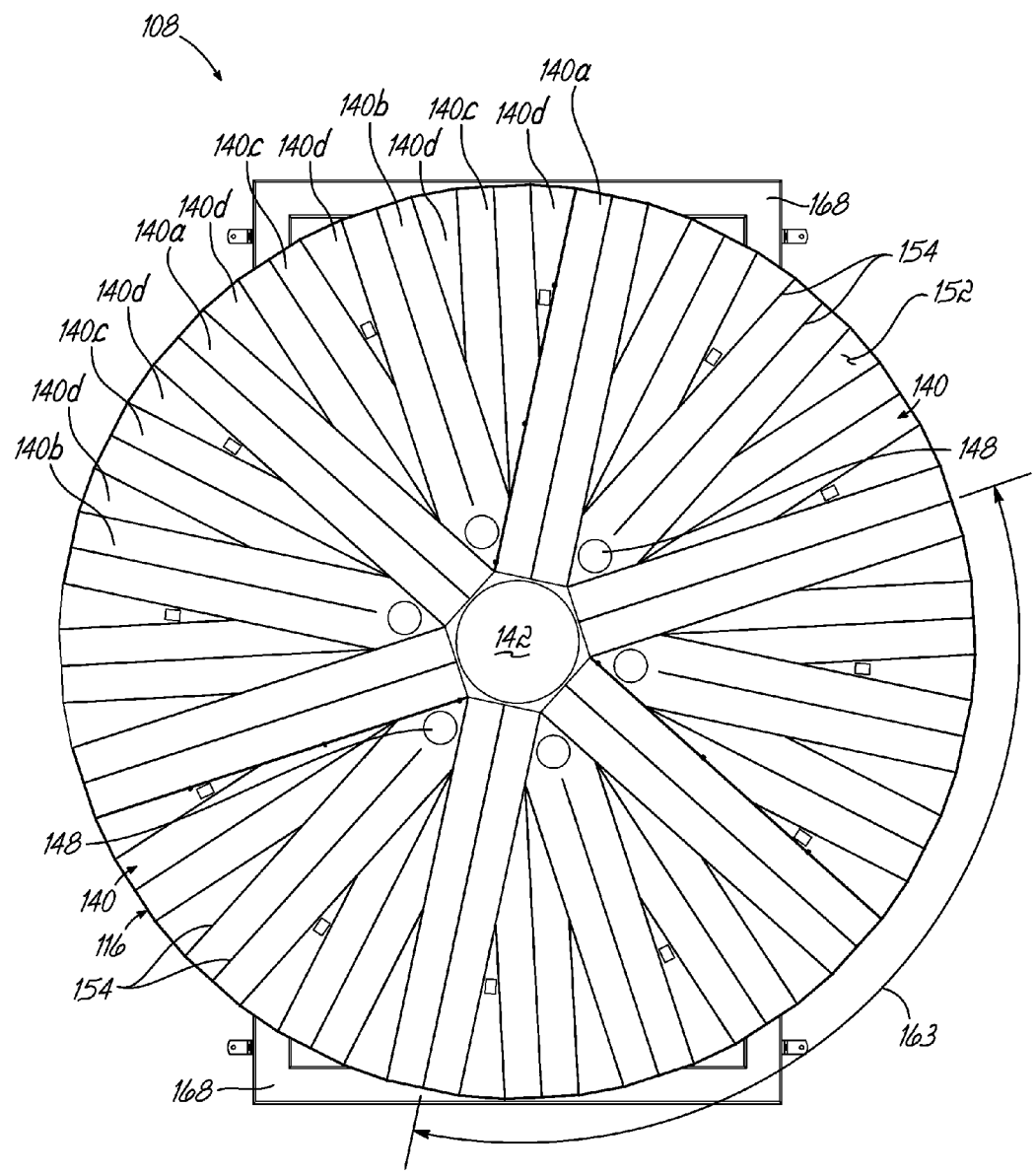
FIG. 9A is a top view of the storage carousel of FIG. 8, illustrating an exemplary layout of one of the shelves.
Figure 9B:
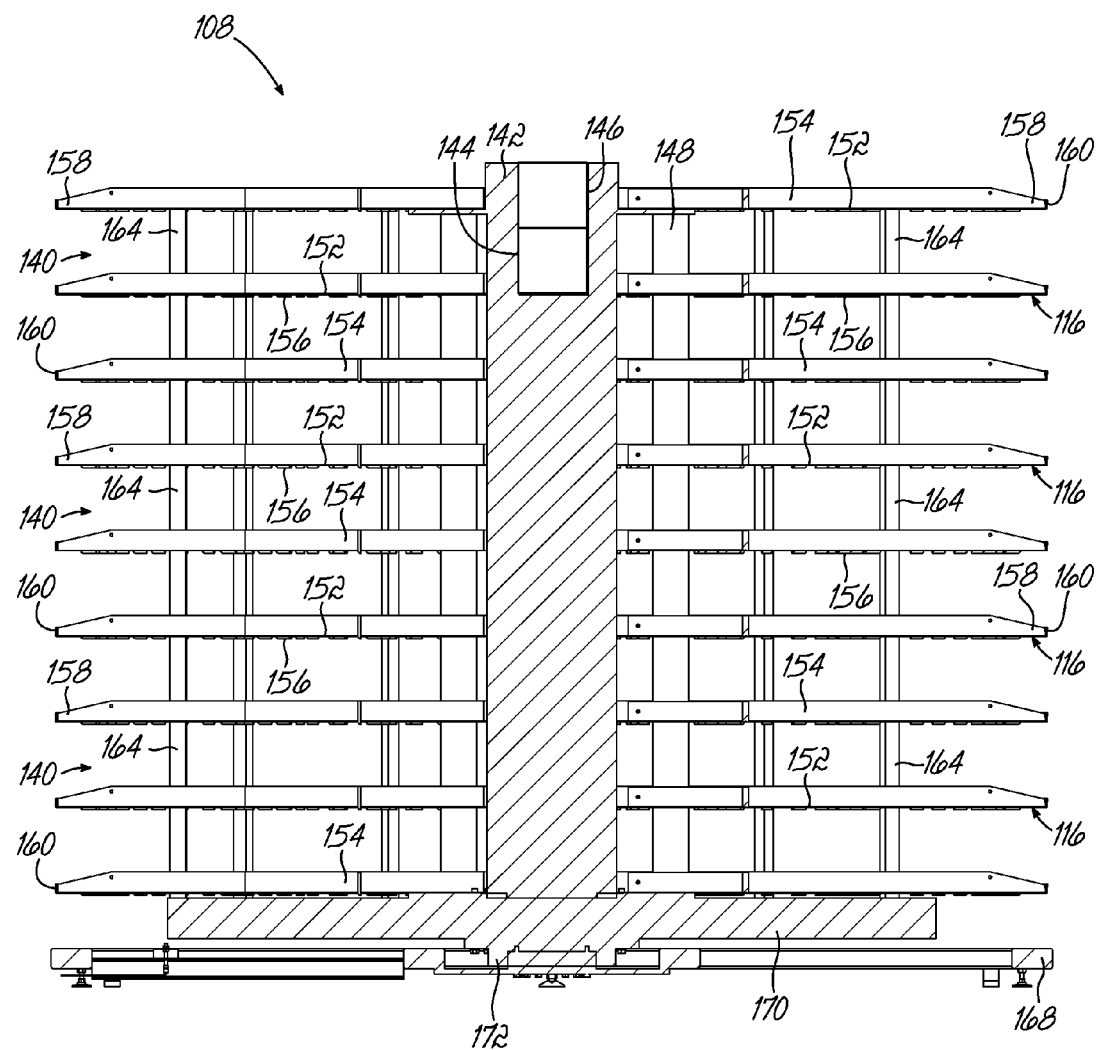
FIG. 9B is a side cross-sectional view of the storage carousel of FIG. 9A, further illustrating assembly features of dividers used on the shelves.

The layout and construction of each of the shelves 116 defining the storage bins 140 is further shown with reference to FIGS. 8, 9A and 9B. To this end, each shelf 116 is defined by a horizontal platform 152 and a plurality of divider plates 154 hooked into engagement with the horizontal platform 152. More specifically, the horizontal platform 152 is formed with radially-oriented slots (not shown) configured to receive J-hooks 156 (several of which are shown in FIG. 9B) extending downwardly from the divider plates 154. These J-hooks 156 are aligned with and inserted into the slots and then the divider plate 154 is slid outwardly to lock these J-hooks 156 into engagement with the bottom of the horizontal platform 152. Simultaneously, the leading tip end 158 of the divider plate 154 comes into abutting relation with a rubberized outer peripheral lip 160 on the horizontal platform 152. The outer peripheral lip 160 is shown in FIG. 9B and is also shown in perspective in FIG. 10, where it is also shown that each storage bin 140 includes a location barcode 162 mounted on this outer peripheral lip 160 for purposes described below. This process is repeated for each divider plate 154 on the portion of the shelf 116 being assembled, with the smaller length divider plates 154 being inserted first and the longer length divider plates 154 inserted last. In the exemplary embodiment, each shelf 116 is formed in portions of one-third of a shelf (schematically shown by arrow 163 in FIG. 9A), and then these third portions are coupled to one another with screw or bolt fasteners. The entire shelf 116 is then configured for sliding engagement onto the central shaft 142 and the alignment shafts 148.

When the shelf 116 has been fully assembled as shown in FIG. 9A, the horizontal platform 152 and the divider plates 154 have maximized the amount of space within the radially-oriented storage bins 140. To this end, each shelf 116 includes six large storage bins 140a extending directly from the six sides of the hexagonal central shaft 142 of the storage carousel 108. Each of the six large storage bins 140a is sized to receive four storage boxes filled with medical items. Equally spaced between adjacent large storage bins 140a, a set of six medium storage bins 140b are formed that are sized to receive three storage boxes filled with medical items. The medium storage bins 140b also include a clearance at the innermost end to receive one of the alignment shafts 148 there through as shown in FIG. 9A. Finally, a set of small storage bins 140c is formed between each medium storage bin 140b and the corresponding two adjacent large storage bins 140a. Consequently, there are twelve small storage bins 140c formed on each shelf 116, each small storage bin 140c being sized to receive one or two storage boxes filled with medical items. Each of the storage bins 140a, 140b, 140c receives medical items in full cases or product boxes. It will be understood that additional divider plates 154 may be selectively positioned in the middle of the storage bins 140a, 140b, 140c as shown in FIG. 9A (but not in FIG. 8) to further provide additional storage locations in other embodiments of the invention. The shelf 116 also includes a plurality (24 in the exemplary embodiment) of wedge-shaped bins 140d located between the small storage bins 140c and the adjacent medium and large storage bins 140b, 140a. These wedge-shaped bins may also be assigned a barcode and filled with loose medical items not contained in full cases or storage boxes, thereby using as much storage space on the horizontal platform 152 as possible.

Thus, each shelf 116 includes 48 positions and storage bins 140 that must be indexed around the storage carousel 108: six large storage bins 140a, six medium storage bins 140b, twelve small storage bins 140c, and twenty-four wedge-shaped storage bins 140d. The shelves 116 are positioned in the same orientation as adjacent shelves 116 such that each of these 48 positions defines a vertical storage column 165 including a stack of storage bins 140 all accessible simultaneously when the position is located at the opening 130 of the door 122. With nine shelves 116 per storage carousel 108, this results in 432 full case sized storage bins 140 on each storage carousel 108 (and over 2000 storage bins 140 in the entire ULV system 100 shown in FIG. 5). In the alternative embodiment described above with intermediate divider plates 154 in the full case sized storage bins 140, the number of storage locations in the storage carousel 108 may be increased to 648 total locations. Ideally, the larger storage bins will be loaded with medical items that are more frequently used and the smaller storage bins and wedge-shaped bins will be loaded with less-prescribed medical items. This arrangement of medical items on the storage bins 140 will reduce the frequency of when the storage carousel 108 needs reloaded with bulk inventory. Most preferably, the storage carousel 108 is loaded with enough bulk inventory to work through a full day shift and then be reloaded once per day by technicians in overnight or off hours.

The divider plates 154 may be designed with various shapes and sizes, two of which are shown in FIG. 8 and FIG. 9B. Extending in an opposite direction from the J-hooks 156, each divider plate 154 may also include spacing supports 164 configured to extend upwardly into contact with the bottom of the next shelf 116 in series on the storage carousel 108. These spacing supports 164 can be repositioned depending on the particular layout of J-hooks 156 and corresponding slots so that the spacing supports 164 do not abut a J-hook 156. In other embodiments of the storage carousel 108, additional structure may be used to ensure accurate and consistent spacing of the shelves 116, such as structure on the central shaft 142 directly supporting the horizontal platforms 152. Regardless of the method of spacing the shelves 116, adjacent shelves 116 define a height of each storage bin 140 that is sized to receive open cases or product boxes of medical items. The close fitting of the full cases of medical items in the storage bins 140 substantially reduces any movements that may occur while the storage carousel 108 rotates between positions at the door 122, thereby reducing any likelihood of medical items being thrown from the shelves 116.

As shown in FIG. 8, the storage carousel 108 may optionally include a top wall 166 to cover at least a portion of the uppermost shelf 116. The top wall 166 is supported directly by the central shaft 142 and may also be supported by the divider plates 154 of the top shelf 116. This top wall 166 may be omitted in some embodiments, such as the totally enclosed storage carousel used with controlled substances and described with reference to FIGS. 13 and 14 below. Also shown in FIG. 8, the storage carousel 108 includes a support base 168 configured to be fastened in position on the floor surface to further stabilize the storage carousel 108. The support base 168 is also shown in the cross sectional view of FIG. 9B, where it is further shown that the storage carousel 108 includes a primary support platform 170 holding the central shaft 142 and the bottom shelf 116 and a rotary bearing 172 mounted on the support base 168. The rotary bearing 172 enables the primary support platform 170 and the remainder of the storage carousel 108 above the primary support platform 170. The motor 146 engages the primary support platform 170 adjacent the rotary bearing 172 and drives the shelves 116 with the aforementioned indexed movement relative to the opening 130 in the door 122 of the cage 106. Therefore, any medical item within the storage bins 140 may be readily brought into position for access by an operator 72 as described in detail below.

Figure 10:
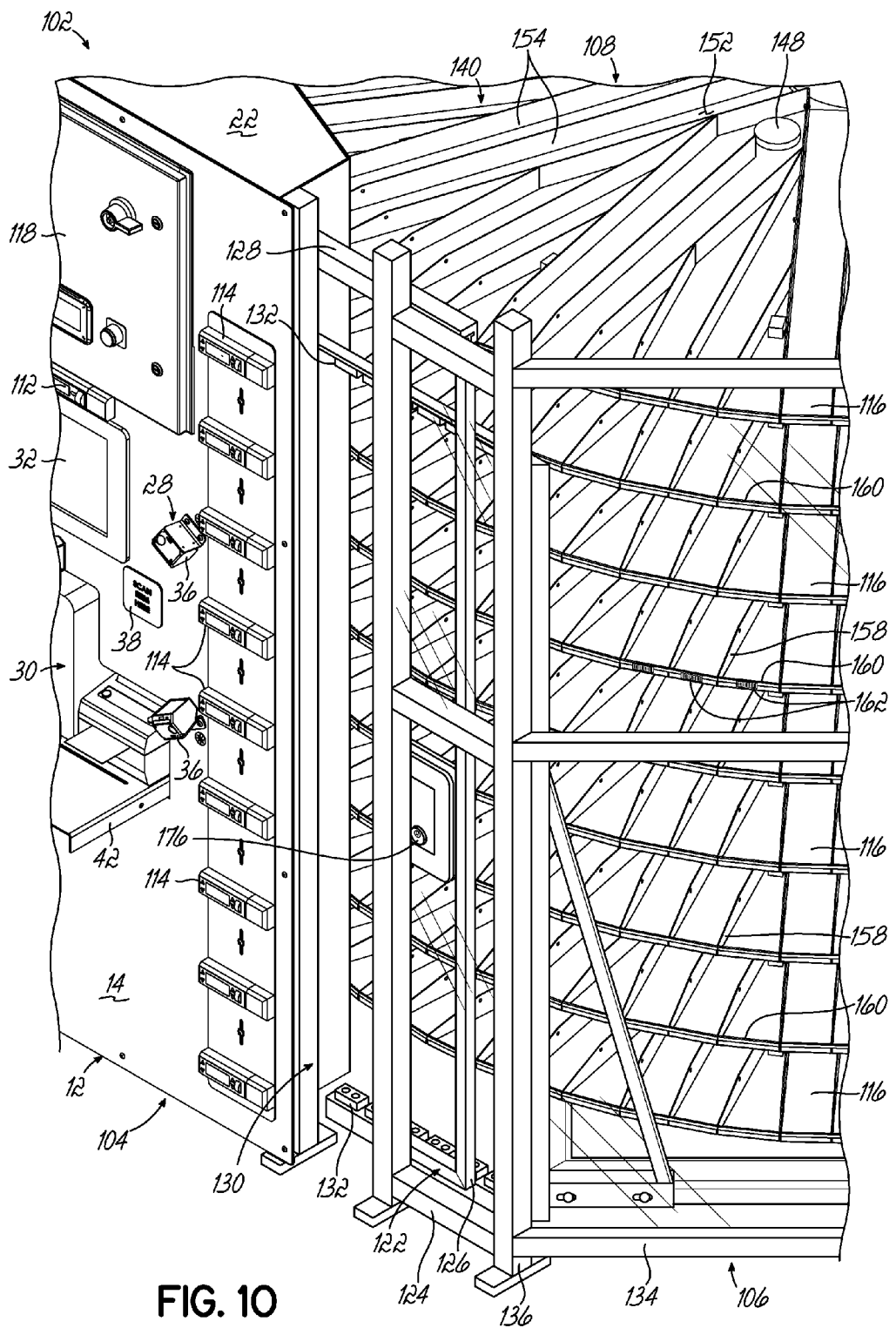
FIG. 10 is a detailed perspective view of the ULV carousel unit of FIG. 6, showing specific features of a door providing access through the cage to the storage carousel.

With reference to FIG. 10, the portion of the ULV carousel unit 102 adjacent the door 122 is shown in further detail. From this perspective view, the moveable door panel 126 is clearly shown in an open position located behind the stationary door panel 124. The light curtain optical sensor 132 is also shown and includes a plurality of lasers or similar optical sources and receivers (not shown) that form an effective curtain of light that will be interrupted whenever an operator 72 sticks his arm into the opening 130. The optical sensor 132 is operatively connected to the electrical control box 118 and provides a signal that will stop the motor 146 from rotating the storage carousel 108 if such rotation is in progress when the operator 72 inserts his hand through the opening 130. Consequently, the optical sensor 132 ensures the safety of the operator 72 using the ULV system 100. The optical sensor 132 will also be used to detect movement of operator hands into the carousel area when no transactions (removing stock or replenishing stock) are present. If activity is detected between transactions, flags will be placed on the pick locations that are present at the opening 130. These flags will be used to trigger physical audits to aid in maintaining perpetual inventory accuracy. FIG. 10 also illustrates that the door 122 includes a locking mechanism 176 on the moveable door panel 126 that can be used to lock the moveable door panel 126 in a closed position blocking the opening 130. This closing and locking of the door 122 should be performed anytime the operator(s) 72 stop actively working with the ULV carousel units 102 to prevent any unauthorized access to the storage bins 140 that are located adjacent the opening 130 during periods of non-use. The door 122 is a manually operated door in the exemplary embodiment shown, but it will be understood that the door 122 may be motorized in other embodiments such as the controlled substances carousel described in detail below.

FIG. 10 also illustrates the correspondence of the levels of the storage carousel 108 and the light tree on the LVK 104 in further detail. In this regard, each of the pick modules 114 is positioned on the LVK 104 in order to be at least generally aligned with a corresponding shelf 116 on the storage carousel 108. As a result, an operator 72 will not be confused about which shelf 116 to retrieve a desired item from, as the pick module 114 immediately adjacent to that storage bin 140 and shelf 116 will be the one illuminated during such a signal to the operator 72. Thus, each pick module 114 is selectively illuminated according to pick indicator logic described in further detail below. When the storage carousel 108 rotates to a position with a storage bin 140 having a medical item to be retrieved facing towards the opening 130, the pick module 114 and the order control module 112 will both prompt the operator 72 to go to the intended storage bin 140 and pick the indicated number of the medical items. The operator 72 can pick multiple items at once or one at a time, although it will be preferred that only one medical item be pulled at a time. If medical items are to be pulled from multiple shelves 116 at a particular position, only one of the pick modules 114 at a time will illuminate in the exemplary embodiment. Alternatively, all of the pick modules 114 for that position may simultaneously illuminate and allow the operator 72 to select which medical items to obtain first for scanning and labeling. Similar to the optical sensor 132, the pick modules 114 are also operatively connected to the other elements of the ULV carousel unit 102 such that the number of items to retrieve indicated on the display of the pick module 114 will automatically decrement by one when the second scan verifies that one of those medical items has been properly labeled with a patient label.

Figure 11:
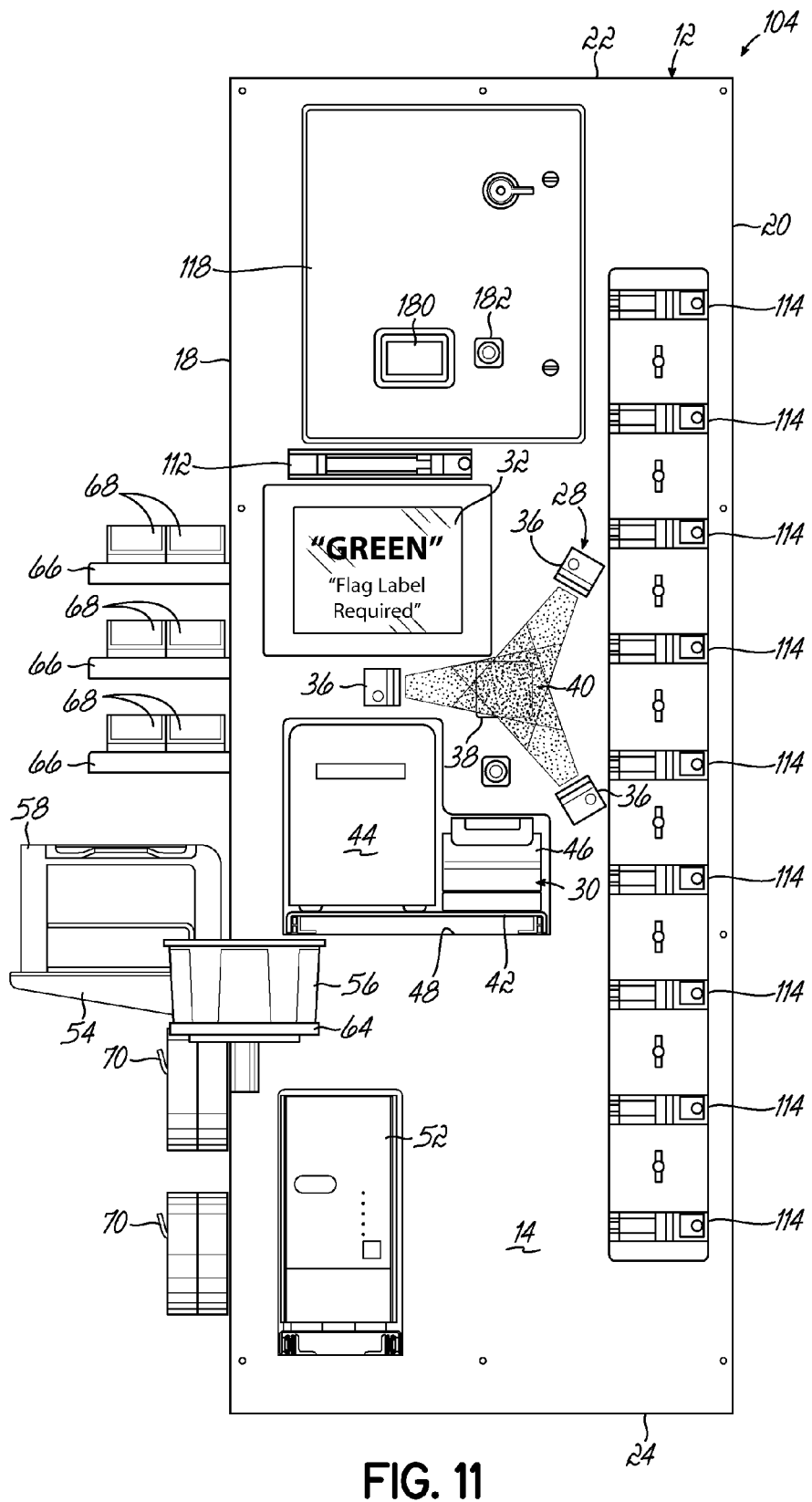
FIG. 11 is a front view of the LVK used with the ULV carousel unit of FIG. 6, illustrating the scanning fields for the LVK and a message provided on a touch screen display.

With reference to FIG. 11, the LVK 104 used with the ULV carousel units 102 is shown in detail. As noted above, the LVK 104 includes many of the same elements of the kiosk 10 described in the first embodiment, including: the box shaped housing 12; a barcode scanner assembly 28 with barcode scanners 36 and a scanning indicia plate 38 near a scan area 40; a label printing station 30 with a patient label printer 44 and a flag label printer 46; a touch screen display 32 for receiving input and delivering output to an operator 72; a computer 52; stationary and articulating shelves 54, 64; and a plurality of bin shelves 66. The LVK 104 may interface with the storage carousel 108 via a drive controller (not shown in FIG. 11) incorporated with the electrical control box 118, where the drive controller is configured to control the motor 146 that rotates the storage carousel 108. The electrical control box 118 also includes a human machine interface HMI 180 configured to display operating status of the mechanical elements such as the motor 146 controlled by the drive controller. The electrical control box 118 also includes an emergency stop button 182 for stopping all operations of the storage carousel 108 when necessary for any reason. The HMI 180 and the emergency stop button 182 are located about at the same height as the highest shelf 116 and pick module 114, which has been calculated to be a height most operators 72 can easily reach. In all other respects, the LVK 104 is arranged along the front wall 14 of the housing 12, substantially the same as the previously-described kiosk 10, which enables operators 72 to work efficiently at both kinds of LVKs 10, 104.

Figure 12A:
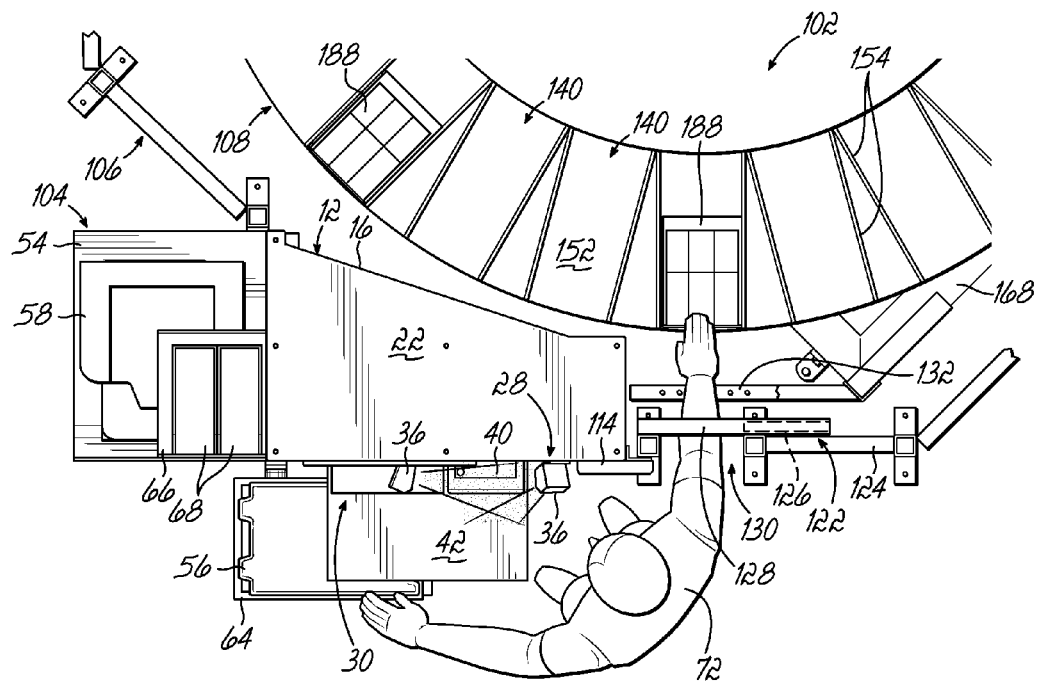
FIG. 12A is a top view of a portion of the ULV carousel unit of FIG. 6, showing an operator reaching into the storage carousel to retrieve an item to be labeled in a first step of an operational process.

Referring to this efficient work process, a series of operations performed by an operator 72 at the LVK 104 and storage carousel 108 of one ULV carousel unit 102 is shown in FIGS. 12A through 12E. The operator 72 begins by carrying a tote 56 for a current batch of medical items to a ULV carousel unit 102 having an order control module 112 indicating that it contains picks for that batch. Upon arrival at the ULV carousel unit 102 or prompting of a new batch, the storage carousel 108 will have rotated to provide access to a first pick of the batch. As described in further detail below, when multiple picks for a batch are on a single storage carousel 108, the first and subsequent picks are ordered to minimize the amount of rotary movement of the storage carousel 108 required throughout the entire batch. More specifically, the first picks are presented by selecting the vertical storage column 165 with the highest number of picks available and moving that vertical storage column 165 to the opening 130 first. With the tote 56 in position on the articulating shelf 64 as shown in FIG. 12A, the operator 72 is ready to begin a scanning and labeling process for each medical item needed for the batch from that storage carousel 108.

Figure 12B:
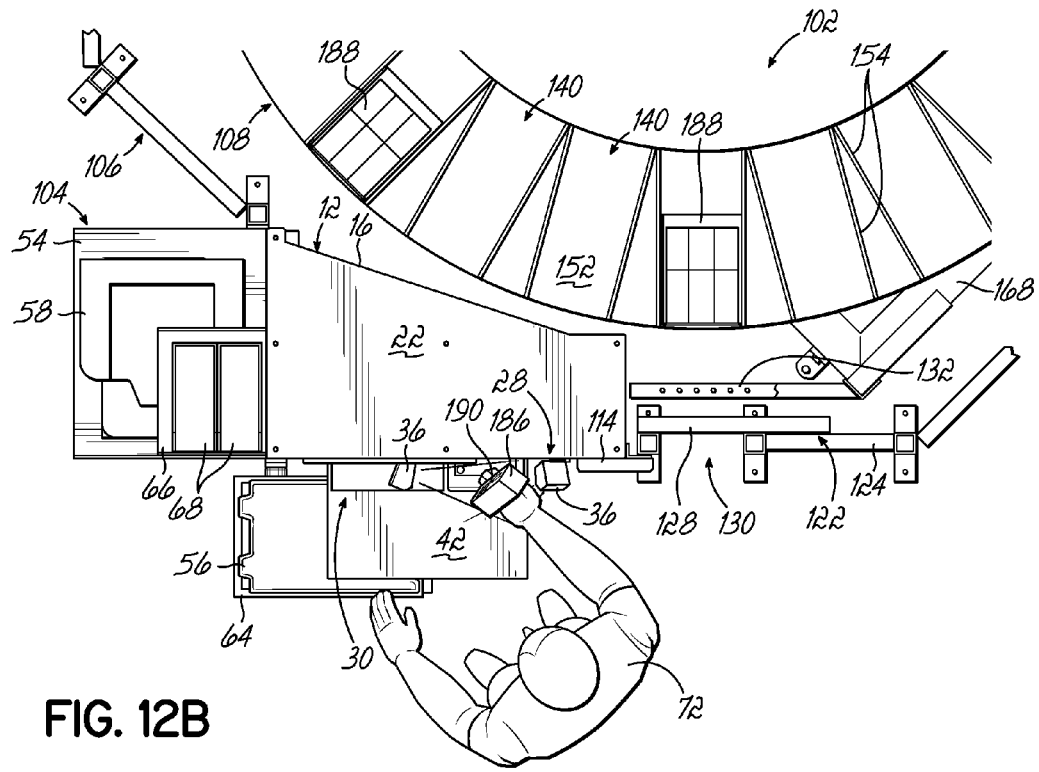
FIG. 12B is a top view of the portion of the ULV carousel unit of FIG. 12A, showing the operator scanning the product label on the item in a second step of the operational process.
Figure 12C:
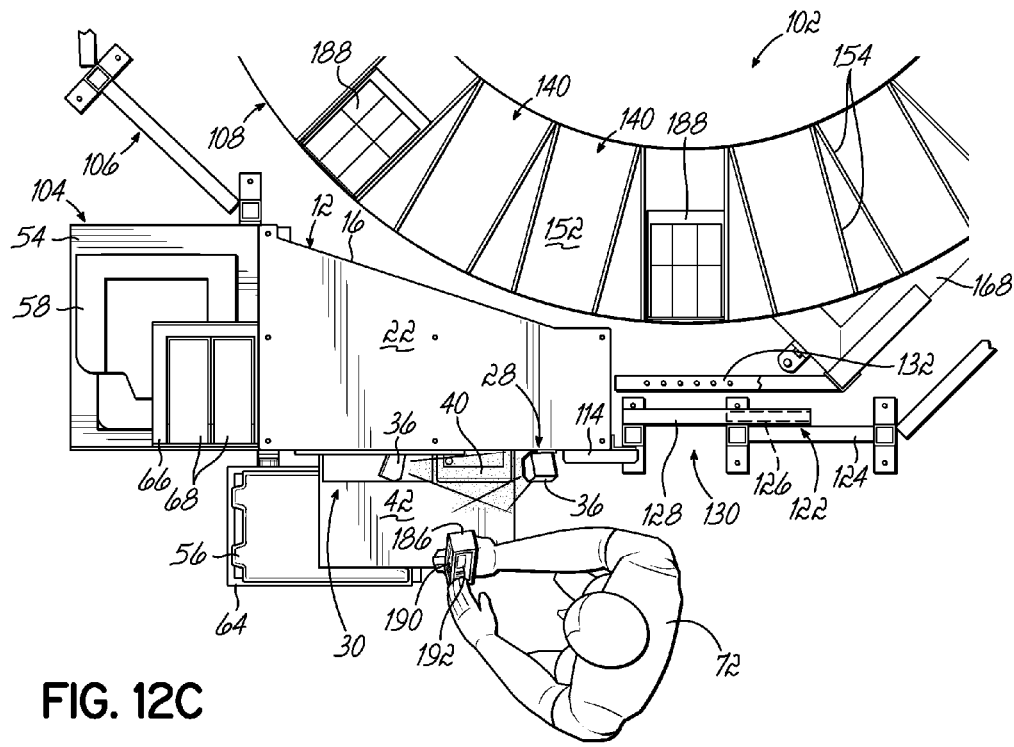
FIG. 12C is a top view of the portion of the ULV carousel unit of FIG. 12B, showing the operator applying a printed patient label on the item in a third step of the operational process.

Beginning with FIG. 12A, the operator 72 reaches through the opening 130 at the door 122 and into the storage bin 140 indicated by the illuminated pick module 114 to retrieve a medical item 186 from a storage box 188. The medical item 186 will already be provided with a product label 190. As shown in FIG. 12B, the operator 72 then moves this product label 190 into the scan area 40 to indicate removal of the medical item 186 from the storage carousel 108. If the incorrect medical item 186 was removed from the storage carousel 108, then the touch screen display 32 will prompt the operator 72 to replace that medical item 186 and retrieve the correct one. If the first scan is correct, then this first scan will prompt the printing of a patient label at the patient label printer 44. If a flag label is required or some other packaging such as bagging is required, the display 32 will indicate as such, and the operator 72 can prompt the LVK 10 at the display 32 to print a flag label at the flag label printer 46. As shown in FIG. 12C, the operator 72 then applies the patient label 192 to the medical item 186.

Figure 12D:
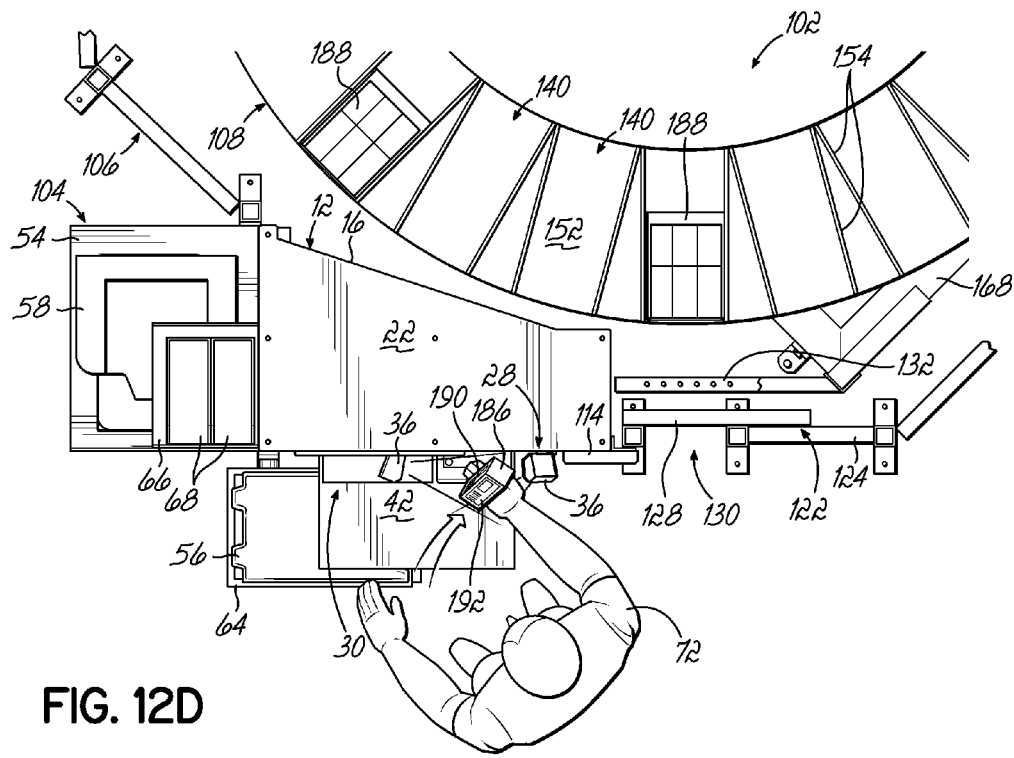
FIG. 12D is a top view of the portion of the ULV carousel unit of FIG. 12C, showing the operator scanning the product label and the patient label on the item in a fourth step of the operational process.
Figure 12E:
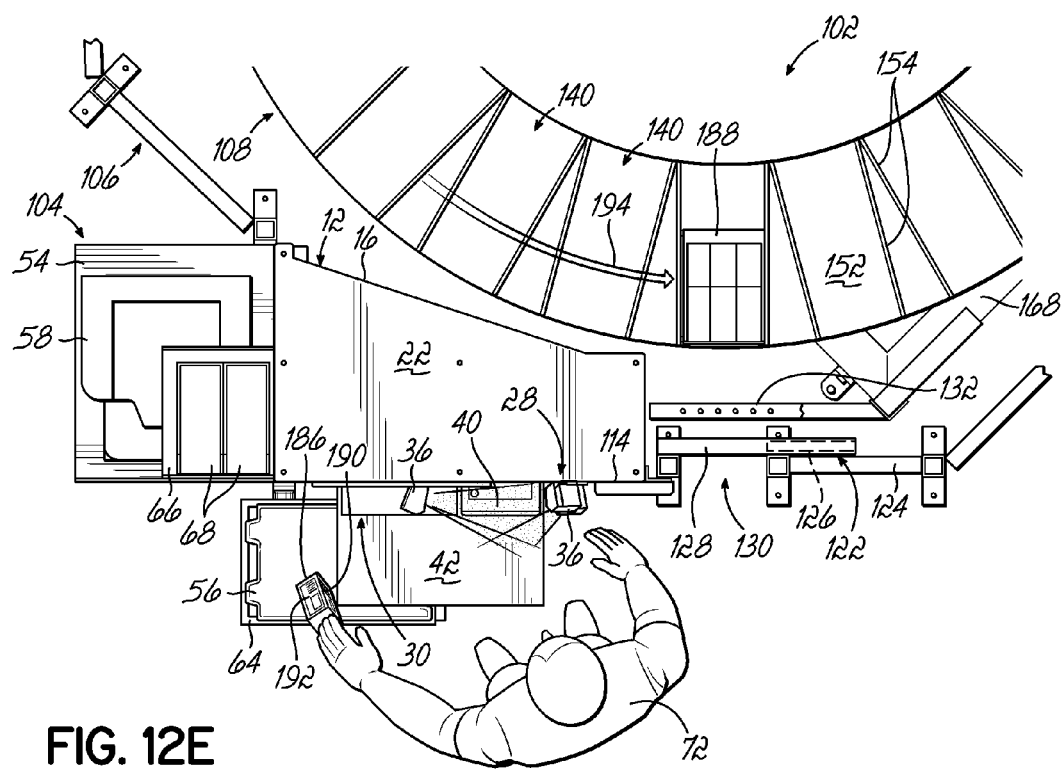
FIG. 12E is a top view of the portion of the ULV carousel unit of FIG. 12D, showing the operator placing the labeled item in a tote while the storage carousel rotates to provide access to a new item in a fifth step of the operational process.

Once this patient label 192 and any other packaging or labels are in position, the operator 72 performs a second scan at the scan area 40, this time of both the patient label 192 and the product label 190 as shown in FIG. 12D. Assuming that these labels 190, 192 are verified by this second scan to be a valid match, the display 32 will prompt the operator 72 to place the labeled medical item 186 in the tote 56 at the articulating shelf 64 as shown in FIG. 12E. As also shown in FIG. 12E, if another medical item 186 is located at a different position in the storage carousel 108, the second scan and validation cause the drive controller to actuate rotation of the storage carousel 108 to the location with the next pick for the batch as shown by arrow 194. The next pick for the batch is selected based upon the vertical storage column 165 that has the highest number of picks to retrieve, or the closest column if multiple columns contain the highest number of picks to retrieve (thereby streamlining the process). Because even a full 180 degree rotation only takes about 2.5 seconds with the storage carousel 108, the operator 72 will almost certainly spend more than the amount of time needed to rotate the storage carousel 108 to place the labeled medical item 186 in the tote 56. Thus, no delays are encountered by the operator 72 waiting on rotation of the storage carousel 108. The operator 72 can repeat this process for each item in the batch contained in the storage carousel 108 until all items in the batch are labeled with patient labels 192 and verified to be labeled correctly. If further medical items 186 are to be retrieved from other ULV carousel units 102 in the ULV system 100, the order control module 112 will direct the operator 72 to move the tote 56 to the next ULV carousel unit 102 with a needed medical item 186 for the batch. This process repeats until the tote 56 is filled with all needed items from the ULV system 100, at which point the tote 56 is moved to downstream processing where the contents can be prepared for shipping to the end consumer.

Thus, the medical items needed for an entire pre-sorted batch of medical items is brought to the operator for labeling and verification without requiring the operator to retrieve and pre-sort the batches from bulk inventory held on aisles of storage racks. These medical items can be labeled with patient labels and verified all at once upon retrieval from the storage carousels, regardless of the specific type of packaging used to store the medical items. This process enables labeling on demand and significantly fewer human touches required to retrieve, label, and process the products in a customer order for shipping to the end consumer. This on demand labeling ensures that all medication order changes, details, label instructions, and other information are up to date at the latest possible time before applying the patient label to the product. In addition, this on demand labeling enables checking for conditions that would prompt pharmacist re-verification of the clinical order such as drug contra-indications, allergen alerts, and product changes that may arise in the time period immediately before printing and applying the patient label to the product. Furthermore, the accurately pre-sorted totes of medical items can be scanned and handled on a tote-by-tote basis (for WIP and SHP totes as described above, as ASL totes require further scanning actions to separate the medical items into customer orders) downstream of the labeling and verification process rather than requiring sorting into separate shipping bags during downstream processing. This process can therefore improve the number of medical items labeled and verified over a traditional manual process from 1 product per 1-3 minutes to about 4-6 products per minute. It will be understood that the LVK and ULV can receive product in totes from an automated labeling and verification (ALV) system or other pharmacy process as well as send items to the ALV system for further consolidation of items. When combined with the ALV system for blister cards and product boxes described above, the ULV system also enables up to 85-90% of prescribed medical items to be labeled on demand in a more efficient manner at either the ALV or ULV systems of the pharmacy.

The ULV system is also advantageous because it eliminates any operator delay based on waiting for a storage carousel to rotate because the storage carousel rotates simultaneous to the operator working on a previous pick. The ULV system also enables leveraging of "First In, First Out" (FIFO) inventory control by directing the operator to pick from the oldest stock in the storage carousels, thereby reducing the amount of product waste. The ULV system also enables leveraging of "First Expired, First Out" (FEFO) inventory control by directing the operator to pick from the stock that has the earliest expiration dates in the storage carousels. Any dose or medication problems (such as allergy contra-indications for a particular patient) can also be identified at the point of labeling contact, which provides a real time quality review for the prescription filling process. By removing substantially all of the batch collection and pre-sorting steps in the prescription filling process for 85-90% of medical items delivered by a pharmacy, the efficiency and quality of the filling process for customer orders is improved significantly by reducing the amount of human touches required to move medical items from bulk stock to a final shipping container.

Figure 13:
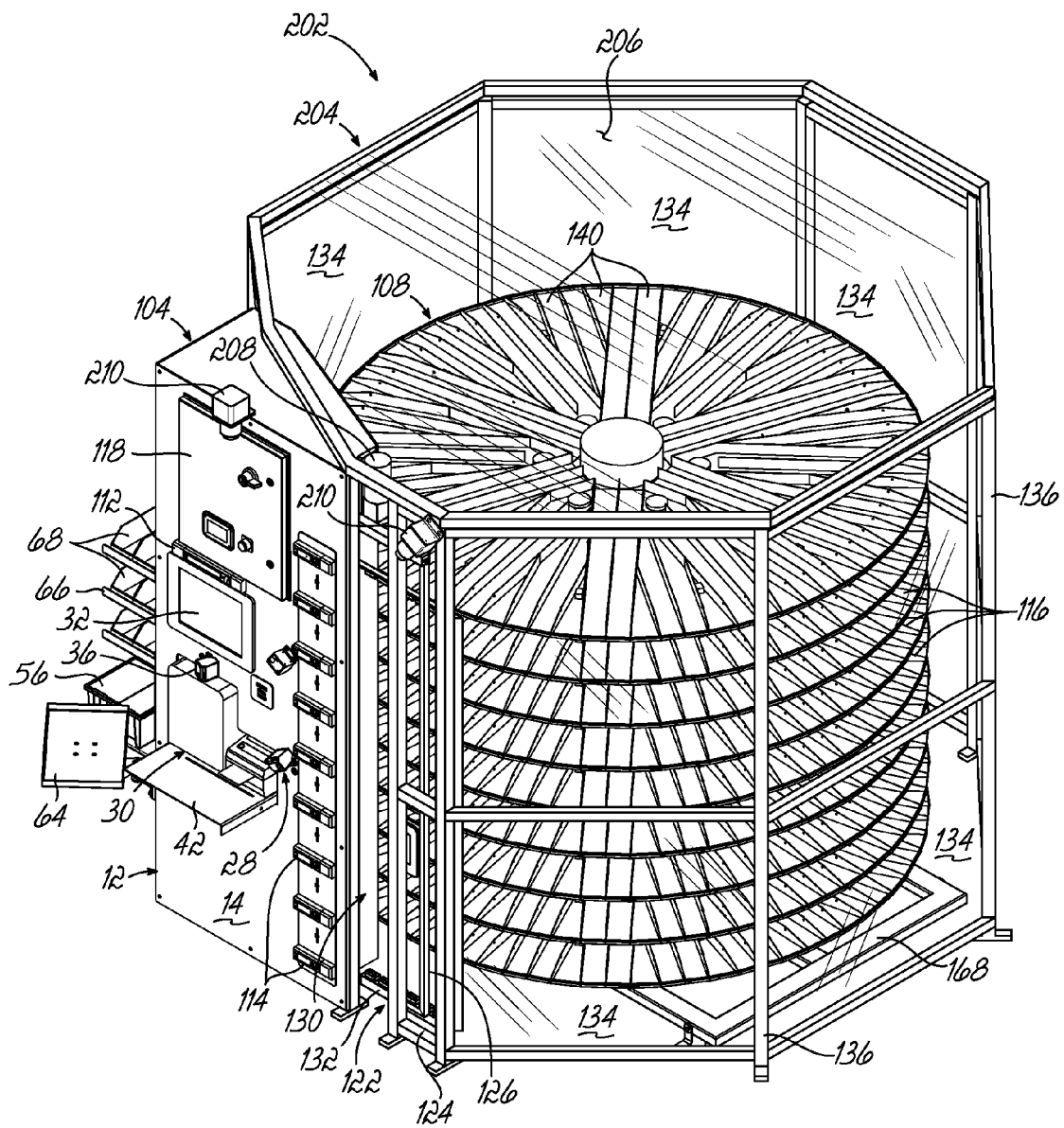
FIG. 13 is a perspective view of another embodiment of a ULV carousel unit used with the ULV system of FIG. 5, the ULV carousel unit being configured to contain controlled substances.
Figure 14:
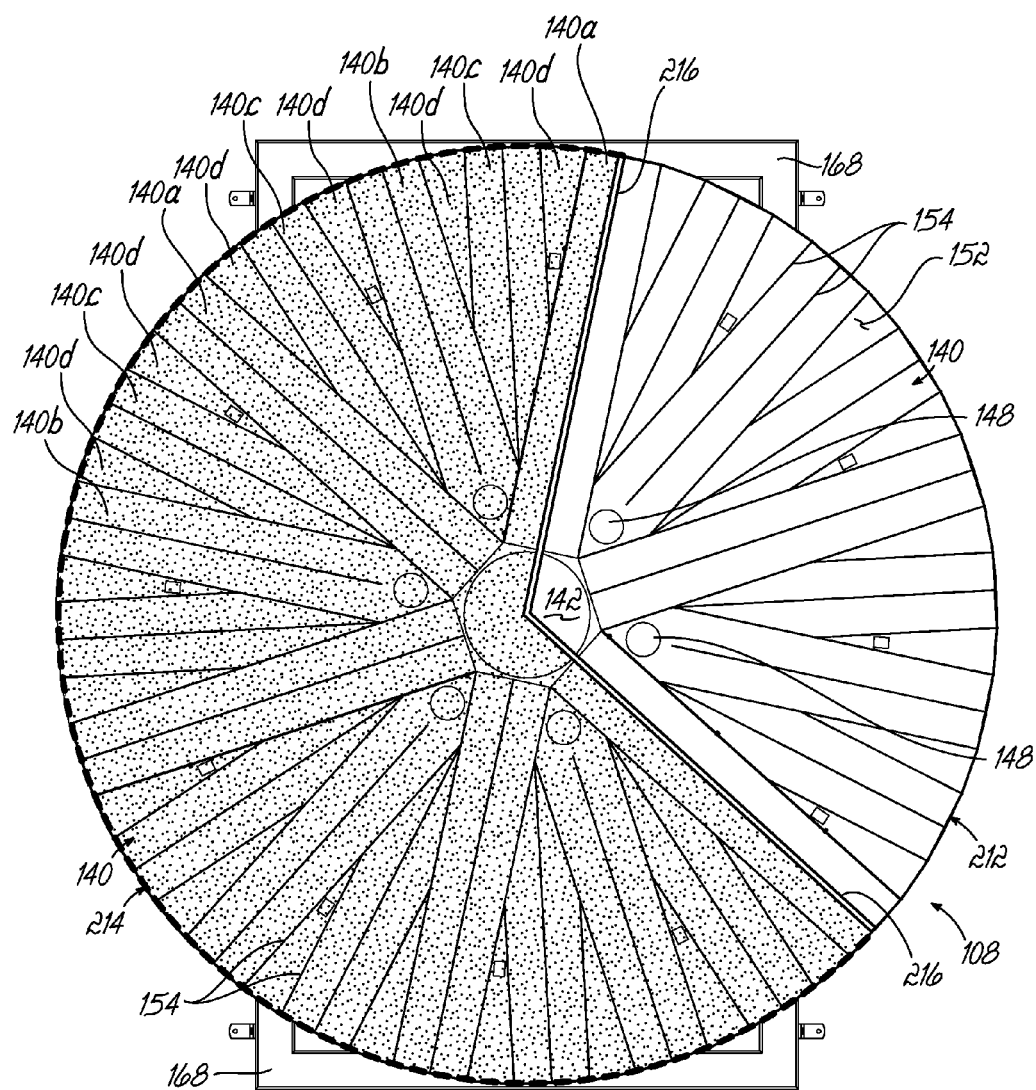
FIG. 14 is a top schematic view of the storage carousel used with the ULV carousel unit of FIG. 13, illustrating the allocation of various sections of the shelves to different levels of controlled substances.

Another embodiment of a ULV carousel unit 202 used with the ULV system 100 is shown in FIGS. 13 and 14. More specifically, the ULV carousel unit 202 is highly similar to the ULV carousel unit 102 previously described with some modifications so that this ULV carousel unit 202 can deliver DEA controlled substances to the operator 72. The same elements from the previously-described ULV carousel unit 102 have been marked with the same reference numbers in FIGS. 13 and 14 without additional explanation below. In order to be DEA compliant, the cage 204 is modified to include cage panels 134 welded together and a solid cage top 206 welded to the cage panels 134 and to the LVK 104. The full closure and welding together of the cage 204 enables controlled substances (e.g., medical items on Schedules 2-5 of the controlled substances list) to be contained within the ULV carousel unit 202 while complying with DEA regulations.

Another modification made to this version of the ULV carousel unit 202 is that the door 122 is now mechanized by including a door motor 208. Thus, the door 122 can be programmed to automatically close anytime the ULV carousel unit 202 is not being actively used by an authorized operator 72. In addition, cameras 210 are mounted on the ULV carousel unit 202 to record images of the operator 72 working at the LVK 104 and record images of any movements into and out of the cage 204 when the light curtain optical sensor 132 detects entry through the opening 130. Consequently, a full video record of all transactions is stored in memory for later review if required to meet DEA compliance or to reconcile a diversion.

With reference to FIG. 14, the medical items may also be assigned to storage bins 140 within the storage carousel 108 to separate all higher level security controlled substances (e.g., Schedule II) from lower level controlled substances (Schedules III-V). For example, as indicated by the labels in FIG. 14, Schedule II controlled substances may be located in a first pie-piece-shaped portion 212 of the shelves 116 while Schedule III-V controlled substances may be located in a second pie-piece-shaped portion 214 of the shelves 116. The divider plates 154 used at the interface between the first and second portions 212, 214 may be modified to be completely solid blocking plates 216 as shown in FIG. 14. These solid blocking plates 216 prevent an operator 72 with authorized access to only Schedule III-V controlled substances from reaching into Schedule II storage bins 140 under any circumstances. In addition, the driver controller will rotate the storage carousel 108 the long way between two picks if the shorter rotation angle puts Schedule II storage bins 140 in front of the opening 130 when an unauthorized operator 72 is working at the ULV carousel unit 202. Thus, even if the storage carousel 108 malfunctions and stops rotating, the operator 72 without authorization to higher levels of controlled substances will never have access to those controlled substances. Further modifications are also performed to the control process used with this embodiment, such as requiring special log in of operators to the ULV carousel unit 202 containing controlled substances, as readily understood in the art. Consequently, the ULV system 100 can include one or more ULV carousel units 202 that provide batches of controlled substances to authorized users in a more efficient manner than the individualized preparation inside a large DEA caged area as used currently.

Figure 15:
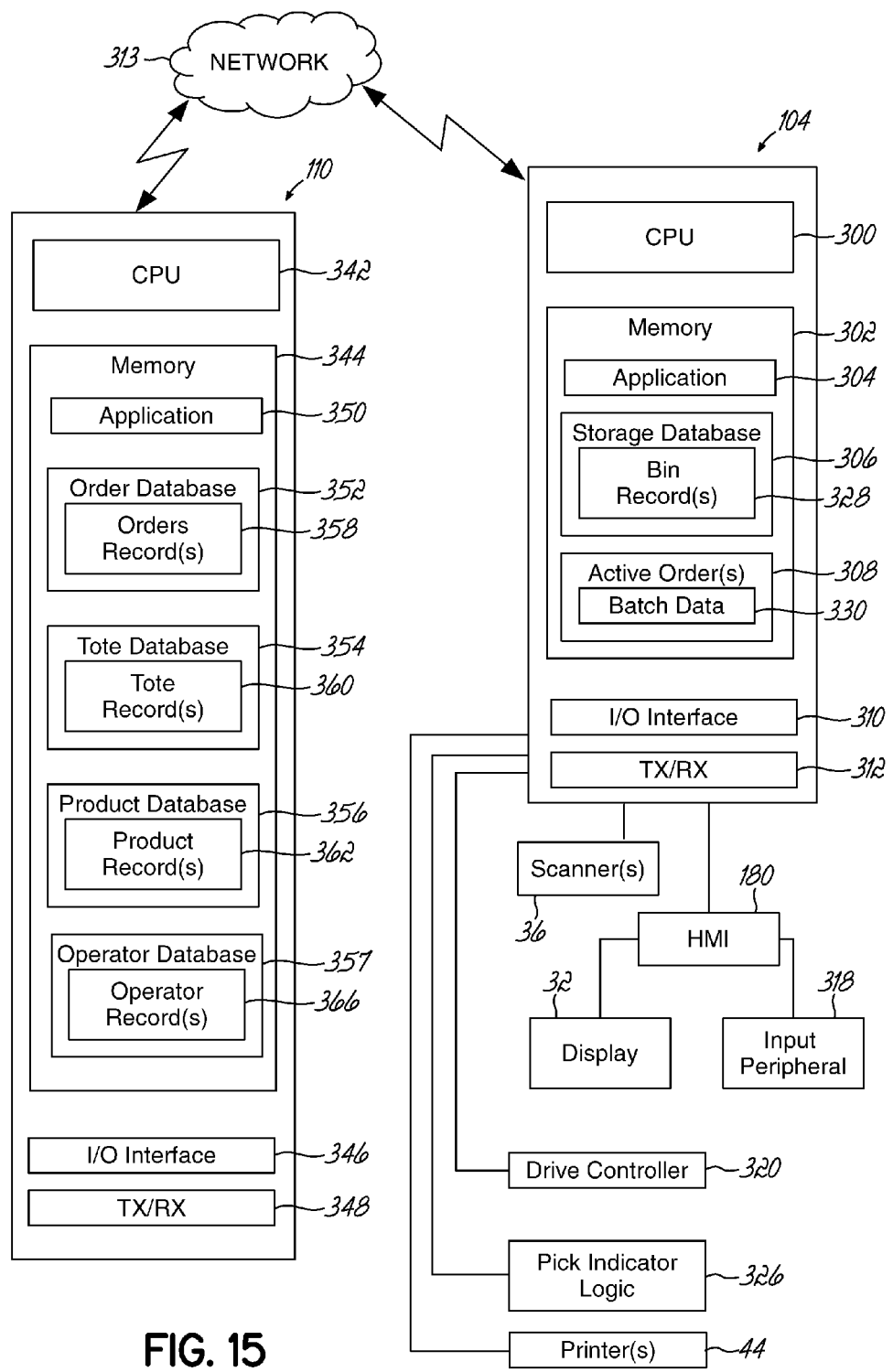
FIG. 15 is block diagram of components of an LVK, ULV system and pharmacy host server consistent with some embodiments of the invention.

FIG. 15 provides a block diagram illustrating components of the label and verification LVK 104 (and/or LVK 10) consistent with some embodiments of the invention. As shown, the LVK 104 includes one or more processors (illustrated as 'CPU') 300 for executing one or more instructions to perform and/or cause components of the LVK 104 to perform one or more operations consistent with embodiments of the invention. The LVK 104 includes a memory 302, where the memory 302 includes an application 304 and one or more data structures 306, 308 stored therein. Application 304 may generally comprise program code that when executed by the processor 300 facilitates retrieving, labeling and/or verifying products for filling a customer order. Furthermore, LVK 104 includes an input/output ("I/O") interface 310 configured to output data to and receive data from one or more peripherals in communication with the LVK 104, a network interface controller ("Tx/Rx") 312 configured to transmit and receive data over a communication network 313, and/or the machine interface ("HMI") 180 that may include one or more peripherals for outputting data to an operator in an understandable format and receiving input data from the operator, including, for example, the display 32 and/or an input peripheral 318 (for example, hand scanner 74).

In addition, the LVK 104 includes one or more scanners 36 that an operator may utilize to input product information and/or patient information from a machine readable object that may be analyzed by the scanner. For example, the one or more scanners 36 may comprise bar code scanners, QR code scanners, RFID readers and/or other such devices, where the machine readable object may comprise a barcode, QR code, RFID tag and/or other such machine readable objects. Furthermore the LVK 104 includes one or more printers 44, 46, where the one or more printers may print patient labels, flag labels, order data and/or other such information/labels that may be useful to an operator and/or supervisor for filling a customer order and/or reviewing filled orders.

In embodiments of the invention where the LVK 104 includes the storage carousel 108 and the cage 106, the LVK 104 includes a carousel drive controller 320 configured to control the motor 146 to cause the storage carousel 108 to rotate a determined amount such that the storage bin 140 may be aligned to the pick location 130 as well as operate the door 122 associated with the cage 106. In addition, such embodiments include pick indicator logic 326 configured to selectively control one or more pick modules 114 and/or an order control module 112 to thereby indicate to an operator particular storage bins 140 from which to retrieve products and information about a batch being processed at the LVK 104. As such, in these embodiments, the processor 300 may interface with the carousel drive controller 320 to cause the carousel drive controller 320 to operate the motor 146 associated with the storage carousel 108 to rotate the storage carousel 108 an amount determined by the processor 300 based on the location of specific storage bins 140 storing products needed to fill an active order. Furthermore, following aligning the vertical storage column 165 to the pick location 130 by rotating the storage carousel 108, the processor 300 may interface with the pick indicator logic 326 to thereby selectively operate one or more pick modules 114 associated with storage bins 140 storing products needed to fill the customer order, to thereby selectively identify storage bins 140 from which the operator should retrieve products.

The carousel drive controller 320 may be connected to position indexing logic 98 configured to monitor which vertical storage column 165 is aligned to the pick location 130 and communicate such positional data to the processor 300. As such in these embodiments, the processor 300 may analyze the positional data received from the carousel drive controller 320 to determine a direction of rotation and degree of rotation in which the storage carousel 108 should be rotated to align particular storage bins 140 storing products required to fill a customer order. The processor 300 may interface with the carousel drive controller 320 based on such determined direction and degree of rotation to rotate the storage carousel 108 such that an operator may retrieve, label, and verify products needed to fill a customer order.

More specifically, the carousel drive controller 320 may be operated according to logic that causes the vertical storage columns 165 to be presented in an efficient and streamlined manner to the opening 130. To this end, the vertical storage column 165 with the highest number of medical items to be picked is positioned at the opening 130 first. After all of the picks are completed in that vertical storage column 165, the next vertical storage column 165 to be presented is selected based on which vertical storage column 165 contains the highest number of picks remaining, or the closest of these if multiple vertical storage columns 165 contain the highest number of picks remaining. Thus, the movement of the storage carousel 108 is streamlined or minimized.

In some embodiments consistent with the invention, the memory 302 includes a storage database 306 that in turn includes one or more bin records 328. A bin record 328 generally includes data corresponding to the particular storage bin 140, including for example, data corresponding to the product stored in the particular storage bin 140, such as the medical item name, dosage, quantity per product, expiration date, lot number, controlled substance schedule number, the quantity of units of the product stored in the location, and/or other such relevant information. As such, embodiments of the invention may include a bin record 328 corresponding to each storage bin 140 of the storage carousel 108 associated with the LVK 104. The memory 302 may store an active order data structure 308, including batch data 330, where the batch data may indicate each unit of product required to be picked and a patient associated with each unit (referred to herein as a pick). In addition, the batch data may store data indicating a particular customer (e.g., customer facility, customer pharmacy, etc.) and/or other such relevant information needed to label and verify each pick of the customer order in the batch data corresponding to the LVK 104.

As shown in FIG. 15, the LVK 104 may be in communication with the pharmacy host server 110 over the communication network 313. The pharmacy host server 110 includes at least one processor 342 and a memory 344. In addition, the pharmacy host server 110 includes an I/O interface 346 configured to input data to the processor 342 and output data from the processor 342, to and from one or more connected peripheral devices. The pharmacy host server 110 communicates with the LVK 104 over the communication network 313 via a network interface controller (TX/RX) 348. The memory 344 includes an application 350 stored therein, where the application includes one or more instructions stored in a format that may be executed by the processor 342 to perform or cause to be performed one or more operations consistent with embodiments of the invention.

Furthermore, the memory 344 may store one or more data structures, including an order database 352, a tote database 354, a product database 356, and/or an operator database 357. The order database 352 may include one or more order records 358, where each order record 358 may correspond to a customer order. An order record 358 may include an identifier corresponding to the customer (e.g., a customer number, customer name, etc.), each product and a corresponding quantity for the customer order, a patient associated with each unit of each product in the customer order, identification numbers for totes 56 associated with the customer order, shipping information associated with the customer order, and/or other such information. The tote database 354 includes one or more tote records 360, where each tote record 360 corresponds to the box/shipping container 56 (i.e., the "tote") utilized in filling customer orders. Each tote record 360 includes data indicating a customer order with which the corresponding tote 56 is associated, batch data corresponding to the tote 56 for the associated customer order, one or more LVKs 10, 104 where the tote 56 should be placed to receive labeled and verified products for the customer order, a tote type (e.g., a temporary storage tote, a shipping tote, a local delivery tote, etc.), and/or other such information.

The product database 356 includes one or more product records 362, where a product record 362 may store data corresponding to a particular type of product that may be included in a customer order, including products stored in storage bins 140 of storage carousels 108 associated with LVKs 104 in communication with the pharmacy host server 110 as well as other remote storage locations that may also be associated with kiosks such as pick-to-light shelves 109. A product record 362 may include data corresponding to a type of product, including for example, a name of the type of product and/or medical item included in the product, dosage of the type of product, quantity of medical items in the product, a U.S. Drug Enforcement Agency (DEA) controlled substance schedule classification associated with the product, flag product data indicating whether the type of product is a flag label product and/or the number of flag labels needed for the particular type of product, any contra-indications with other types of product(s), storage location data indicating any storage bins 140 storing the particular type of product in storage carousels 108 associated with LVKs 104 and/or remote storage locations storing the type of product, and/or any other information that may be useful in filling customer orders.

The operator database 357 includes one or more operator records 366, where each operator record 366 corresponds to an operator that may utilize the LVK 104 consistent with embodiments of the invention. Each operator record 362 may include data corresponding to the operator, such as an identifier associated with the operator (e.g., the operator's name, an employee identification number, etc.), login credentials associated with the operator including an identification credential (e.g., a user name, identification number, etc.) and an identity verification credential (e.g., a password, a pin number, a key fob number, a biometric registration, etc.), a DEA drug class permission, and/or other such information.

While the data structures 306, 308, 352, 354, 356, 357 are illustrated in FIG. 15 as individual data structures resident on the memory 344 of the pharmacy host server 110 or the memory 302 of the LVK 104, the invention is not so limited. For example, the data represented by the data structures 306, 308, 352, 354, 356, 357 may be combined in one or more data structures, such as one or more relational databases. Moreover, the memory 302, 344 may generally be considered local and/or remote memories accessible by the processors 300, 342 over a local bus network and/or a communication network such as network 313 illustrated in FIG. 15. The memory 302, 344 may represent random access memory (RAM) comprising the main storage of a computer, as well as supplemental levels of memory, e.g., cache memories, non-volatile or backup memories (e.g., programmable or flash memories), mass storage memory, read-only memories (ROM), etc. In addition, the memory 302, 344 may be considered to include memory storage physically located elsewhere, e.g., cache memory in a processor of any computing system in communication with the LVK 104 and/or pharmacy host server 110, as well as any storage device on any computing system in communication with the LVK 104 and/or pharmacy host server 110 (e.g., a remote storage database, a memory device of a remote computing device, cloud storage, etc.).

Figure 16:
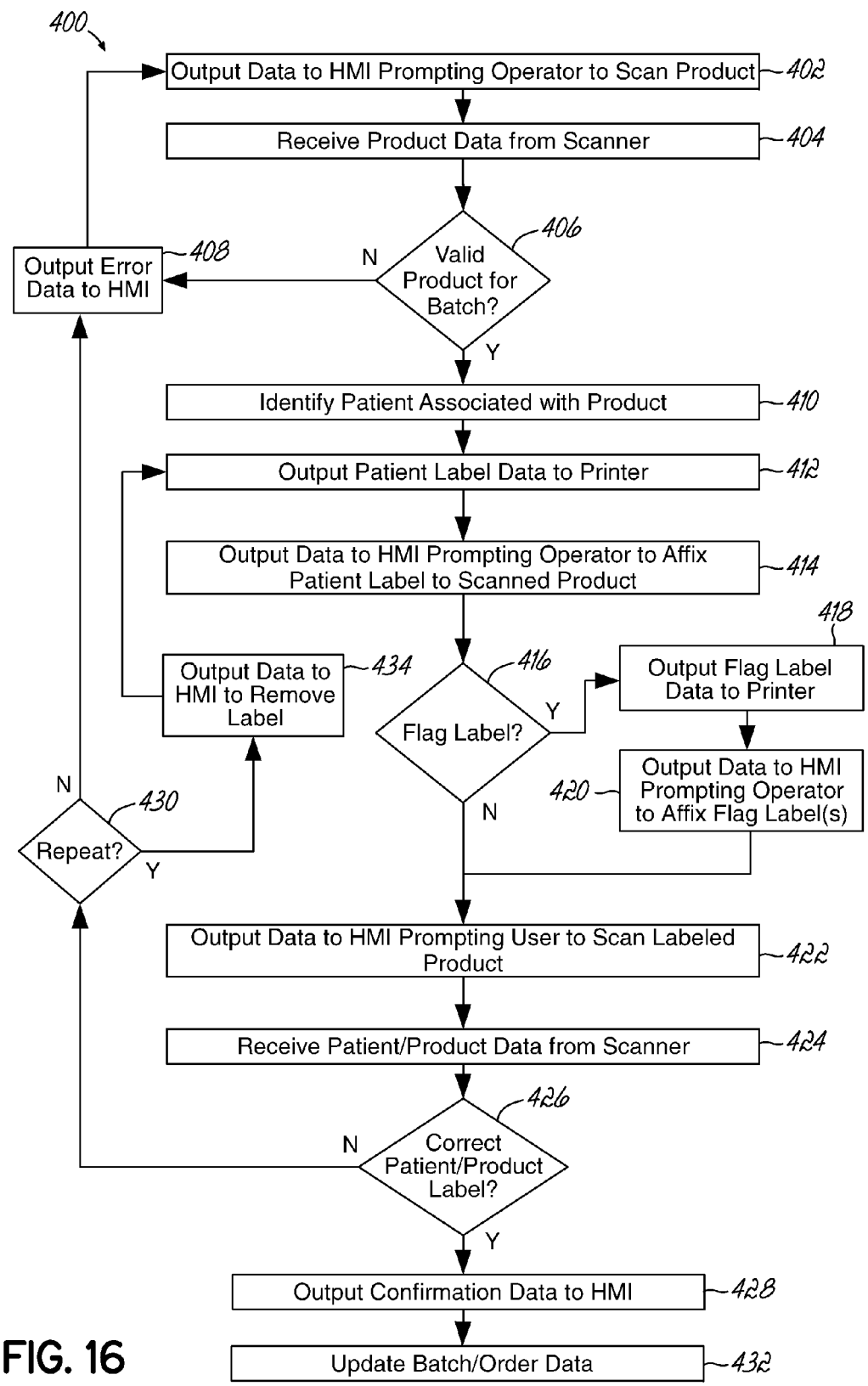
FIG. 16 is a flowchart illustrating a sequence of operations that may be performed by the LVK, ULV system and/or pharmacy host server of FIG. 15 to label and verify a unit of a product consistent with some embodiments of the invention.

Turning now to FIG. 16, this figure provides flowchart 400 that provides a sequence of operations that may be performed by the LVK 104 consistent with some embodiments of the invention to label and verify products for filling a customer order by an operator. The processor 300 associated with the LVK 104 outputs data to the display 32 associated with the LVK 104 prompting the operator to scan a product for the active order (block 402). The operator may scan a product for labeling and verification using the scanner 36 associated with the LVK 104, and the processor 300 may receive product data from the scanner 36 (block 404), where the product data indicates a product. The processor 300 analyzes the received product data to determine whether the product is valid for a customer order being filled using the LVK 104 (i.e., an active order) (block 406). In response to determining that the product indicated by the received product data is not in the active order ("N" branch of block 406), the processor 300 outputs error data to the HMI 180 and/or display 32 (block 408), such that the display 32 indicates to the operator that the scanned product is not correct/valid for the active order, and the display may instruct the operator to place the invalid product in a reject bin or other location.

In response to determining that the product indicated by the received product data is in the active order ("Y" branch of block 406), the processor 300 identifies a patient associated with the product from the order data (block 410), and the processor 300 outputs patient label data based on the identified patient to the printer 44 associated with the LVK 104 such that the printer prints a patient label (block 412). The processor 300 outputs data to the HMI 180 such that the display 32 prompts the operator to affix the patient label to the scanned product (block 414).

The processor 300 determines whether the scanned product is a flag label product (block 416). In some embodiments, the processor 300 may receive input data from the HMI 180 indicating whether the product is a flag label product as well as the number of flag labels needed to flag label the medical items in the scanned product. In some embodiments, the kiosk may access a product record 362 corresponding to the scanned product to determine whether the scanned product is a flag label product as well as the number of flag labels required for the scanned product. In response to determining that the scanned product is a flag label product ("Y" branch of block 414), the processor 300 outputs flag label data based at least in part on the product record 362 and/or the order data to the flag label printer 46 associated with the LVK 104 (block 418), such that flag labels are printed at the flag label printer 46 for the scanned product. The processor 300 outputs data to the HMI 180 prompting the operator to affix the one or more printed flag labels (block 420). The operator may affix a flag label to one or more medical items included in the product, and in some embodiments, the operator may interface with the LVK 104 via the HMI 180 to indicate when such affixing is completed.

The processor 300 outputs data to the HMI 180 such that the display 32 prompts the operator to scan the labeled product (i.e., the product barcode and the patient barcode) (block 422). The processor 300 receives product data and patient data from the scanner (block 424) based on the scanned product barcode and the scanned patient barcode. The processor 300 determines whether the correct patient label is affixed to the correct product (block 426), i.e., the processor 300 verifies the correct labeling of the product. In some embodiments of the invention, the processor 300 compares the patient data and product data received from the scanner to the order data to determine whether the correct patient label is affixed to the correct product.

In response to determining that the correct patient label is on the labeled product based on the received patient data and product data ("Y" branch of block 426), the processor 300 outputs data to the HMI 180 such that the display 32 informs the user that the labeled product has been verified (block 428). In response to determining that the patient label affixed to the scanned product is incorrect ("N" branch of block 426), the processor 300 determines whether to repeat the labeling of the product and the verification scan (block 430). In some embodiments, the labeling and verification may be repeated a predetermined number of times such that a failure to verify a labeled product due to an incorrect printing of a label and/or an incorrect scan with the scanners 36 may be minimized. For example, in some embodiments, the processor 300 may prompt the operator to re-verify the labeled product up to 3 times before determining that the operator should not use the scanned product. In other embodiments, the processor 300 may prompt the operator to re-label and subsequently verify the re-labeled product up to 3 times before determining that the operator should not use the scanned product. In response to determining that the label and verification should be repeated ("Y" branch of block 430), the processor 300 outputs data to the HMI 180 such that the display instructs the operator to remove the affixed patient label (block 434) or cover up the recently applied label with a fully opaque cover up label, and the processor repeats the label and verification operations (blocks 412 through 426). In response to the number of verification scans exceeding the predetermined number ("N" branch of block 430), the processor 300 outputs error data to the HMI 180 such that the display 32 informs the operator that the patient label cannot be verified for the scanned product and prompts the user to place the scanned product in a rejection location and/or bin (block 408), and the processor prompts the user to rescan the product (block 402). Alternatively in some embodiments, if the label and verification process is started by scanning the product, if the system does not see a verification scan (patient label and product label) within a set time period (15 seconds, for example), the patient label is assumed to not be applied and the transaction will be invalidated. The operator will be prompted to place the label in a label destruction bin and the product into a non-labeled reject bin for later restocking.

Following verification of the product, the processor 300 updates batch and/or order data to indicate that the product has been labeled and verified (block 432). As will be discussed herein, following verification and update of the batch and/or order data, the LVK 104 consistent with embodiments of the invention may prompt the operator to scan another product, indicate that a customer order is complete, instruct the operator to place the verified product in a particular tote 56, update one or more records in one or more databases, and/or actuate an associated storage carousel 108 to allow the operator to retrieve another product required in the customer order.

Figure 17:
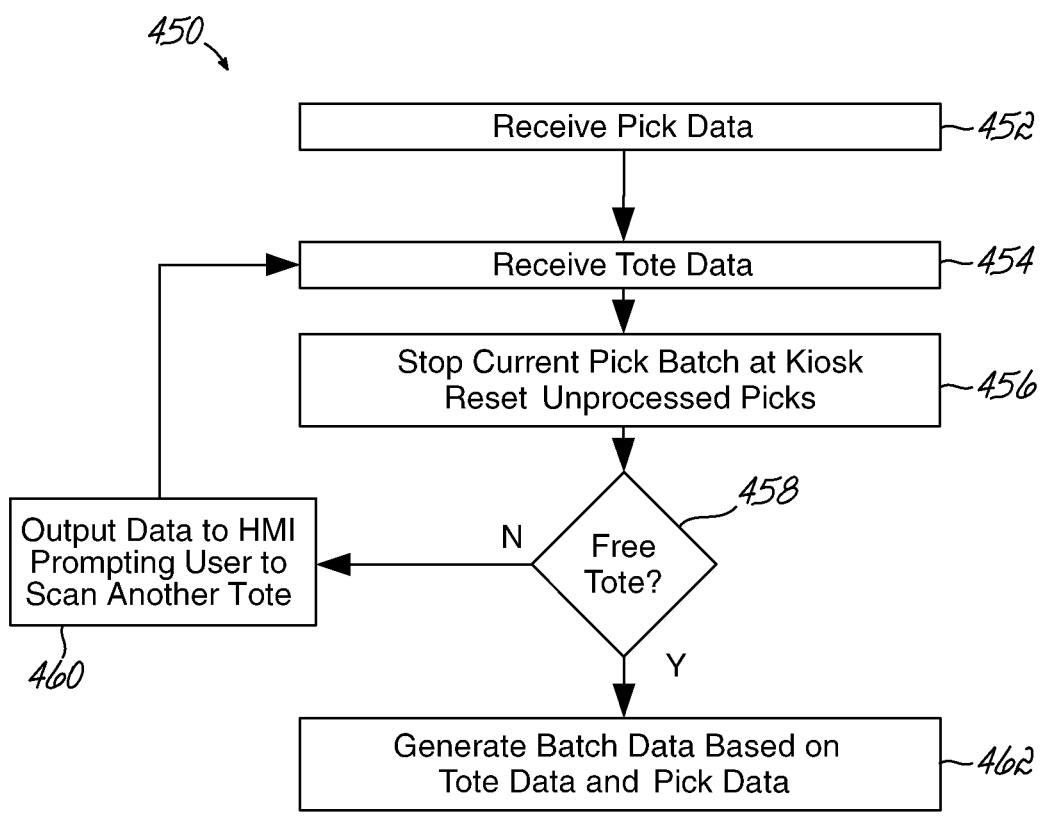
FIG. 17 is a flowchart illustrating a sequence of operations that may be performed by the LVK, ULV system and/or pharmacy host server of FIG. 15 to generate batch data consistent with some embodiments of the invention.

FIG. 17 provides flowchart 450, where the flowchart 450 illustrates a sequence of operations that may be performed consistent with embodiments of the invention to generate batch data for an empty tote 56 at the LVK 104 for a customer order. The processor 300 of the LVK 104 receives pick data indicating one or more products that are to be labeled and verified for the customer order (block 452). An operator may scan a machine readable indicia (e.g., tote bar code 60) associated with the tote 56 using one or more scanners associated with the LVK 104, and the processor 300 receives tote data from the scanners (block 454). In response to receiving tote data from the scanners, the processor 300 ends the current batch being processed and resets unprocessed picks in the batch data (block 456). The processor 300 determines whether the tote 56 is associated with other batch data (i.e., whether the tote is assigned to another customer order) (block 458). In some embodiments, the processor 300 accesses a tote database 354 and analyzes a tote record 360 corresponding to the tote 56 to determine whether the tote 56 is logically free or associated with another customer order. In response to determining that the tote 56 is associated with other batch data ("N" branch of block 458), the processor outputs data to an HMI 180 associated with the LVK 104 such that the display 32 indicates that the scanned tote 56 is not logically free and prompts the operator to scan another tote 56 (block 460). In response to determining that the tote 56 is free ("Y" branch of block 458), the processor 300 generates batch data for the scanned tote 56 based on the tote data, the corresponding tote record 360 and/or the pick data (block 462).

Therefore, in embodiments of the invention that may perform the sequence of operations illustrated in FIG. 17, batch data may be generated for the particular tote 56, such that the tote 56 may be packed with labeled and verified products for a customer order. Moreover, when the tote 56 becomes full, an operator may scan another empty tote 56, and any unprocessed picks (i.e., products) remaining in the batch data of the filled tote 56 may be reassigned to the empty tote 56 by generating the batch data for the empty tote 56.

Figure 18:
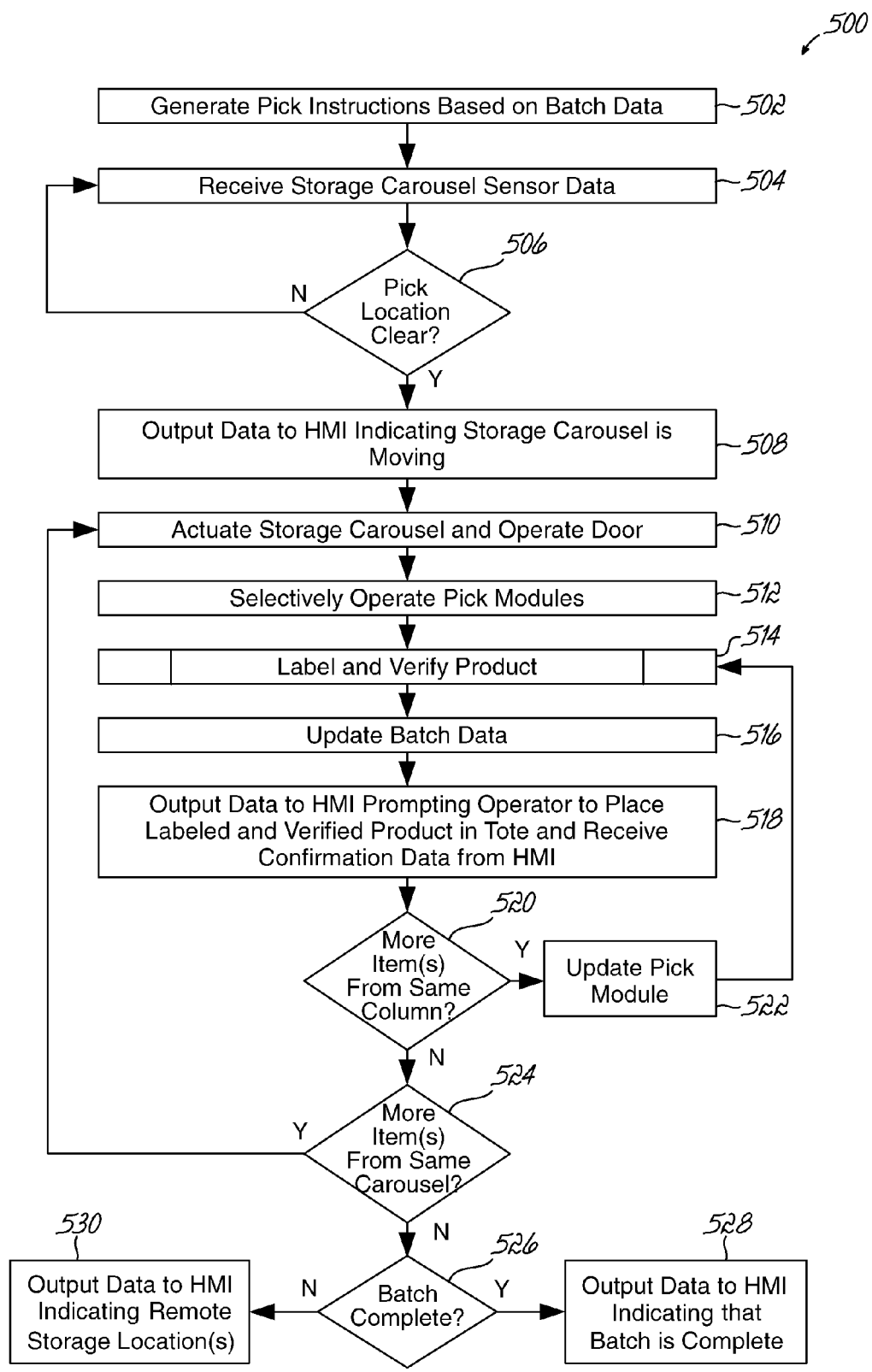
FIG. 18 is a flowchart illustrating a sequence of operations that may be performed by the LVK, ULV system and/or pharmacy host server of FIG. 15 to retrieve, label, and verify units of products consistent with embodiments of the invention.

Turning now to FIG. 18, this figure provides flowchart 500, and flowchart 500 illustrates a sequence of operations that may be performed by the LVK 104 consistent with some embodiments of the invention to facilitate retrieval, labeling and verification of a product for a customer order. The processor 300 associated with the LVK 104 generates pick instructions for the storage carousel 108 associated with the LVK 104 based on batch data (block 502). The pick instructions generally correspond to the interface between the processor 300 and the carousel drive controller 320 and the interface between the processor 300 and the pick indicator logic 326. In these embodiments of the invention, the pick instructions may cause the processor 300 to interface with the drive controller 320 to thereby cause the drive controller 320 to operate the motor 146 connected to the storage carousel 108 to thereby rotate the storage carousel 108 such that products of the active order are positioned in the pick location 130. Furthermore, the pick instructions may cause the processor 300 to interface with the pick indicator logic 326 to cause the pick indicator logic to selectively operate pick modules 114, to indicate specific storage bins 140 from which the operator is supposed to retrieve products for the active order. For example, in some embodiments, the pick instructions may preclude aligning particular storage bins 140 to the pick location 130 based on the operator's permission level associated with controlled substances such that controlled substances of one or more classes may not be accessible by the operator. In addition, generating the pick instructions may be based on a stock management policy, including for example, a FIFO policy or a FEFO policy. In such embodiments, if a product is stored in more than one storage bin 140, the storage bin 140 storing units of the product having the earliest expiration date will be utilized to fill a batch to thereby reduce stock loss due to expiration.

The processor 300 receives sensor data from one or more sensors associated with the storage carousel 108 (block 504), and the sensor data may be analyzed by the processor to determine whether the pick location 130 is clear (i.e., whether the operator and/or another object is clear of the pick location 130) (block 506). In these embodiments, the processor 300 determines whether the pick location 130 is clear to prevent injury to the operator and/or damage to other objects when rotating the storage carousel 108. In response to determining that the pick location 130 is not clear ("N" branch of block 506), the processor 300 continues receiving sensor data (block 504). In response to determining that the pick location 130 is clear ("Y" branch of block 506), the processor 300 outputs data to an HMI 180 associated with the LVK 104 such that an associated display 32 informs the operator that the storage carousel 108 is preparing to rotate (block 508). The processor 300 interfaces with the drive controller 320 to cause the storage carousel 108 to rotate and thereby align the vertical storage column 165 to the pick location 130 and to operate the door 122 (i.e., close the door 122 before rotating the storage carousel 108 and open the door 122 after rotation is complete) (block 510), where at least one storage bin 140 of the vertical storage column 165 aligned to the pick location 130 stores a product included in the customer order/batch data. The processor 300 interfaces with the pick indicator logic 326 to selectively operate one or more pick modules 114 corresponding to one or more particular products in the order (block 512).

The LVK 104 performs the sequence of operations described above in flowchart 400 of FIG. 16 to label and verify a product retrieved from the aligned storage location (block 514). After label and verification of a first product in the batch data, the processor 300 updates the batch data (block 516). The processor 300 outputs data to the HMI 180 such that the display 32 instructs the operator to place the labeled and verified first product in a shipping tote 56 associated with the batch data, and the processor 300 may optionally receive input data from the HMI 180 confirming that the labeled and verified product has been deposited into the tote 56 (block 518). Following the confirmation (when applicable), the processor 300 determines whether more units of one or more products in the batch data are stored in the aligned vertical storage column 165 (block 520). In response to determining that one or more items (i.e., one or more units of one or more products) stored in the aligned vertical storage column 165 still need to be labeled and verified for the batch ("Y" branch of block 520), the processor updates the pick module 114 based on the updated batch data (block 522). For example, if the a first item from the first storage bin 140 was labeled and verified and the batch data updated, and no more items were required from the first storage bin 140, the pick module 114 associated with the first storage bin 140 may be extinguished (i.e., turned off). However, if more items were required from the first storage location, the pick module 114 associated with the first storage bin 140 may be updated to reflect the remaining quantity of units in the batch data needed from the first storage bin 140. After updating the pick module 114, the LVK 104 performs the operations described above with respect to blocks 514 through 520, until all items stored in the aligned vertical storage column 165 have been labeled, verified, and placed in the tote 56 ("N" branch of block 520). The processor 300 determines whether any more items in the batch data are stored in the storage carousel (block 524).

In response to determining that one or more items of the batch data are stored by the storage carousel 108 ("Y" branch of block 524), the processor 300 actuates the storage carousel 108 to align another vertical storage column 165 including storage bins 140 storing at least one needed item (block 510). The processor 300 and LVK 104 perform the operations described in blocks 510 through 524 until all items of the batch data stored by the storage carousel 108 have been labeled, verified, and placed in the tote 56 ("N" branch of block 524). Once all items from the storage carousel 108 in the batch data have been labeled, verified, and placed in the tote 56 ("N" branch of block 524), the processor 300 determines whether all items in the batch data have been processed (i.e., labeled, verified, and placed in the tote 56) (block 526). In response to determining that all items in the batch have been processed ("Y" branch of block 526), the processor 300 outputs data to the HMI 180 such that the display 32 indicates that the batch is complete and/or provides instructions to the operator on what to do with the tote 56 (block 528).

In response to determining that one or more items in the batch data have not been processed (i.e., labeled, verified, and placed in the tote), the processor 300 determines remote storage locations at which the unprocessed items in the batch data may be located, and the processor 300 outputs data to the HMI such that the display 32 informs the operator of such remote locations (block 530). For example, one or more unprocessed items in the batch data may be located at a second LVK 104 having a storage carousel 108, and the processor 300 may access the product database 356 and/or storage database 306 to identify the second LVK 104, and the processor 300 may output data to the HMI 180 such that the display 32 identifies the second LVK 104. In this example, the operator may take the tote 56 to the second kiosk 104 and scan the machine readable indicia 60 associated with the tote 56, and the second LVK 104 would retrieve the batch data associated with the tote 56 and operate to move any items of the batch data stored at the second kiosk 104 to the operator for retrieval, labeling, and verification as previously described. As another example, one or more items may be located in a remote shelf, and the operator may be provided information that identifies the remote shelf.

Figure 19:
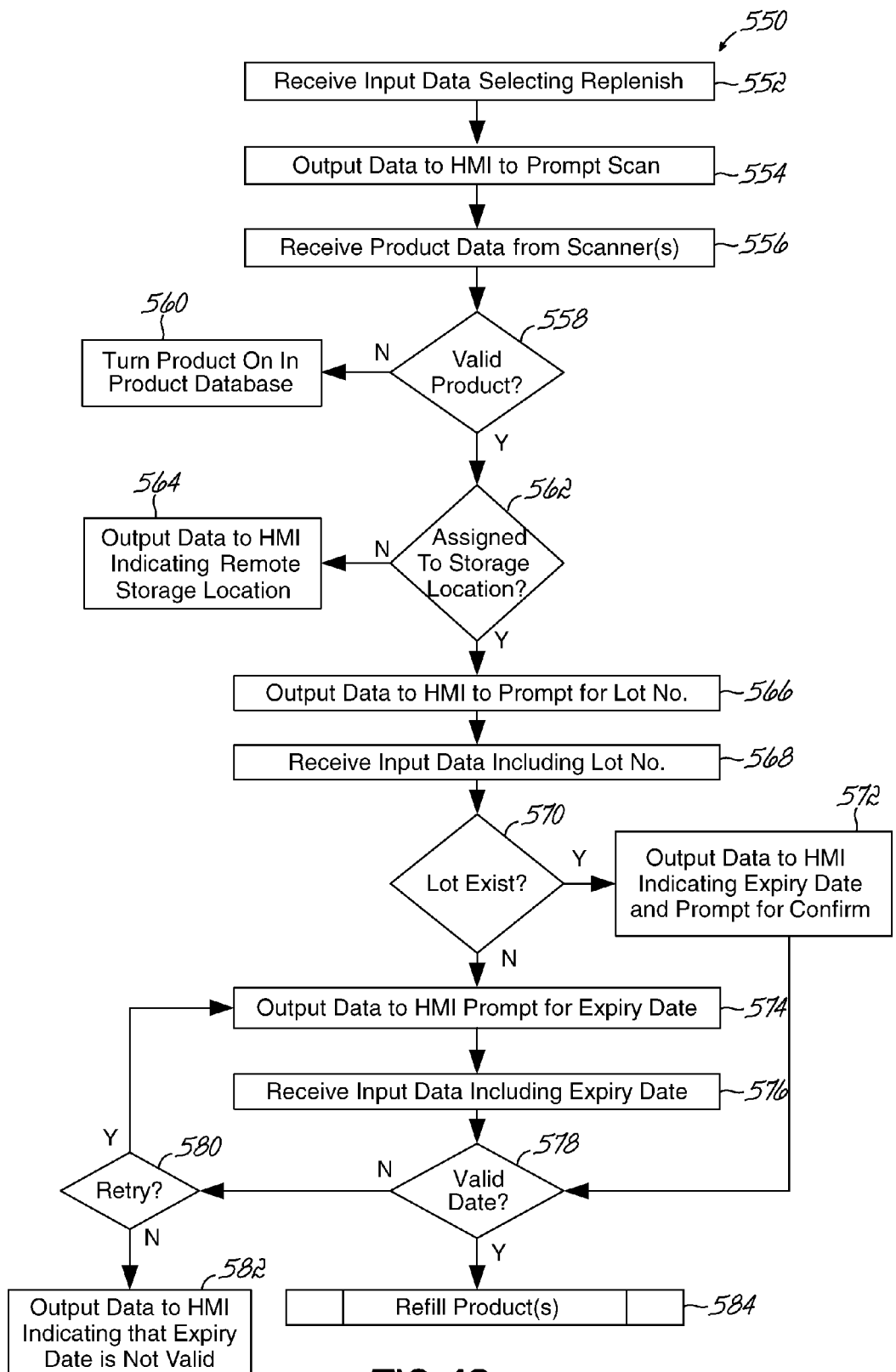
FIG. 19 is a flowchart illustrating a sequence of operations that may be performed by the LVK, ULV system and/or pharmacy host server of FIG. 15 to facilitate replenishment of products consistent with embodiments of the invention.

FIG. 19 provides flowchart 550 which illustrates a sequence of operations that may be performed by the LVK 104 consistent with embodiments of the invention to perform replenishment and refill operations for the storage carousel 108 associated with the LVK 104. The processor 300 associated with the LVK 104 receives input data indicating that an operator is going to replenish the storage carousel 108 (block 552). The processor 300 outputs data to an HMI 180 associated with the LVK 104 such that the display 32 associated with the HMI 180 prompts the operator to scan a product (block 554). The operator may scan a product using one or more scanners 36 associated with the LVK 104, and the processor 300 may receive product data from the scanners 36 (block 556). In some embodiments, the scanner may be the hand-held scanner 74 and/or an array of scanners 36. Similarly, the display may be associated with the LVK 104 and/or with the hand-held scanner 74.

The processor 300 analyzes the received product data to determine whether the product is a valid product for a pharmacy host server in communication with the LVK 104 (block 558). In some embodiments, the processor 300 may access and/or query the product database 356 stored at the pharmacy host server to determine whether the product is a valid product. In response to determining that the product is not a valid product ("N" branch of block 558), the processor 300 may "turn on" the product in the product database based on the received product data and/or user input data provided at the LVK 104 and/or the pharmacy host server (block 560). "Turning on" the product may include generating the product record 362 and storing the product record 362 in the product database 356.

In response to determining that the scanned product is a valid product ("Y" branch of block 558), the processor 300 determines whether the product is assigned to the storage bin 140 in the storage carousel 108 associated with the LVK 104 (block 562). In such embodiments, the processor 300 may analyze the storage database 306 and/or the product database 356 to determine whether the product is assigned to the storage bin 140. In response to determining that the product is not assigned to a storage location of the associated storage carousel 108 ("N" branch of block 562), the processor 300 outputs data to the HMI 180 such that the associated display 32 indicates a remote storage location at which the product may be stocked (block 564). In response to determining that the scanned product is assigned to the storage bin 140 in the storage carousel 108, the processor 300 outputs data to the HMI 180 such that the display 32 prompts the operator to input a lot number associated with the scanned product (block 566). The operator may input the lot number via the HMI 180, and the processor 300 receives the input data from the HMI 180 including the lot number (block 568). The processor 300 determines whether the lot number of the product has been previously input in to the pharmacy host server (block 570).

In response to determining that the lot number exists ("Y" branch of block 570), the processor 300 outputs data to the HMI 180 and the display 32 indicates an expiry date associated with the existing lot number and prompts the operator to confirm the expiry date (block 572). In response to determining that the lot number of the product does not exist ("N" branch of block 570), the processor 300 outputs data to the HMI 180 and the display 32 prompts the operator to input an expiry date associated with the scanned product and lot number (block 574). The operator may input an expiry date associated with the product via the HMI 180, and the processor 300 may receive the input data including the expiry date (block 576). Following input or confirmation of the expiry date, the processor 300 determines whether the expiry date is a valid date (block 578). In embodiments of the invention, products may not be stocked in a storage location if the expiry date is within a given time from the date that the replenishment is occurring. For example, in some embodiments, an expiry date that falls within 45 days, for example, of the date at which the operator is attempting to stock the associated product may be determined to be invalid. In this manner, the kiosk may control inventory and expiry dates to prevent significant stock loss due to expiry of the products.

In response to determining that the expiry date is not valid ("N" branch of block 578), the processor 300 may determine whether to retry the input and evaluation of the expiry date (block 580), and in response to determining to retry the input and evaluation the processor 300 may repeat the operations described in blocks 574 through 578. After retrying the input and evaluation of the expiry date a predetermined number of times ("N" branch of block 580), the processor 300 outputs data to the HMI 180 such that the display 32 indicates to the operator that the expiry date is not valid and the product cannot be stocked (block 582). In response to determining that the expiry date is valid ("Y" branch of block 578), the LVK 104 may perform operations associated with refilling the product as described in FIG. 20 (block 584).

Figure 20:
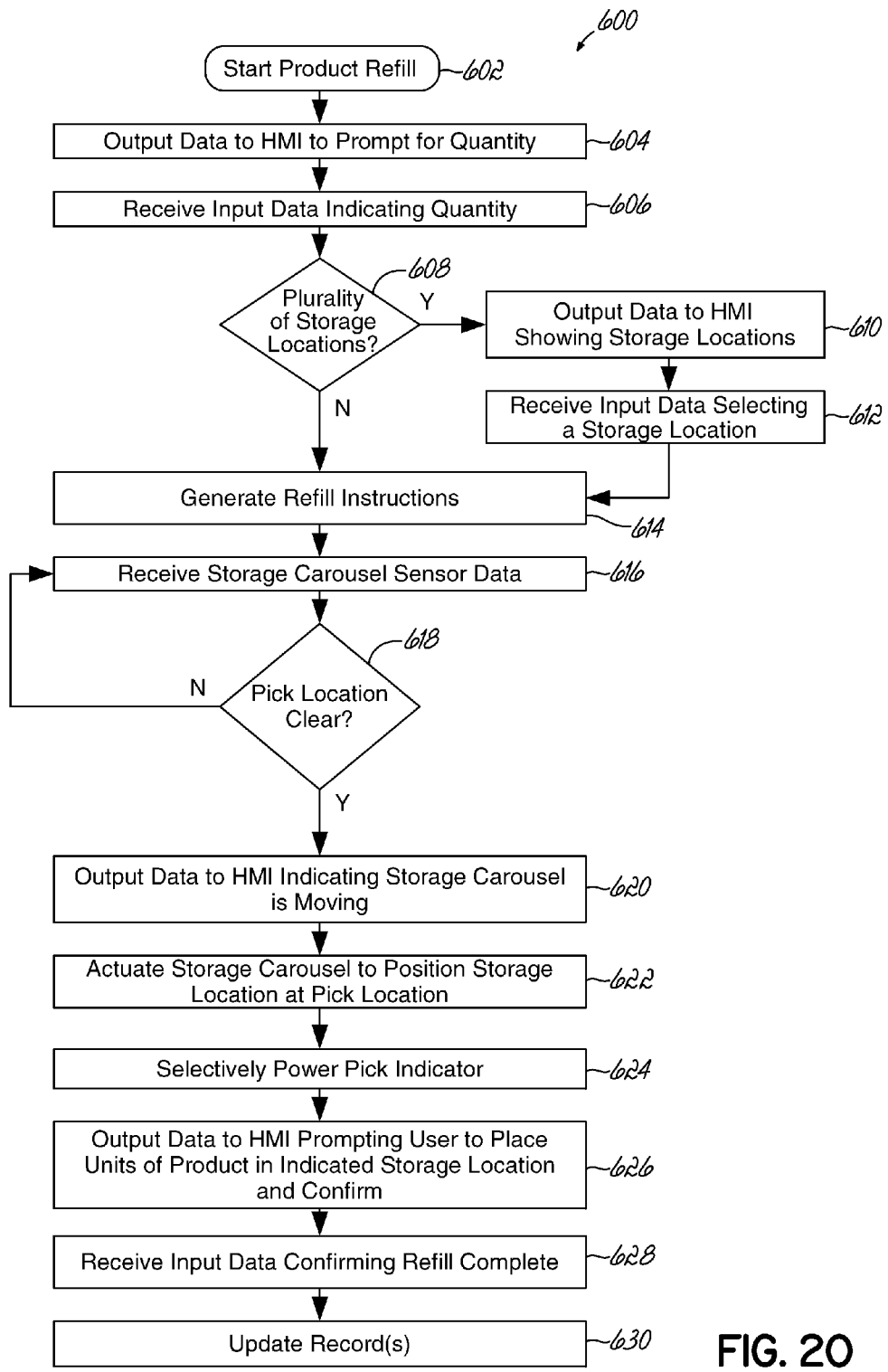
FIG. 20 is a flowchart illustrating a sequence of operations that may be performed by the LVK, ULV system and/or pharmacy host server of FIG. 15 to facilitate replenishment of products consistent with embodiments of the invention.

FIG. 20 provides a flowchart 600 that illustrates a sequence of operations that may be performed by the LVK 104 consistent with embodiments of the invention to facilitate an operator refilling a product after providing information associated with the product as described in flowchart 550 of FIG. 19. A product refill is initialized at the LVK 104 (block 602). The processor 300 associated with the LVK 104 outputs data to an HMI 180 associated with the kiosk such that the display 32 in communication with the HMI 180 prompts an operator to input a quantity of units of the product to be refilled (block 604). The operator may input a quantity of units of the product to be refilled in the storage carousel 108 associated with the LVK 104, and the processor 300 may receive the input data indicating such quantity (block 606). The processor 300 determines whether the product is assigned more than one storage bins 140 on the storage carousel 108 associated with the LVK 104 (block 608). In some embodiments, the processor 300 may access and/or query the product database 356 and/or the storage database 306 to determine whether the product is assigned to the plurality of storage bins 140 on the storage carousel 108 associated with the LVK 104.

In response to determining that the product is stored in the plurality of storage bins 140 ("Y" branch of block 608), the processor 300 outputs data to the HMI 180 such that the display 32 graphically displays a representation of the plurality of storage bins 140 (block 610). The operator may select a particular storage bin 140 via the HMI 180, and the processor 300 may receive input data indicating the selected storage bin 140 (block 612). Based on the selected storage bin 140, the processor 300 generates refill instructions (block 614). The refill instructions generally correspond to an interface between the processor 300 and the drive controller 320 connected between the motor 146 of the storage carousel 108 and the processor 300, and the refill instructions further generally correspond to an interface between the processor 300 and pick indicator logic 326 connected between pick modules 114 and the processor 300. According to the pick instructions, the processor 300 interfaces with the drive controller 320 and the pick indicator logic 326 to rotate the storage carousel 108 to align the vertical storage column 165 including the selected storage bin 140 to the pick location 130 accessible by the operator and to selectively operate the particular pick module 114 to indicate the selected storage bin 140 for the operator.

The processor 300 receives sensor data from one or more sensors 132 associated with the storage carousel 108 (block 616), and the sensor data may be analyzed by the processor to determine whether the pick location 130 is clear (i.e., whether the operator and/or another object is clear of the pick location 130) (block 618). In response to determining that the pick location 130 is not clear ("N" branch of block 618), the processor 300 continues receiving sensor data (block 616). In response to determining that the pick location 130 is clear ("Y" branch of block 618), the processor 300 outputs data to an HMI 180 associated with the LVK 104 such that an associated display 32 optionally informs the operator that the storage carousel 108 is preparing to rotate (block 620). The processor 300 interfaces with the drive controller 320 to cause the storage carousel 108 to rotate and thereby align the vertical storage column 165 including the selected storage bin 140 to the pick location 130 (block 622). The processor 300 interfaces with the pick indicator logic 326 to selectively operate the pick module 114 corresponding to the selected storage bin 140 (block 624).

The processor 300 outputs data to the HMI 180 such that the display 32 prompts the user to place the scanned product in the indicated storage bin 140, and the display 32 requests the user to confirm when stocking is complete via the HMI 180 (block 626). The operator provides confirmation of completing the stocking of the scanned product, and the processor 300 receives input data from the HMI 180 confirming the completion (block 628). In response to receiving the confirmation, the processor 300 updates one or more records (block 630), including, for example, the product record 362 associated with the scanned product, the bin record 328 associated with the selected storage bin 140, an operator record 366 associated with the operator, and/or other such records.

Figure 21:
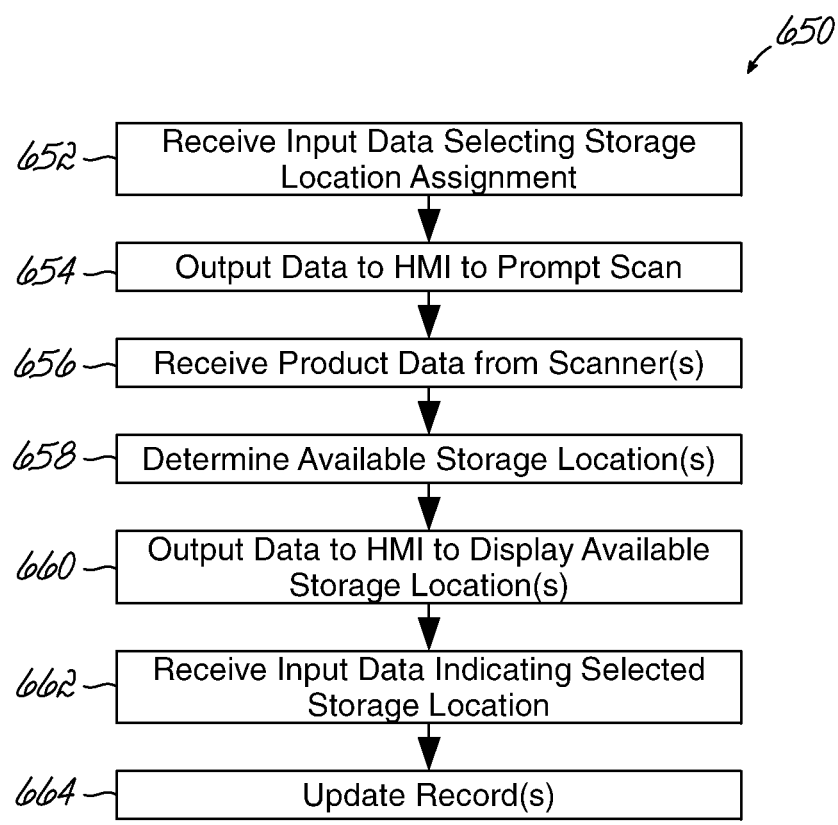
FIG. 21 is a flowchart illustrating a sequence of operations that may be performed by the LVK, ULV system and/or pharmacy host server of FIG. 15 to assign a product to a storage bin consistent with embodiments of the invention.

FIG. 21 provides flowchart 650, where the flowchart 650 illustrates a sequence of operations that may be performed by the LVK 104 and/or pharmacy host server 110 consistent with some embodiments of the invention to assign a product to a storage bin 140 of the storage carousel 108 associated with the LVK 104. An operator may select via an HMI 180 associated with the LVK 104 to select the storage bin 140 for assignment, and the processor 300 associated with the LVK 104 may receive input data from the HMI 180 selecting to perform a storage location assignment (block 652). In response to receiving input data selecting to perform a storage location assignment, the processor 300 outputs data to the HMI 180 such that the display associated with the HMI 180 prompts the operator to scan a product (block 654). The operator may scan the product with the plurality of scanners 36 arranged on the LVK 104 and/or the operator may utilize the hand-held wireless scanner 74 in communication with the LVK 104. The processor 300 receives product data from the scanner 36 (block 656), and the processor 300 determines available storage bins 140 on the associated storage carousel 108 (block 658). In these embodiments, the processor 300 may access/query the storage database 306 to determine available storage bins 140 on the associated storage carousel.

The processor 300 outputs data to the HMI 180 such that the display graphically presents to the operator all storage bins 140 available on the associated storage carousel 108 (block 660). The operator may select a particular available storage location, and the processor 300 may receive input data indicating such selection (block 662). In some embodiments, the operator may select the particular storage location via the HMI 180, and the processor may receive input data from the HMI 180 indicating such selection. Alternatively, in some embodiments, the operator may utilize the wireless hand scanner 74 to select the particular storage bin 140 by scanning the machine readable indicia associated with (e.g., barcode 162) the particular storage bin 140 using the hand scanner 74, and the processor 300 may receive input data from the hand scanner 74 indicating such selection. The processor 300 updates one or more databases based on the selected storage location (block 664), including, for example, the product database 356 and/or the storage database 306.

Figure 22:
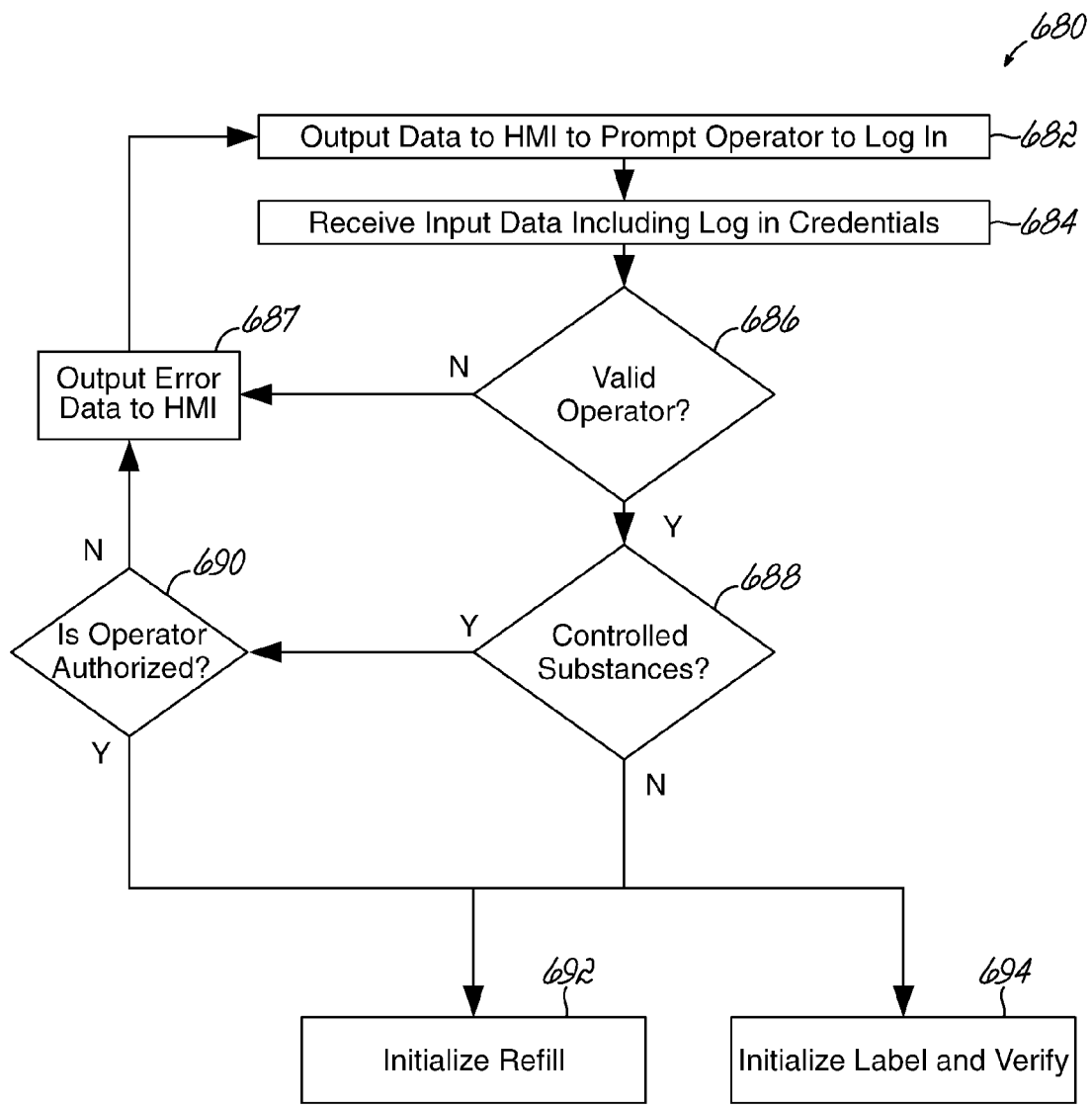
FIG. 22 is a flowchart illustrating a sequence of operations that may be performed by the LVK, ULV system and/or pharmacy host server of FIG. 15 to log-in an operator consistent with embodiments of the invention.

Turning now to FIG. 22, this figure provides flowchart 680, which illustrates a sequence of operations that may be performed by the LVK 104 and/or pharmacy host server 110 consistent with some embodiments of the invention to allow an operator to log-in to the LVK 104. The processor 300 associated with the LVK 104 outputs data to an associated HMI 180 such that the display 32 associated with the HMI 180 prompts the operator to log-in (block 682). The operator may supply log-in credentials via the HMI 180 and/or other data input device, and the processor 300 may receive input data including the log-in credentials (block 684). In some embodiments, the operator may type in a user name and password via the HMI 180. In some embodiments, the operator may scan a security device using the scanner 36 associated with the LVK 104 (i.e., a badge, ID card, key fob, biometric registration, etc.), and the operator may type in a pin number. Other such known methods for identification verification may be utilized.

The processor 300 determines whether the log-in credentials match a valid operator (block 686). In these embodiments, the processor 300 may access/query an operator database 357 to determine whether the log-in credentials match a valid operator. In response to determining that the log-in credentials do not match a valid operator ("N" branch of block 686), the processor 300 outputs error data to the HMI 180 such that the display indicates to the operator that the log-in credentials are not valid (block 687), and the LVK 104 repeats the sequence of operations described in blocks 682 through 686. In response to determining that the log-in credentials match a valid operator ("Y" branch of block 686), the processor 300 determines whether an operation which the operator is attempting to perform with the LVK 104 includes one or more controlled substances (block 688).

In response to determining that the operation that the operator is attempting to perform with the LVK 104 includes controlled substances ("Y" branch of block 688), the processor determines whether the operator is authorized to perform operations including one or more desired classes of controlled substances (block 690). In some embodiments of the invention, the processor 300 may access/query the operator database 357 to determine a controlled substances authorization level, where the level may indicate if the operator is authorized to perform operations with one or more classes of controlled substances. For example, an operator may be authorized to perform operations with class III-V controlled substances but not class II controlled substances. In this example, if the operator were attempting to refill a class II controlled substance at the LVK 104, the processor 300 would determine that the operator is not authorized. Furthermore, in some embodiments of the invention, the storage carousel 108 associated with the LVK 104 may store products including different classes of controlled substances, and the processor 300 may not allow the operator access to storage bins 140 storing particular classes of controlled substances that the operator is not authorized to access. In some embodiments of the invention, controlling access to such storage bins 140 may include automatically closing the motorized security door 128 associated with the cage 106 to thereby close the pick location 130. In some embodiments, controlling access may include generating pick instructions that do not allow the storage carousel 108 to align the vertical storage column 165 that includes one or more storage bins 140 storing controlled substances that the operator is not authorized to access to the pick location 130, as described in detail above.

In response to determining that the operator is not authorized to perform the desired operation for one or more desired classes of controlled substances ("Y" branch of block 690), the processor 300 outputs error data to the HMI 180 such that the display 32 indicates to the operator that the desired operation is not authorized (block 687), and the LVK 104 repeats the operations described in block 682 through 688. In response to determining that the operator is authorized to perform the desired operation for the one or more desired controlled substances ("Y" branch of block 690), or in response to determining that the desired operation does not include any controlled substances ("N" branch of block 688), the LVK 104 may initialize the desired operation, including for example a refill operation (block 692) or a label and verify operation (block 694).

Figure 23:
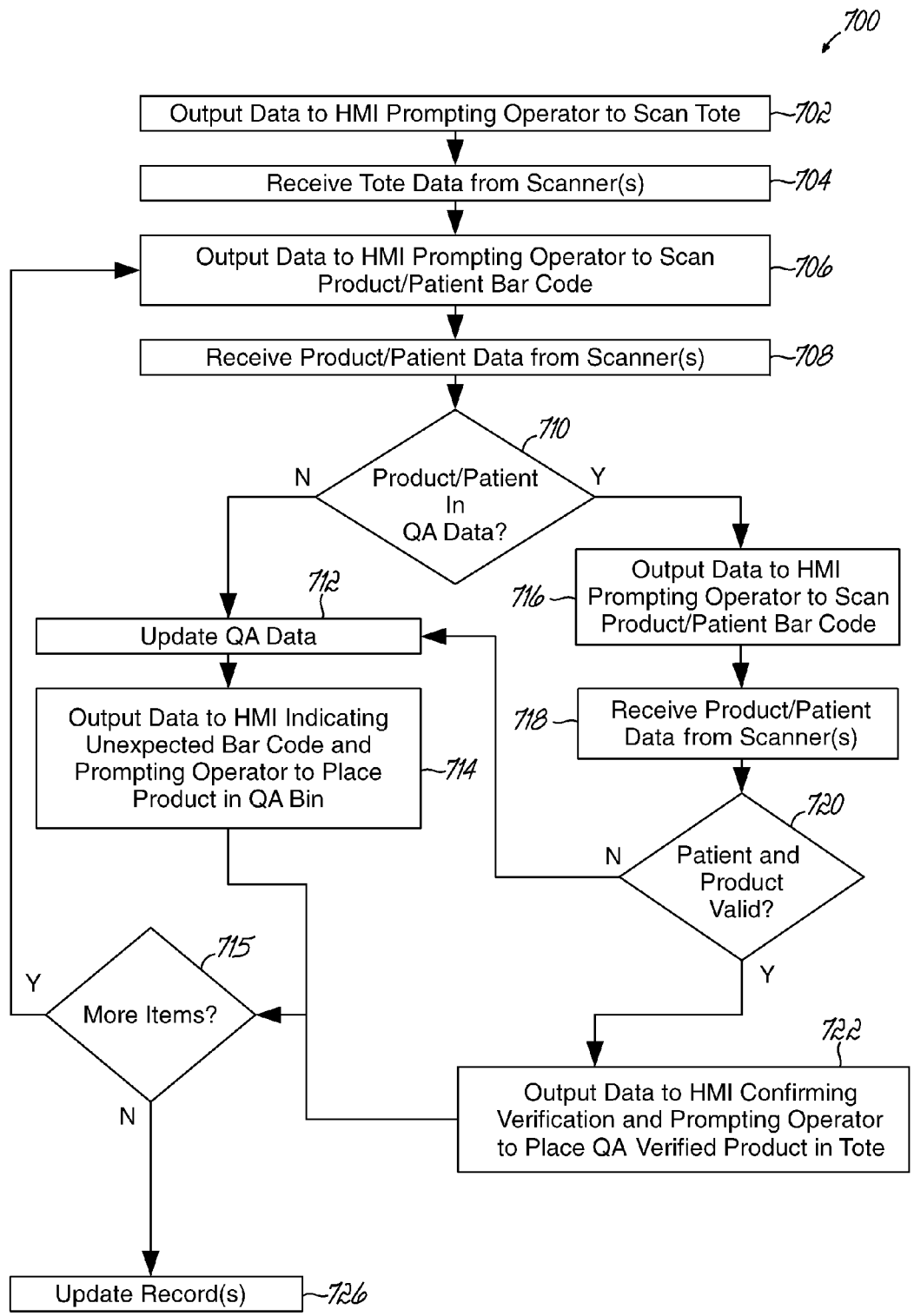
FIG. 23 is a flowchart illustrating a sequence of operations that may be performed by the LVK, ULV system and/or pharmacy host server of FIG. 15 to perform quality assurance on a tote of labeled and verified products consistent with embodiments of the invention.

With reference to FIG. 23, this figure provides flowchart 700, which illustrates a sequence of operations that may be performed by the LVK 104 and/or pharmacy host server 110 consistent with embodiments of the invention to perform quality assurance (QA) operations on a tote 56 of labeled and verified items. These QA operations may occur at another LVK 104 dedicated to such QA operations or at an audit station of an ALV or ULV system. The processor 300, 342 associated with the LVK 104 and/or pharmacy host server 110 may output data to an HMI 180 such that an associated display 32 prompts an operator to scan the tote 56 to start a QA process (block 702). An operator may scan the machine readable indicia with the scanner 36 associated with the kiosk or the hand scanner 74, and the processor 300 may receive tote data from the scanners 36 (block 704). The processor 300 outputs data to the HMI 180 such that the display 32 prompts the operator to scan the product barcode or patient barcode on the first labeled and verified product of the tote 56 (block 706). The operator scans the patient/product barcode, and the processor receives data indicating the patient/product (block 708). The processor determines whether the patient/product indicated in the received data is in QA data associated with the tote 56 (block 710). In these embodiments, the processor 300 may access/query the tote database 354 corresponding to the scanned tote 56 to determine whether the indicated patient/product is in the QA data, where the QA data includes a list of products that should be labeled with particular patient labels in the tote 56.

In response to determining that the indicated patient/product is not in the QA data ("N" branch of block 710), the processor 300 updates the QA data to indicate that an unexpected patient/product was in the tote 56 (block 712), and the processor outputs data to the HMI 180 such that the display 32 indicates that the scanned product/patient was unexpected and prompts the operator to place the scanned product in a QA bin (block 714). The processor 300 determines whether more labeled and verified products in the tote 56 need to be QA processed (block 715). If more products need to be QA processed for the tote 56 ("Y" branch of block 715), the kiosk returns to block 706 and may perform the operations described with respect to flowchart 700 for each of the remaining labeled and verified products.

In response to determining that the indicated product/patient is in the QA data ("Y" branch of block 710), the processor 300 outputs data to the HMI 180 such that the display 32 prompts the operator to scan whichever barcode of the product/patient barcodes was not scanned first (i.e., the relevant barcode) (block 716). The operator scans the relevant barcode with the scanners 36 associated with the LVK 104 or the hand held scanner 74, and the processor 300 receives data indicating the product/patient from the scanners 36, 74 (block 718). The processor 300 determines whether the indicated patient is valid for the indicated product in the QA data (block 720). In response to determining that the patient/product is invalid ("N" branch of block 720), the LVK 104 and/or processor 300 perform the operations described above with respect to blocks 712 through 714. In response to determining that the indicated patient is valid for the indicated product ("Y" branch of block 720), the processor 300 outputs data to the HMI 180 such that the display 32 indicates that the verification has been confirmed and prompts the operator to place the QA verified product in the tote 56 (block 722). The processor 300 determines whether more labeled and verified products in the tote 56 need to be QA verified (block 715). If more products need to be QA processed for the tote 56 ("Y" branch of block 715), the LVK 104 returns to block 706 and may perform the operations described with respect to flowchart 700 for each of the remaining labeled and verified products. When all products of the tote 56 have been QA verified ("N" branch of block 715), the processor 300 may update one or more records in one or more databases (block 726), including, for example, the tote record 360 corresponding to the tote 56 in the tote database 354.

Figure 24:
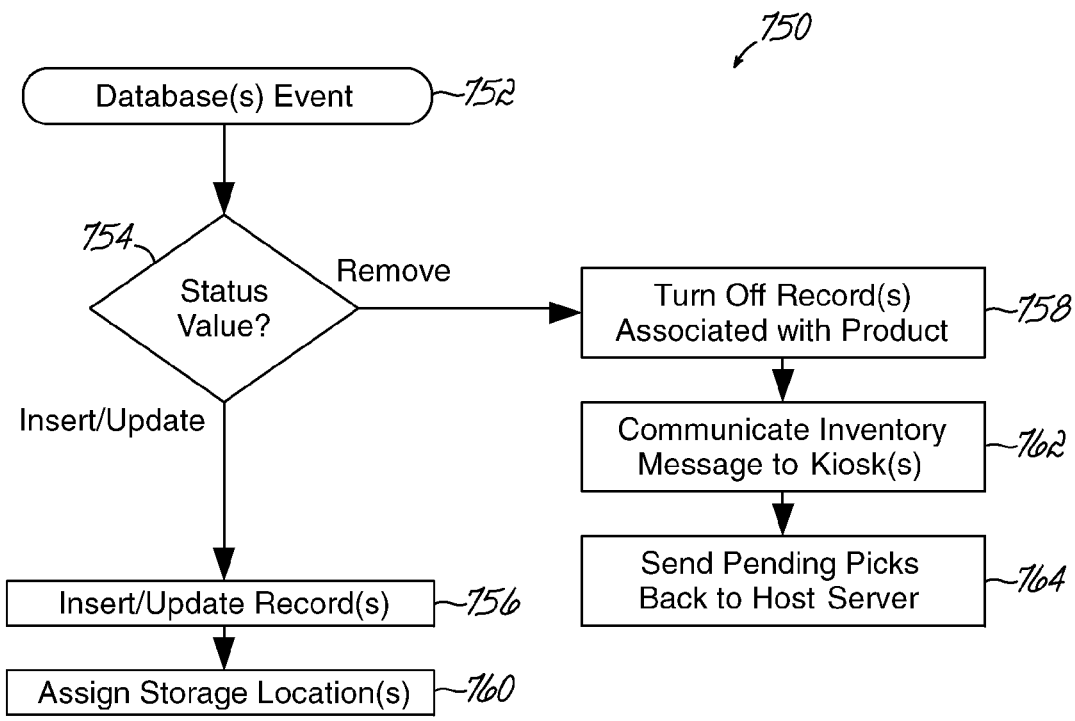
FIG. 24 is a flowchart illustrating a sequence of operations that may be performed by the LVK, ULV system and/or pharmacy host server of FIG. 15 to manage and update database records consistent with embodiments of the invention.

FIG. 24 provides flowchart 750, which provides a sequence of operations that may be performed by one or more LVKs 104 and/or the pharmacy host server 110 consistent with embodiments of the invention to update records and pick data loaded at one or more LVKs 104. An event may occur in a database of the one or more LVKs 104 and/or pharmacy host server 110 (block 752), including, for example, the product record 362 of the product database 356 may be updated, inserted, or removed. In response to the database event, the processor 342 of the pharmacy host server 110 determines the status associated with the database event (block 754).

Based on the determined status, the processor 342 of the pharmacy host server 110 may insert/update one or more records in one or more databases responsive to an insert/update event occurring in the first database (block 756), or the processor 342 of the pharmacy host server 110 may "turn off" one or more records of one or more databases responsive to a remove event occurring in the first database (block 758). In response to an insert/update of one or more records, the processor 342 of the pharmacy host server 110 may assign one or more available storage locations to a product associated with the insert/update (block 760). In response to "turning off" one or more records associated with a particular product, the pharmacy host server 340 may communicate an inventory message to one or more kiosks 104 (block 762), where the inventory message indicates that the "turned off" product may not be labeled and verified for a customer order. In response to receiving the inventory message, the one or more kiosks 104 communicate the picks associated with the "turned off" product back to the pharmacy host server 110 such that the picks will not be filled (block 764).

For example, if a recall is issued for a product, the pharmacy host server 110 may communicate an inventory message to all kiosks 104 storing the recalled product in an associated storage carousel 108 such that none of the recalled lot number will be put into customer orders. As a further example, if a particular lot number of a product expired, the pharmacy host server 110 may communicate an inventory message to all kiosks 104 storing the expired units of product in an associated storage carousel 108 such that the expired units will not be used in filling a customer order. In these embodiments, during generation of the pick instructions, storage bins 140 storing such removed products will not be presented to the operator for retrieval. Hence, in such embodiments, even if the removed product has not yet been physically removed from the storage carousel 108, the removed product will not be used in filling customer orders.

Figure 25:
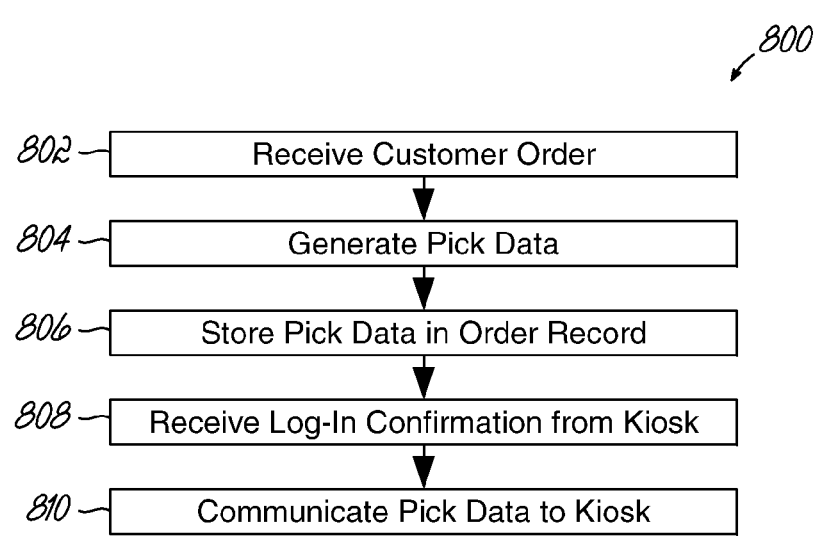
FIG. 25 is a flowchart illustrating a sequence of operations that may be performed by the LVK, ULV system and/or pharmacy host server of FIG. 15 to generate pick data consistent with embodiments of the invention.

As shown in FIG. 25, this figure provides flowchart 800 which illustrates a sequence of operations consistent with embodiments of the invention to receive a customer order and generate pick data for an LVK 10, 104. The pharmacy host server 110 and an associated processor 342 consistent with embodiments of the invention receives a customer order (block 802) and generates pick data based on the customer order (block 804). The pick data includes a patient and each unit of one or more products required for the patient, as indicated in the customer order. The processor 342 stores the pick data in an order record 358 (block 806) until such time as an operator logs in to the LVK 10, 104 to begin processing orders. The processor 342 receives log-in confirmation from the LVK 10, 104 (block 808), and the processor 342 communicates the pick data stored in the order record 358 to the LVK 10, 104 for processing (block 810).

Further logic may be used to ascertain that additional medical items for a particular customer order are in process under pharmacist order review and not released to the pharmacy floor for processing yet (e.g., a portion of the medical items are ready to be filled and labeled, while another portion of the same order is still under review and will be added to the order queue shortly). If this condition is present, particular batches of customer orders may be flagged or held in a suspended state until remaining elements of and/or medication orders are complete with their clinical verification by a pharmacist and released for order fulfillment. This temporary suppression of the customer orders associated with this condition remove fragmenting of orders that can increase the inefficiencies in the filling process.

The ULV process may also include several restocking and replenishment tasks and different levels of priorities for replenishment based on conditions. For instance, the LVK, ULV, CLV, and (optionally) ALV systems in conjunction with the pharmacy host system 110 will keep a complete in-pharmacy inventory count for all medical items used within. This will include a warehouse stock location, a back stock location, and a forward stock location (e.g., at the storage carousels 108). Items received at the receiving dock will be transacted as part of the receiving process into one of these three locations, based on the quantity on hand for each of the three locations. When the quantity on hand at the forward stock location (e.g. storage carousels in the ALV, ULV or a shelf location outside of the LVK) is below par level, a replenishment task is generated for the ALV/ULV. If the number of outstanding orders for that medication item is less than the remaining quantity on hand, then the request is considered to be a low level replenishment task. If the number of outstanding orders for that medication item is greater than the remaining quantity on hand, then the request is considered to be a high level replenishment task. Via the handheld manual scanners, the operator will be prompted to replenish the forward stock location from a specific back stock location (if there is one) or directly from the warehouse stock location when a back stock location does not exist or was assigned or if the quantity on hand for a specific back stock location is zero. Otherwise, it is a FEFO then FIFO pull of inventory through the pharmacy to each one of these stocking locations. The inventory across each of the filling systems in the pharmacy can be monitored and controlled for various reasons. Because items are not depleted from inventory until a patient label is confirmed on the product (or when the product is placed in a reject bin for restocking, which takes the product out of "on-hand" inventory only), the rates of how particular items are being requested from stock can be determined and analyzed to determine if the size of storage locations for those particular items needs to be adjusted to make more room or less room for these particular items. In this regard, the storage capacity of the storage locations is continuously optimized based on the output of the pharmacy.

Embodiments of the invention may facilitate labeling and verifying products of customer orders using the stand-alone LVK 10 and/or using the ULV system 100. As described above, a customer order may be processed at a pharmacy host server 110 and organized into pick data, and the pick data may be communicated to one or more LVKs 10, 104 for processing. An operator may log-in to the LVK 10, 104 and the pharmacy host server 110 may communicate pick data indicating products that are required to be labeled and verified for the pending customer order. To begin the process, the operator may scan the machine readable indicia 60 associated with the first tote 56 using scanners 36 associated with the LVK 10, 104 or the hand-held scanner 74. The LVK 10, 104 determines whether the tote 56 is already assigned to another customer order/batch, and if not, the LVK 10, 104 generates batch data from the pick data for the first tote 56.

Consistent with embodiments of the invention, the operator may scan the first product with scanners 36, and the LVK 10, 104 generates the patient label 192 including the patient barcode (or other such machine readable indicia such as a QR code) for the first product. The operator affixes the patient label 192 to the first product and scans the labeled product again. The LVK 10 confirms that the patient label 192 is affixed to the correct product (i.e., that the patient indicated by the patient barcode is supposed to be on the first product) for the customer order, and if correct, the LVK 10, 104 will indicate to the operator that the verification is complete, and the operator places the labeled and verified product in the first tote 56. If however, an incorrect patient label 192 is affixed to the first product, the LVK 10, 104 may indicate that the product is not verified, and the LVK 10, 104 may print a new patient label 192 for the first product and instruct the operator to remove the incorrect patient label 192 and affix the new patient label 192. After a predetermined number of attempts, the LVK 10, 104 may instruct the operator to place the first product in a rejection bin. At each step, the LVK may provide direction and/or information regarding the process flow to the operator via the display 32, and the operator may provide input data to the LVK 10 via the HMI 180 including an input peripheral 318, such as the display 32 if the display 32 is a touch-screen display.

In addition, prior to scanning the first product for verification, the operator may indicate to the LVK 10, 104 that the first product is a flag label product (i.e., the first product includes more than one medical item, where each included medical item requires a flag label). Alternatively, in some embodiments, the LVK 10, 104 may query the product database 356 to determine whether the first product is a flag label product. As such, the LVK 10, 104 may generate flag labels for the operator to affix as appropriate.

If the first tote 56 becomes full and picks remain in the batch data for the first tote 56, the operator may scan another, second tote 56, and the remaining picks will be reassigned to the batch data for the second tote 56. When all picks in the batch data have been labeled and verified, and/or the first tote 56 becomes full, the LVK 10, 104 instructs the operator to take the first tote 56 to another location, such as a QA station and/or a shipping station.

With respect to embodiments of the invention utilizing the ULV system 100, in addition to the labeling and verification of one or more products for the batch data, the storage carousel 108 may be rotated to align one or more vertical storage columns 165 including storage bins 140 storing products in the batch data to the pick location 130. Hence, in these embodiments, the operator may retrieve products from the first aligned vertical storage column 165 as instructed by selectively operated pick modules 114. The pick modules 114 corresponding to storage bins 140 of the aligned vertical storage column 165 storing a required product may be illuminated to indicate to the operator that at least one unit of the product should be retrieved from the indicated storage bin 140. After the operator labels and verifies all the required units from an indicated storage bin 140, the pick module 114 corresponding to the indicated storage bin 140 may be extinguished, thereby indicating to the operator that no more units are needed of the product. After the operator labels and verifies all the required units from the aligned vertical storage column 165, the storage carousel 108 may be rotated to align another vertical storage column 165 including at least one storage bin 140 that stores a product of the batch data. This sequence continues until all units of each product of the batch data stored in the storage carousel 108 have been labeled and verified. If the batch is complete, the LVK 104 may output directions to the operator instructing the operator on where to take the tote 56. If all products stored at the storage carousel 108 have been labeled and verified but picks remain in the batch data, the LVK 104 may instruct the user to take the tote 56 to another storage location, such as another LVK 104 and storage carousel 108, or a particular shelf location.

Although the storage carousel 108 shown with the ULV system 100 has been described with a control process to deliver batches of medical items or products to an operator for labeling and verification, the storage carousel 108 may also be used in connection with blister cards and product boxes in the automated label and verification (ALV) system setting in other embodiments. For example, such an automated label and verification system has been concurrently developed as described in U.S. patent application Ser. No. 13/801,070 to Carson et al., entitled "Automated Label and Verification Systems and Methods for Filling Customer Orders of Medical Items" which is co-owned by the assignee of the present invention and is hereby incorporated by reference herein in its entirety.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. In particular, any of the blocks of the above flowcharts may be deleted, augmented, made to be simultaneous with another, combined, or be otherwise altered in accordance with the principles of the invention. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method for filling a customer order containing at least one product to be labeled and verified with a label and verification (LV) kiosk including a scanner, a label printer, and a human machine interface (HMI), each product including a medical item, and the method comprising:
    prompting a user with the HMI to manually scan a product label on a product contained in the customer order at the scanner;
    receiving first identification data from the product label manually scanned by the user with the scanner, the first identification data being associated with the product;
    determining whether the first identification data corresponds to a medical item contained in the customer order;
    printing a patient label containing second identification data with the label printer if the first identification data corresponds to a medical item contained in the customer order, the second identification data being associated with a patient who is to receive the product;
    prompting the user with the HMI to manually affix the patient label to the product and to manually scan the product label and the patient label at the scanner; and
    verifying that the patient label was affixed to the product by confirming that the first and second identification data were each received and correctly correspond to the customer order when the product label and the patient label were manually scanned by the user with the scanner.

2. The method of claim 1, wherein when the first identification data cannot be determined to correspond to at least one of the products contained in the customer order, the method further comprises:
    prompting the user with the HMI to return the product with the product label that has been scanned and to retrieve a new product contained in the customer order.

3. A method for filling a customer order containing at least one product to be labeled and verified with a label and verification (LV) kiosk including a scanner, a label printer, and a human machine interface (HMI), each product including a medical item, and the method comprising:
    prompting a user with the HMI to scan a product label on a product contained in the customer order at the scanner;
    receiving first identification data from the product label scanned by the user with the scanner, the first identification data being associated with the product;
    determining whether the first identification data corresponds to a medical item contained in the customer order;
    printing a patient label containing second identification data with the label printer if the first identification data corresponds to a medical item contained in the customer order, the second identification data being associated with a patient who is to receive the product;
    prompting the user with the HMI to affix the patient label to the product and to scan the product label and the patient label at the scanner;
    verifying that the patient label was affixed to the product by confirming that the first and second identification data were each received and correctly correspond to the customer order when the product label and the patient label were scanned by the user with the scanner;
    generating pick instructions identifying a storage location for each of the products contained in the customer order to be filled;
    providing the pick instructions to the user with the HMI for a first product contained in the customer order, such that the user can retrieve the first product and then label and verify the first product using the prompting, receiving, determining, printing, prompting, and verifying steps; and
    repeating the steps of providing the pick instructions and labeling and verifying for each other products contained in the customer order.

4. The method of claim 3, wherein the LV kiosk includes a display screen at the HMI and a kiosk housing separated from a plurality of racks and/or carousels defining storage locations for bulk supply of products, and providing the pick instructions to the user with the HMI further comprises:
    providing the pick instructions by generating a message on the display screen identifying which of the plurality of racks and/or carousels hold the first product to be retrieved by the user.

5. The method of claim 4, wherein the LV kiosk includes a kiosk housing connected to a storage carousel located within a cage having a door, the storage carousel including a plurality of radially oriented storage bins on a plurality of shelves for holding bulk supply of products, and the method further comprises:
    determining with the pick instructions a first location on the storage carousel in which a storage bin holds the first product to be retrieved; and
    actuating the storage carousel to rotate to present the first location at the door of the cage such that the user can retrieve the first product.

6. The method of claim 5, wherein the LV kiosk includes a display screen at the HMI and a plurality of pick modules located on the kiosk housing adjacent to corresponding shelves on the storage carousel, and providing the pick instructions to the user with the HMI further comprises:

selectively operating the pick module corresponding to the shelf of the storage carousel including the first location after the first location has been rotated to the door of the cage; and generating a message on the display screen prompting the user to use the operating pick module to find and retrieve the first product.

7. The method of claim 6, wherein after the first product has been labeled and verified, the method further comprises:

prompting the user to place the first product into a storage tote located proximate to the LV kiosk; and determining with the pick instructions a second location on the storage carousel in which a storage bin holds a second product to be retrieved and actuating the storage carousel to rotate to present the second location at the door of the cage simultaneous to prompting the user to place the first product into the storage tote such that the second location will be accessible to the user immediately after the first product has been placed into the storage tote.

8. The method of claim 7, wherein the storage carousel includes storage bins holding controlled substances, the door on the cage is motorized, and when the first product is a controlled substance, the method further comprises:

closing the motorized door to prevent access to the storage bins of the storage carousel before providing any pick instructions to retrieve a product from the storage carousel;

verifying third identification data provided by the user at the HMI to determine if the user is authorized to retrieve controlled substances; and opening the motorized door to provide access to the storage carousel only when the third identification data has verified that the user is authorized to retrieve controlled substances and only after the first location has been rotated to the door of the cage.

9. The method of claim 8, wherein the plurality of radially oriented storage bins in the storage carousel define separated vertical columns containing groups of storage bins that may be presented simultaneously for access at the door of the cage, and the method further comprises:

maintaining controlled substances of different schedule levels in different vertical columns of the storage carousel, thereby separating controlled substances of different schedule levels in independent pie-piece-shaped portions of the storage carousel; and rotating the storage carousel such that the portions of the storage carousel containing controlled substances of a schedule level higher than what the user is authorized to remove are never rotated past the door, thereby preventing a user from having even temporary access to controlled substances of a schedule level higher than what the user is authorized to remove.

10. The method of claim 8, wherein the LV kiosk includes a display screen at the HMI, the kiosk housing is connected to a plurality of storage carousels, and the method further comprises:

determining with the pick instructions which of the plurality of storage carousels includes a first location in which a storage bin holds the first product to be retrieved; and generating a message on the display screen for the user that identifies which of the plurality of storage carousels includes the first location such that the user can go to that storage carousel to retrieve the first product.

11. The method of claim 9, wherein the storage carousel also includes a light curtain optical sensor located adjacent to the door, and actuating the storage carousel to rotate to present the first location at the door of the cage further comprises:

detecting with the light curtain optical sensor an entry of a user's arm into the storage carousel from outside the cage; and stopping rotating movement of the storage carousel whenever the user's arm is detected by the optical sensor to avoid injuring the user.

12. A method for filling a customer order containing at least one product to be labeled and verified with a label and verification (LV) kiosk including a scanner, a label printer, and a human machine interface (HMI), each product including a medical item, and the method comprising:

prompting a user with the HMI to scan a product label on a product contained in the customer order at the scanner;

receiving first identification data from the product label scanned by the user with the scanner, the first identification data being associated with the product;

determining whether the first identification data corresponds to a medical item contained in the customer order;

printing a patient label containing second identification data with the label printer if the first identification data corresponds to a medical item contained into eh customer order, the second identification data being associated with a patient who is to receive the product;

prompting the user with the HMI to affix the patient label to the product and to scan the product label and the patient label at the scanner; and verifying that the patient label was affixed to the product by confirming that the first and second identification data were each received and correctly correspond to the customer order when the product label and the patient label were scanned by the user with the scanner;

wherein when the first and second identification data cannot be verified to correctly correspond to the customer order, the method further comprises;

printing a replacement patient label containing the second identification data associated with a patient who is to receive the product; and prompting the user with the HMI to remove the patient label originally affixed to the product, to affix the replacement patient label to the product, and to scan the product label and the replacement patient label at the scanner.

13. A method for filling a customer order containing at least one product to be labeled and verified with a label and verification (LV) kiosk including a scanner, a label printer, and a human machine interface (HMI), each product including a medical item, and the method comprising:

prompting a user with the HMI to scan a product label on a product contained in the customer order at the scanner;

receiving first identification data from the product label scanned by the user with the scanner, the first identification data being associated with the product;

determining whether the first identification data corresponds to a medical item contained in the customer order;

printing a patient label containing second identification data with the label printer if the first identification data corresponds to a medical item contained in the customer order, the second identification data being associated with a patient who is to receive the product;

prompting the user with the HMI to affix the patient label to the product and to scan the product label and the patient label at the scanner;

verifying that the patient label was affixed to the product by confirming that the first and second identification data were each received and correctly correspond to the customer order when the product label and the patient label were scanned by the user with the scanner;

determining whether the product with the product label that has been scanned is a flag label product, which requires a flag label to be applied that contains a subset of information contained on the patient label; and printing a flag label responsive to determining that the product is a flag label product such that the user can affix the flag label to the product.

14. A label and verification kiosk configuered to fill a customer order containing at least one product, each product including a medical item, and the kiosk comprising:

a kiosk housing;

a label printer located at the kiosk housing and operable to print a patient label;

a scanner located at the kiosk housing and operable to scan product labels on products and patient labels;

a human machine interface (HMI) including a display screen located at the kiosk housing, the HMI configured to provide instruction prompts to a user;

a controller having a processor and a memory;

a program code resident in the memory and configured to be executed by the processor to determine if first identification data from a product label on a product scanned by the user at the scanner corresponds to a medical item in the customer order, actuate printing of a patient label containing second identification data with the label printer, prompt the user with the HMI to affix the patient label to the product, and verify that the patient label was affixed to the product by confirming that the first and second identification data were each received when the product label and the patient label are scanned by the user with the scanner; and at least one auxiliary shelf located at the kiosk housing and configured to hold totes in proximate relation to the label printer, the scanner, and the HMI such that the user can collect a plurality of products for the customer order into a tote from storage racks and carousels separate from the kiosk housing, and then place the tote onto the at least one auxiliary shelf for ready access during labeling and verification of the plurality of products in the tote.

15. A label and verification kiosk configueried to fill a customer order containing at least one product, each product including a medical item, and the kiosk comprising:

a kiosk housing;

a label printer located at the kiosk housing and operable to print a patient label;

a scanner located at the kiosk housing and operable to scan product labels on products and patient labels;

a human machine interface (HMI) including a display screen located at the kiosk housing, the HMI configured to provide instruction prompts to a user;

a controller having a processor and a memory;

a program code resident in the memory and configured to be executed by the processor to determine if first identification data from a product label on a product scanned by the user at the scanner corresponds to a medical item in the customer order, actuate printing of a patient label containing second identification data with the label printer, prompt the user with the HMI to affix the patient label to the product, and verify that the patient label was affixed to the product by confirming that the first and second identification data were each received when the product label and the patient label are scanned by the user with the scanner; and a work shelf projecting from the kiosk housing adjacent to the label printer and the scanner, the work shelf sized to accommodate only one product such that the user is encouraged to label and verify only one product at a time for the customer order.

16. A label and verification system configured to fill a customer order containing at least one product, each product including a medical item, and the system comprising:

a storage carousel including a plurality of radially oriented storage bins on a plurality of shelves for holding bulk supply of products;

a cage surrounding the storage carousel, the cage including a door configured to provide selective access to one of the storage bins on each shelf of the storage carousel that faces towards the door; and a label and verification kiosk coupled to the cage and comprising:

a kiosk housing at least partially surrounding the storage carousel and located adjacent to the door;

a label printer located at the kiosk housing and operable to print a patient label;

a scanner located at the kiosk housing and operable to scan product labels and patient labels on products;

a controller having a processor and a memory; and program code resident in the memory and configured to be executed by the processor to identify a first location in the storage carousel containing a storage bin with a first product for the customer order, actuate the storage carousel to rotate the first location to the door of the cage so that a user can access the storage bin with the first product, and actuate a manual labeling and verification of the first product using the label printer and the scanner after retrieval from the storage carousel.

17. The label and verification system of claim 16, further comprising:

a light curtain optical sensor coupled to the controller and located adjacent to the door, the optical sensor operable to detect entry of a user's arm into the storage carousel from outside the cage such that the rotation of the storage carousel can be stopped whenever the user's arm is detected by the optical sensor.

18. The label and verification system of claim 16, wherein the label and verification kiosk further comprises:

a plurality of pick modules located on the kiosk housing adjacent to corresponding shelves on the storage carousel, the controller being operable to actuate the pick module adjacent to the corresponding shelf carrying the first location when the first location is rotated to the door of the cage.

19. The label and verification system of claim 16, wherein the storage carousel includes storage bins holding controlled substances, and the door on the cage is motorized such that the controlled substances in the storage carousel cannot be accessed by a user until authorized access is granted by the controller.

* * * * *

UNITED STATES PATENT AND TRADEMARK OFFICE
CERTIFICATE OF CORRECTION

PATENT NO. : 9,117,016 B2
APPLICATION NO. : 13/801017
DATED : August 25, 2015
INVENTOR(S) : Bradley E. Carson et al.

It is certified that error appears in the above-identified patent and that said Letters Patent is hereby corrected as shown below:

At claim 5, column 40, line 51, "The method of claim 4, wherein the LV kiosk includes a"

should read -- The method of claim 3, wherein the LV kiosk includes a --.

At claim 7, column 41, line 8, "The method of claim 6, wherein after the first product has"

should read -- The method of claim 5, wherein after the first product has --.

At claim 8, column 41, line 22, "The method of claim 7, wherein the storage carousel"

should read -- The method of claim 5, wherein the storage carousel --.

At claim 10, column 41, line 55, "The method of claim 8, wherein the LV kiosk includes"

should read -- The method of claim 5, wherein the LV kiosk includes --.

At claim 11, column 41, line 66, "The method of claim 9, wherein the storage carousel"

should read -- The method of claim 5, wherein the storage carousel --.

At claim 12, column 42, line 25, "corresponds to a medical item contained into eh cus-"

should read -- corresponds to a medical item contained in the cus- --.

At claim 15, column 43, line 45, "A label and verification kiosk configuered to fill a"

should read -- A label and verification kiosk configured to fill a --.

Signed and Sealed this
Twenty-second Day of March, 2016

Michelle K. Lee
*Director of the United States Patent and Trademark Office*